US012600994B2

(12) United States Patent
Ferreira et al.

(10) Patent No.: US 12,600,994 B2
(45) Date of Patent: Apr. 14, 2026

(54) β-KETOACYL-ACP SYNTHASE IV VARIANTS

(71) Applicant: CORBION BIOTECH, INC., South San Francisco, CA (US)

(72) Inventors: Joshua Ferreira, South San Francisco, CA (US); Janice Lau Wee, South San Francisco, CA (US); Nien-Hsi Ko, South San Francisco, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 801 days.

(21) Appl. No.: 17/793,123

(22) PCT Filed: Jan. 15, 2021

(86) PCT No.: PCT/US2021/013575
§ 371 (c)(1),
(2) Date: Jul. 15, 2022

(87) PCT Pub. No.: WO2021/146520
PCT Pub. Date: Jul. 22, 2021

(65) Prior Publication Data
US 2023/0143841 A1 May 11, 2023

Related U.S. Application Data

(60) Provisional application No. 62/961,996, filed on Jan. 16, 2020.

(51) Int. Cl.
| | |
|---|---|
| *C12P 7/6445* | (2022.01) |
| *C12N 9/10* | (2006.01) |
| *C12N 9/16* | (2006.01) |
| *C12N 15/62* | (2006.01) |
| *C12N 15/74* | (2006.01) |

(52) U.S. Cl.
CPC .......... *C12P 7/6445* (2013.01); *C12N 9/1029* (2013.01); *C12N 9/16* (2013.01); *C12N 15/62* (2013.01); *C12N 15/74* (2013.01); *C12Y 203/01041* (2013.01)

(58) Field of Classification Search
CPC ....... C12P 7/6445; C12N 9/1029; C12N 9/16; C12N 15/62; C12N 15/74; C12Y 203/01041; C07K 2319/01; C07K 2319/42; C07K 2319/43
See application file for complete search history.

(56) References Cited

U.S. PATENT DOCUMENTS

| | | | |
|---|---|---|---|
| 5,298,421 A | 3/1994 | Davies et al. | |
| 5,304,481 A | 4/1994 | Davies et al. | |
| 5,344,771 A | 9/1994 | Davies et al. | |
| 5,455,167 A | 10/1995 | Voelker et al. | |
| 5,512,482 A | 4/1996 | Voelker et al. | |
| 5,639,790 A | 6/1997 | Voelker et al. | |
| 5,654,495 A | 8/1997 | Voelker et al. | |
| 5,667,997 A | 9/1997 | Voelker et al. | |
| 5,723,761 A | 3/1998 | Voelker et al. | |
| 5,807,893 A | 9/1998 | Voelker et al. | |
| 5,850,022 A | 12/1998 | Dehesh et al. | |
| 7,135,290 B2 | 11/2006 | Dillon | |
| 2012/0283460 A1 | 11/2012 | Franklin et al. | |
| 2012/0288930 A1 | 11/2012 | Trimbur et al. | |
| 2014/0178950 A1 | 6/2014 | Franklin et al. | |
| 2016/0010066 A1* | 1/2016 | Davis .................... C12P 7/6463 435/320.1 |
| 2017/0044580 A1 | 2/2017 | Sugihara et al. | |
| 2018/0216144 A1 | 8/2018 | Rakitsky | |

FOREIGN PATENT DOCUMENTS

| | | | |
|---|---|---|---|
| WO | WO 2008/151149 A2 | 12/2008 | |
| WO | WO 2010/063032 A2 | 6/2010 | |
| WO | WO 2010/120939 A2 | 10/2010 | |
| WO | WO 2011/150410 A2 | 12/2011 | |
| WO | WO 2011/150411 A1 | 12/2011 | |
| WO | WO 2012/106560 A1 | 8/2012 | |
| WO | WO 2014/120829 A1 | 8/2014 | |
| WO | WO 2014/151904 A1 | 9/2014 | |
| WO | WO 2016/007862 A2 | 1/2016 | |
| WO | WO 2016/014968 A1 | 1/2016 | |
| WO | WO 2016/044779 A2 | 3/2016 | |
| WO | WO 2018/067849 A2 | 4/2018 | |

OTHER PUBLICATIONS

Dehesh et al. "KAS IV: a 3-ketoacyl-ACP synthase form *Cuphea* sp. is a medium chain specific condensing enzyme", *The Plant Journal,* vol. 15, No. 3, pp. 383-390 (1998).

Frenz et al., "Hydrocarbon recovery by extraction with a biocompatible solvent from free and immobilized cultures of *Botryococcus braunii*", *Enzyme and Microbial Technology,* vol. 11, No. 11, p. 717-724 (1989).

Gül et al., "Sterols and the phytosterol content in oilseed rape (*Brassica napus* L.)", *Journal of Cell and Molecular Biology,* vol. 5, Issue 2, pp. 71-79 (2006).

Hawkins et al., "Expression of human growth hormone by the eukaryotic alga, *Chlorella*", *Current Microbiology,* vol. 38, pp. 335-341 (1999).

International Searching Authority, International Search Report and Written Opinion issued in International Patent Application No. PCT/US2021/013575, mailed on Mar. 5, 2021.

Koh et al., "The use of enzymatically synthesized medium- and long-chain triacylglycerols (MLCT) oil blends in food application", *International Food Research Journal,* vol. 18, pp. 355-366 (2011).

(Continued)

*Primary Examiner* — Robert B Mondesi
*Assistant Examiner* — Benjamin Hall Easton
(74) *Attorney, Agent, or Firm* — Sunit Talapatra; Foley & Lardner LLP

(57) ABSTRACT

Provided are non-natural or variant β-ketoacyl-acyl carrier protein (ACP) synthase (KAS) IVa enzymes (KASIVa), polynucleotides encoding such variant KASIVa, host cells expressing such variant KASIVa, oils and oil products produced by such cells, and methods of making and using such variant KASIVa.

21 Claims, No Drawings

Specification includes a Sequence Listing.

(56) References Cited

OTHER PUBLICATIONS

Mendes et al., "Supercritical carbon dioxide extraction of compounds with pharmaceutical importance from microalgae", *Inorganica Chimica Acta,* vol. 356, pp. 328-334 (2003).

Miao et al., "High yield bio-oil production from fast pyrolysis by metabolic controlling of *Chlorella protothecoides*", *Journal of Biotechnology,* vol. 110, pp. 85-93 (2004).

Miao et al., "Biodiesel production from heterotrophic microalgal oil", *Bioresource Technology,* vol. 97, No. 6, pp. 841-846 (2006).

Needleman et al., "A general method applicable to the search for similarities in the amino acid sequence of two proteins", *Journal of Molecular Biology,* vol. 48, No. 3, pp. 443-453 (1970).

Croteau et al., "Ketogenic Medium Chain Triglycerides Increase Brain Energy Metabolism in Alzheimer's Disease", *Journal of Alzheimer's Disease,* 64(2): 551-561 (2018).

Huang et al., "Sterols as ecological indicators", *Geochimica et Cosmochimica Acta,* 43(5): 739-745 (1979).

Slover et al., "Determination of tocopherols and sterols by capillary gas chromatography," *Journal of the American Oil Chemists' Society,* 60(8): 1524-1528 (1983).

* cited by examiner

SEQUENCE LISTING

<160> NUMBER OF SEQ ID NOS: 25

<210> SEQ ID NO 1
<211> LENGTH: 12642
<212> TYPE: DNA
<213> ORGANISM: Artificial Sequence
<220> FEATURE:
<223> OTHER INFORMATION: synthetic

<400> SEQUENCE: 1

```
agcggaagag cgcccaatgt ttaaacccct caactgcgac gctgggaacc ttctccgggc      60
aggcgatgtg cgtgggtttg cctccttggc acggctctac accgtcgagt acgccatgag     120
gcggtgatgg ctgtgtcggt tgccacttcg tccagagacg gcaagtcgtc catcctctgc     180
gtgtgtggcg cgacgctgca gcagtccctc tgcagcagat gagcgtgact ttggccattt     240
cacgcactcg agtgtacaca atccattttt cttaaagcaa atgactgctg attgaccaga     300
tactgtaacg ctgatttcgc tccagatcgc acagatagcc accatgttgc tgcgtctgaa     360
aatctggatt ccgaattcga ccctggcgct ccatccatgc aacagatggc gacacttgtt     420
acaattcctg tcacccatcg gcatggagca ggtccactta gattcccgat cacccacgca     480
catctcgcta atagtcattc gttcgtgtct tcgatcaatc tcaagtgagt gtgcatggat     540
cttggttgac gatgcggtat gggtttgcgc cgctggctgc agggtctgcc caaggcaagc     600
taacccagct cctctccccg acaatactct cgcaggcaaa gccggtcact tgccttccag     660
attgccaata aactcaatta tggcctctgt catgccatcc atgggtctga tgaatggtca     720
cgctcgtgtc ctgaccgttc cccagcctct ggcgtcccct gccccgccca ccagcccacg     780
ccgcgcggca gtcgctgcca aggctgtctc ggaggtaccc tttcttgcgc tatgacactt     840
ccagcaaaag gtagggcggg ctgcgagacg gcttcccggc gctgcatgca acaccgatga     900
tgcttcgacc ccccgaagct ccttcggggc tgcatgggcg ctccgatgcc gctccagggc     960
gagcgctgtt taaatagcca ggcccccgat tgcaaagaca ttatagcgag ctaccaaagc    1020
catattcaaa cacctagatc actaccactt ctacacaggc cactcgagct tgtgatcgca    1080
ctccgctaag ggggcgcctc ttcctcttcg tttcagtcac aacccgcaaa ctctagaata    1140
tcaatgctgc tgcaggcctt cctgttcctg ctggccggct cgccgccaa gatcagcgcc    1200 tccatgacga acgagacgtc cgaccgcccc ctggtgcact tcacccccaa caagggctgg    1260
atgaacgacc ccaacggcct gtggtacgac gagaaggacg ccaagtggca cctgtacttc    1320
cagtacaacc cgaacgacac cgtctggggg acgcccttgt tctggggcca cgccacgtcc    1380
gacgacctga ccaactggga ggaccagccc atcgccatcg ccccgaagcg caacgactcc    1440
ggcgccttct ccggctccat ggtggtggac tacaacaaca cctccggctt cttcaacgac    1500
accatcgacc cgcgccagcg ctgcgtggcc atctggacct acaacacccc ggagtccgag    1560
gagcagtaca tctcctacag cctggacggc ggctacacct tcaccgagta ccagaagaac    1620
cccgtgctgg ccgccaactc cacccagttc cgcgacccga aggtcttctg gtacgagccc    1680
tcccagaagt ggatcatgac cgcggccaag tcccaggact acaagatcga gatctactcc    1740
tccgacgacc tgaagtcctg gaagctggag tccgcgttcg ccaacgaggg cttcctcggc    1800
taccagtacg agtgccccgg cctgatcgag gtccccaccg agcaggaccc cagcaagtcc    1860
tactgggtga tgttcatctc catcaacccc ggcgccccgg ccggcggctc cttcaaccag    1920
tacttcgtcg gcagcttcaa cggcacccac ttcgaggcct cgacaaacca gtcccgcgtg    1980
gtggacttcg gcaaggacta ctacgccctg cagacctcct caacaccga cccgacctac    2040
```

```
gggagcgccc tgggcatcgc gtgggcctcc aactgggagt actccgcctt cgtgcccacc   2100 aaccccctggc gctcctccat gtccctcgtg cgcaagttct ccctcaacac cgagtaccag   2160
gccaacccgg agacggagct gatcaacctg aaggccgagc cgatcctgaa catcagcaac   2220
gccggcccct ggagccggtt cgccaccaac accacgttga cgaaggccaa cagctacaac   2280
gtcgacctgt ccaacagcac cggcaccctg gagttcgagc tggtgtacgc cgtcaacacc   2340
acccagacga tctccaagtc cgtgttcgcg gacctctccc tctggttcaa gggcctggag   2400
gaccccgagg agtacctccg catgggcttc gaggtgtccg cgtcctcctt cttcctggac   2460
cgcgggaaca gcaaggtgaa gttcgtgaag gagaacccct acttcaccaa ccgcatgagc   2520
gtgaacaacc agcccttcaa gagcgagaac gacctgtcct actacaaggt gtacggcttg   2580
ctggaccaga acatcctgga gctgtacttc aacgacggcg acgtcgtgtc caccaacacc   2640
tacttcatga ccaccgggaa cgccctgggc tccgtgaaca tgacgacggg ggtggacaac   2700
ctgttctaca tcgacaagtt ccaggtgcgc gaggtcaagt gacaattgac gcccgcgcgg   2760
cgcacctgac ctgttctctc gagggcgcct gttctgcctt gcgaaacaag ccctggagc   2820 atgcgtgcat gatcgtctct ggcgccccgc cgcgcggttt gtcgccctcg cgggcgccgc   2880
ggccgcgggg gcgcattgaa attgttgcaa accccacctg acagattgag ggcccaggca   2940
ggaaggcgtt gagatggagg tacaggagtc aagtaactga aagtttttat gataactaac   3000
aacaaagggt cgtttctggc cagcgaatga caagaacaag attccacatt tccgtgtaga   3060
ggcttgccat cgaatgtgag cgggcgggcc gcggacccga caaaacccctt acgacgtggt   3120 aagaaaaacg tggcgggcac tgtccctgta gcctgaagac cagcaggaga cgatcggaag   3180
catcacagca caggatcccg cgtctcgaac agagcgcgca gaggaacgct gaaggtctcg   3240
cctctgtcgc acctcagcgc ggcatacacc acaataacca cctgacgaat gcgcttggtt   3300
cttcgtccat tagcgaagcg tccggttcac acacgtgcca cgttggcgag gtggcaggtg   3360
acaatgatcg gtggagctga tggtcgaaac gttcacagcc tagggaattc ctgaagaatg   3420
ggaggcaggt gttgttgatt atgagtgtgt aaaagaaagg ggtagagagc cgtcctcaga   3480
tccgactact atgcaggtag ccgctcgccc atgcccgcct ggctgaatat tgatgcatgc   3540
ccatcaaggc aggcaggcat ttctgtgcac gcaccaagcc cacaatcttc cacaacacac   3600
agcatgtacc aacgcacgcg taaaagttgg ggtgctgcca gtgcgtcatg ccaggcatga   3660
tgtgctcctg cacatccgcc atgatctcct ccatcgtctc gggtgtttcc ggcgcctggt   3720
ccgggagccg ttccgccaga tacccagacg ccacctccga cctcacgggg tacttttcga   3780
gcgtctgccg gtagtcgacg atcgcgtcca ccatggagta gccgaggcgc cggaactggc   3840
gtgacggagg gaggagaggg aggagagaga gggggggggg ggggggggat gattacacgc   3900
cagtctcaca acgcatgcaa gacccgtttg attatgagta caatcatgca ctactagatg   3960
gatgagcgcc aggcataagg cacaccgacg ttgatggcat gagcaactcc cgcatcatat   4020
ttcctattgt cctcacgcca agccggtcac catccgcatg ctcatattac agcgcacgca   4080
ccgcttcgtg atccaccggg tgaacgtagt cctcgacgga aacatctggc tcgggcctcg   4140
tgctggcact ccctcccatg ccgacaacct ttctgctgtc accacgaccc acgatgcaac   4200
gcgacacgac ccggtgggac tgatcggttc actgcacctg catgcaattg tcacaagcgc   4260
atactccaat cgtatccgtt tgatttctgt gaaaactcgc tcgaccgccc gcgtcccgca   4320
ggcagcgatg acgtgtgcgt gacctgggtg tttcgtcgaa aggccagcaa ccccaaatcg   4380
```

-continued

```
caggcgatcc ggagattggg atctgatccg agcttggacc agatccccca cgatgcggca    4440
cgggaactgc atcgactcgg cgcggaaccc agctttcgta aatgccagat tggtgtccga    4500
taccttgatt tgccatcagc gaaacaagac ttcagcagcg agcgtatttg gcgggcgtgc    4560 taccaggggtt gcatacattg cccatttctg tctggaccgc tttaccggcg cagagggtga    4620
gttgatgggg ttggcaggca tcgaaacgcg cgtgcatggt gtgtgtgtct gttttcggct    4680
gcacaatttc aatagtcgga tgggcgacgg tagaattggg tgttgcgctc gcgtgcatgc    4740
ctcgccccgt cgggtgtcat gaccgggact ggaatccccc ctcgcgaccc tcctgctaac    4800
gctcccgact ctcccgcccg cgcgcaggat agactctagt tcaaccaatc gacacatatg    4860
gcttccgcgg cattcaccat gtcggcgtgc cccgcgatga ctggcagggc ccctgggca    4920 cgtcgctccg gacggccagt cgccaccgc ctgaggggct ccaccttcca gtgcctggtg    4980
aactcccaca tcgacccctg caaccagaac gtgtcctccg cctccctgtc cttcctgggc    5040
gacaacggct tcggctccaa cccccttccgc tccaaccgcg gccaccgccg cctgggccgc    5100
gcctcccact ccggcgaggc catggccgtg gccctgcagc ccgcccagga ggtggccacc    5160
aagaagaagc ccgccatcaa gcagcgccgc gtggtggtga ccggcatggg cgtggtgacc    5220
cccctgggcc acgagcccga cgtgttctac aacaacctgc tggacggcgt gtccggcatc    5280
tccgagatcg agaccttcga ctgcacccag ttccccaccc gcatcgccgg cgagatcaag    5340
tccttctcca ccgacggctg ggtggcccccc aagctgtcca agcgcatgga caagttcatg    5400
ctgtacctgc tgaccgccgg caagaaggcc ctggccgacg ccggcatcac cgaggacgtg    5460
atgaaggagc tggacaagcg caagtgcggc gtgctgatcg gctccggcat gggcggcatg    5520
aagctgttca acgactccat cgaggccctg cgcgtgtcct acaagaagat gaaccccttc    5580
tgcgtgccct tcgccaccac caacatgggc tccgccatgc tggccatgga cctgggctgg    5640 atgggccccca actactccat ctccaccgcc tgcgccacct ccaacttctg catcctgaac    5700
gccgccaacc acatcatccg cggcgaggcc gacatgatgc tgtgcggcgg ctccgacgcc    5760
gtgatcatcc ccatcggcct gggcggcttc gtggcctgcc gcgccctgtc ccagcgcaac    5820
tccgacccca ccaaggcctc ccgcccctgg gactccaacc gcgacggctt cgtgatgggc    5880
gagggcgccg gcgtgctgct gctggaggag ctggagcacg ccaagaagcg cggcgccacc    5940
atctacgccg agttcctggg cggctccttc acctgcgacg cctaccacat gaccgagccc    6000
caccccgacg gcgccggcgt gatcctgtgc atcgagaagg ccctggccca gtccggcgtg    6060 tccccgcgagg acgtgaacta catcaacgcc cacgccacct ccaccccgc cggcgacatc    6120 aaggagtacc aggccctggc ccactgcttc ggccagaact ccgagctgcg cgtgaactcc    6180
accaagtcca tgatcggcca cctgctgggc gccgccggcg cgtggaggc cgtgaccgtg    6240 atccaggcca tccgcaccgg ctggatccac cccaacctga acctggagga ccccgacgag    6300
gccgtggacc ccaagttcct ggtgggcccc aagaaggagc gcctgaacgt gaaggtgggc    6360
ctgtccaact ccttcggctt cggcggccac aactcctcca tcctgttcgc ccctacaac    6420 accatgtacc cctacgacgt gcccgactac gcctgatatc gaggcagcag cagctcggat    6480
agtatcgaca cactctggac gctggtcgtg tgatggactt ttgccgccac acttgctgcc    6540
ttgacctgtg aatatccctg ccgctttat caaacagcct cagtgtgttt gatcttgtgt    6600
gtacgcgctt ttgcgagttg ctagctgctt gtgctatttg cgaataccac ccccagcatc    6660
cccttccctc gtttcatatc gcttgcatcc caaccgcaac ttatctacgc tgtcctgcta    6720
tccctcagcg ctgctcctgc tcctgctcac tgcccctcgc acagccttgg tttgggctcc    6780
```

```
gcctgtattc tcctggtact gcaacctgta aaccagcact gcaatgctga tgcacgggaa    6840
gtagtgggat gggaacacaa atggaaagct tgggagcagt tgtcgaccgc ccgcgtcccg    6900
caggcagcga tgacgtgtgc gtggcctggg tgtttcgtcg aaaggccagc aaccctaaat    6960
cgcaggcgat ccggagattg ggatctgatc cgagtttgga ccagatccgc cccgatgcgg    7020
cacgggaact gcatcgactc ggcgcggaac ccagctttcg taaatgccag attggtgtcc    7080
gatacctgga tttgccatca gcgaaacaag acttcagcag cgagcgtatt tggcgggcgt    7140
gctaccaggg ttgcatacat tgcccatttc tgtctggacc gctttactgg cgcagagggt    7200
gagttgatgg ggtggcagg catcgaaacg cgcgtgcatg gtgtgcgtgt ctgttttcgg    7260
ctgcacgaat tcaatagtcg gatgggcgac ggtagaattg ggtgtggcgc tcgcgtgcat    7320
gcctcgcccc gtcgggtgtc atgaccggga ctggaatccc ccctcgcgac catcttgcta    7380
acgctcccga ctctcccgac cgcgcgcagg atagactctt gttcaaccaa tcgacaacta    7440
gtaacaatgg ccaccgcctc caccttctcc gccttcaacg cccgctgcgg cgacctgcgc    7500
cgctccgccg gctccggccc ccgccgcccc gccgccccc tgcccgtgcg cgccgccatc     7560
aacgcctccg cccaccccaa ggccaacggc tccgccgtga acctgaagtc cggctccctg    7620
aacacccagg aggacacctc ctcctcccc ccccccgcg ccttcctgaa ccagctgccc      7680
gactggtcca tgctggtgga ctccgtgggc ctgaagtccg tggtgctgga cggcctggtg    7740
tcccgccaga tcttctccat ccgctcctac gagatcggcg ccgaccgcac cgcctccatc    7800
gagaccctga tgaaccacct gcaggagacc tccatcaacc actgcaagtc cctgggcctg    7860
ctgaacgacg gcttcggccg cacccccggc atgtgcaaga acgacctgat ctgggtgctg    7920
accaagatgc agatcatggt gaaccgctac cccacctggg cgacaccgt ggagatcaac     7980 acctggttct cccactccgg caagatcggc atggcctccg actggctgat caccgactgc    8040
aacaccggcg agatcctgat ccgcgccacc tccgtgtggg ccatgatgaa ccagaagacc    8100
cgccgcttct cccgcctgcc ctacgaggtg cgccaggagc tgaccccca ctacgtggac     8160 tcccccacg tgatcgagga caacgaccgc aagctgcaca agttcgacgt gaagaccggc     8220
gactccatcc gcaagggcct gacccccgc tggaacgacc tggacgtgaa ccagcacgtg     8280
tccaacgtga gtacatcgg ctggatcctg gagtccatgc ccatcgaggt gctggagacc     8340
caggagctgt gctccctgac cgtggagtac cgccgcgagt gcggcatgga ctccgtgctg    8400
gagtccgtga ccgccatgga cccctccgag gacgagggcc gctcccagta caagcacctg    8460
ctgcgcctgg aggacggcac cgacatcgtg aagggccgca ccgagtggcg ccccaagaac    8520
gccggcacca acggcgccat ctccaccgcc aagccctcca acggcaactc cgtgtccatg    8580
gactacaagg accacgacgg cgactacaag gaccacgaca tcgactacaa ggacgacgac    8640
gacaagtgac tcgagggagc gacgagtgtg cgtgcggggc tggcgggagt gggacgccct    8700
cctcgctcct ctctgttctg aacggaacaa tcggccaccc cgcgctacgc gccacgcatc    8760
gagcaacgaa gaaaacccc cgatgatagg ttgcggtggc tgccgggata tagatccggc     8820
cgcacatcaa agggccctc cgccagagaa gaagctcctt tcccagcaga ctccttctgc     8880
tgccaaaaca cttctctgtc cacagcaaca ccaaaggat aacagatcaa cttgcgtctc     8940
cgcgtagctt cctcggctag cgtgcttgca acaggtccct gcactattat cttcctgctt    9000
tcctctgaat tatgcggcag cgagcgctc gctctggcga gcgctccttc gcgccgccct     9060
cgctgatcga gtgtacagtc aatgaatggt gagctccagc gccatgccac gcccttgat     9120
```

-continued

```
ggcttcaagt acgattacgg tgttggattg tgtgtttgtt cgtagtgtg catggtttag      9180 aataatacac ttgatttctt gctcacggca atctcggctt gtccgcaggt tcaaccccat      9240
ttcggagtct caggtcagcc gcgcaatgac cagccgctac ttcaaggact tgcacgacaa      9300
cgccgaggtg agctatgttt aggacttgat tggaaattgt cgtcgacgca tattcgcgct      9360
ccgcgacagc acccaagcaa aatgtcaagt gcgttccgat ttgcgtccgc aggtcgatgt      9420
tgtgatcgtc ggcgccggat ccgccggtct gtcctgcgct tacgagctga ccaagcaccc      9480
tgacgtccgg gtacgcgagc tgagattcga ttagacataa attgaagatt aaacccgtag      9540
aaaaatttga tggtcgcgaa actgtgctcg attgcaagaa attgatcgtc ctccactccg      9600
caggtcgcca tcatcgagca gggcgttgct cccggcggcg gcgcctggct gggggggacag      9660 ctgttctcgg ccatgtgtgt acgtagaagg atgaatttca gctggttttc gttgcacagc      9720
tgtttgtgca tgatttgttt cagactattg ttgaatgttt ttagatttct taggatgcat      9780
gatttgtctg catgcgactg aagagcgttt aaaccgcctc tccccgcgcg ttggccgatt      9840
cattaatgca gctggcacga caggtttccc gactggaaag cgggcagtga gcgcaacgca      9900
attaatgtga gttagctcac tcattaggca ccccaggctt tacactttat gcttccggct      9960
cgtatgttgt gtggaattgt gagcggataa caatttcaca caggaaacag ctatgaccat     10020
gattacgcca agctcgaaat taaccctcac taaagggaac aaaagctggc aattcgccct     10080
atagtgagtc gtattacgcg cgctcactgg ccgtcgtttt acaacgtcgt gactgggaaa     10140
accctggcgt tacccaactt aatcgccttg cagcacatcc ccctttcgcc agctggcgta     10200
atagcgaaga ggcccgcacc gatcgccctt cccaacagtt gcgcagcctg aatggcgaat     10260
gggacgcgcc ctgtagcggc gcattaagcg cggcgggtgt ggtggttacg cgcagcgtga     10320
ccgctacact tgccagcgcc ctagcgcccg ctcctttcgc tttcttccct tcctttctcg     10380
ccacgttcgc cggctttccc cgtcaagctc taaatcgggg gctcccttta gggttccgat     10440
ttagtgcttt acggcacctc gaccccaaaa aacttgatta gggtgatggt tcacgtagtg     10500
ggccatcgcc ctgatagacg gtttttcgcc ctttgacgtt ggagtccacg ttctttaata     10560
gtggactctt gttccaaact ggaacaacac tcaaccctat ctcggtctat cttttgatt      10620 tataagggat tttgccgatt tcggcctatt ggttaaaaaa tgagctgatt taacaaaaat     10680
ttaacgcgaa ttttaacaaa atattaacgc ttacaattta ggtggcactt ttcggggaaa     10740
tgtgcgcgga accctatttt gtttattttt ctaaatacat tcaaatatgt atccgctcat     10800
gagacaataa ccctgataaa tgcttcaata atattgaaaa aggaagagta tgagtattca     10860
acatttccgt gtcgccctta ttcccttttt tgcggcattt tgccttcctg tttttgctca     10920
cccagaaacg ctggtgaaag taaaagatgc tgaagatcag ttgggtgcac gagtgggtta     10980
catcgaactg gatctcaaca gcggtaagat ccttgagagt tttcgccccg aagaacgttt     11040
tccaatgatg agcactttta aagttctgct atgtggcgcg gtattatccc gtattgacgc     11100
cgggcaagag caactcggtc gccgcataca ctattctcag aatgacttgg ttgagtactc     11160
accagtcaca gaaaagcatc ttacggatgg catgacagta agagaattat gcagtgctgc     11220
cataaccatg agtgataaca ctgcggccaa cttacttctg acaacgatcg gaggaccgaa     11280
ggagctaacc gcttttttgc acaacatggg ggatcatgta actcgccttg atcgttggga     11340
accggagctg aatgaagcca taccaaacga cgagcgtgac accacgatgc ctgtagcaat     11400
ggcaacaacg ttgcgcaaac tattaactgg cgaactactt actctagctt cccggcaaca     11460
attaatagac tggatggagg cggataaagt tgcaggacca cttctgcgct cggcccttcc     11520
```

-continued

```
ggctggctgg tttattgctg ataaatctgg agccggtgag cgtgggtctc gcggtatcat   11580
tgcagcactg gggccagatg gtaagccctc ccgtatcgta gttatctaca cgacggggag   11640
tcaggcaact atggatgaac gaaatagaca gatcgctgag ataggtgcct cactgattaa   11700
gcattggtaa ctgtcagacc aagtttactc atatatactt tagattgatt taaaacttca   11760
tttttaattt aaaaggatct aggtgaagat cctttttgat aatctcatga ccaaaatccc   11820
ttaacgtgag ttttcgttcc actgagcgtc agacccccgta gaaaagatca aaggatcttc   11880
ttgagatcct tttttttctgc gcgtaatctg ctgcttgcaa acaaaaaaac caccgctacc   11940
agcggtggtt tgtttgccgg atcaagagct accaactctt tttccgaagg taactggctt   12000
cagcagagcg cagataccaa atactgtcct tctagtgtag ccgtagttag gccaccactt   12060
caagaactct gtagcaccgc ctacatacct cgctctgcta atcctgttac cagtggctgc   12120
tgccagtggc gataagtcgt gtcttaccgg gttggactca agacgatagt taccggataa   12180
ggcgcagcgg tcgggctgaa cggggggttc gtgcacacag cccagcttgg agcgaacgac   12240
ctacaccgaa ctgagatacc tacagcgtga gctatgagaa agcgccacgc ttcccgaagg   12300
gagaaaggcg gacaggtatc cggtaagcgg caggtcgga acaggagagc gcacgaggga   12360
gcttccaggg ggaaacgcct ggtatcttta tagtcctgtc gggtttcgcc acctctgact   12420
tgagcgtcga tttttgtgat gctcgtcagg ggggcggagc ctatggaaaa acgccagcaa   12480
cgcggccttt ttacggttcc tggccttttg ctggcctttt gctcacatgt tctttcctgc   12540
gttatcccct gattctgtgg ataaccgtat taccgccttt gagtgagctg ataccgctcg   12600
ccgcagccga acgaccgagc gcagcgagtc agtgagcgag ga                      12642
```

<210> SEQ ID NO 2
<211> LENGTH: 9742
<212> TYPE: DNA
<213> ORGANISM: Artificial Sequence
<220> FEATURE:
<223> OTHER INFORMATION: synthetic

<400> SEQUENCE: 2

```
agcggaagag cgcccaatgt ttaaacagcc cgcaccctcg ttgatctggg agccctgcgc       60
agccccttaa atcatctcag tcaggtttct gtgttcaact gagcctaaag ggctttcgtc      120
atgcgcacga gcacacgtat atcggccacg cagtttctca aaagcggtag aacagttcgc      180
gagccctcgt aggtcgaaaa cttgcgccag tactattaaa ttaaattaat tgatcgaacg      240
agacgcgaaa cttttgcaga atgccaccga gtttgcccag agaatgggag tggcgccatt      300
caccatccgc ctgtgcccgg cttgattcgc cgagacgatg gacggcgaga ccagggagcg      360
gcttgcgagc cccgagccgg tagcaggaac aatgatcgac aatcttcctg tccaattact      420
ggcaaccatt agaaagagcc ggagcgcgtt gaaagtctgc aatcgagtaa tttttcgata      480
cgtcgggcct gctgaaccct aaggctccgg actttgttta aggcgatcca agatgcacgc      540
ggccccaggc acgtatctca agcacaaacc ccagccttag tttcgagact ttgggagata      600
gcgaccgata tctagtttgg cattttgtat attaattacc tcaagcaatg gagcgctctg      660
atgcggtgca gcgtcggctg cagcacctgg cagtggcgct agggtcgccc tatcgctcgg      720
aacctggtca gctggctccc gcctcctgct cagcctcttc cggtaccgta atcccgaggt      780
tggccccgct tccgctggac acccatcgca tcttccggct cgcccgctgt cgagcaagcg      840
ccctcgtgcg cgcaaccctt gtggtgcctg cccgcagagc cgggcataaa ggcgagcacc      900
```

-continued

```
acacccgaac cagtccaatt tgctttctgc attcactcac caacttttac atccacacat    960
cgtactacca cacctgccca gtcgggtttg atttctattg caaaggtgcg gggggggttgg   1020 cgcactgcgt gggttgtgca gccggccgcc gcggctgtac ccagcgatca ggtagcttgg    1080
gctgtatctt ctcaagcatt accttgtcct gggcgtaggt ttgccgctag caccatggcc    1140
accgcatcca ctttctcggc gttcaatgcc cgctgcggcg acctgcgtcg ctcggcgggc    1200
tccgggcccc ggcgcccagc gaggcccctc cccgtgcgcg ggcgcgccgt ccaggccgcg    1260
gccacccgct tcaagaagga gacgacgacc acccgcgcca cgctgacgtt cgaccccccc    1320
acgaccaact ccgagcgcgc caagcagcgc aagcacacca tcgacccctc ctcccccgac    1380
ttccagccca tcccctcctt cgaggagtgc ttccccaagt ccacgaagga gcacaaggag    1440
gtggtgcacg aggagtccgg ccacgtcctg aaggtgccct tccgccgcgt gcacctgtcc    1500
ggcggcgagc ccgccttcga caactacgac acgtccggcc cccagaacgt caacgcccac    1560
atcggcctgg cgaagctgcg caaggagtgg atcgaccgcc gcgagaagct gggcacgccc    1620
cgctacacgc agatgtacta cgcgaagcag ggcatcatca cggaggagat gctgtactgc    1680
gcgacgcgcg agaagctgga ccccgagttc gtccgctccg aggtcgcgcg gggccgcgcc    1740
atcatcccct ccaacaagaa gcacctggag ctggagccca tgatcgtggg ccgcaagttc    1800
ctggtgaagg tgaacgcgaa catcggcaac tccgccgtgg cctcctccat cgaggaggag    1860
gtctacaagg tgcagtgggc caccatgtgg ggcgccgaca ccatcatgga cctgtccacg    1920
ggccgccaca tccacgagac gcgcgagtgg atcctgcgca actccgcggt ccccgtgggc    1980
accgtcccca tctaccaggc gctggagaag gtggacggca tcgcggagaa cctgaactgg    2040
gaggtgttcc gcgagacgct gatcgagcag gccgagcagg gcgtggacta cttcacgatc    2100
cacgcgggcg tgctgctgcg ctacatcccc ctgaccgcca agcgcatgac gggcatcgtg    2160
tcccgcggcg gctccatcca cgcgaagtgg tgcctggcct accacaagga gaacttcgcc    2220
tacgagcact gggacgacat cctggacatc tgcaaccagt acgacgtcgc cctgtccatc    2280
ggcgacggcc tgcgccccgg ctccatctac gacgccaacg acacggccca gttcgccgag    2340
ctgctgaccc agggcgagct gacgcgccgc gcgtgggaga aggacgtgca ggtgatgaac    2400
gagggccccg gccacgtgcc catgcacaag atccccgaga acatgcagaa gcagctggag    2460
tggtgcaacg aggcgccctt ctacaccctg ggcccctga cgaccgacat cgcgcccggc    2520
tacgaccaca tcacctccgc catcggcgcg gccaacatcg gcgccctggg caccgccctg    2580
ctgtgctacg tgacgcccaa ggagcacctg ggcctgccca accgcgacga cgtgaaggcg    2640
ggcgtcatcg cctacaagat cgccgcccac gcggccgacc tggccaagca gcaccccac    2700 gcccaggcgt gggacgacgc gctgtccaag gcgcgcttcg agttccgctg gatggaccag    2760
ttcgcgctgt ccctggaccc catgacggcg atgtccttcc acgacgagac gctgcccgcg    2820
gacggcgcga aggtcgccca cttctgctcc atgtgcggcc ccaagttctg ctccatgaag    2880
atcacggagg acatccgcaa gtacgccgag gagaacggct acggctccgc cgaggaggcc    2940
atccgccagg gcatggacgc catgtccgag gagttcaaca tcgccaagaa gacgatctcc    3000
ggcgagcagc acgcgaggt cggcggcgag atctacctgc ccgagtccta cgtcaaggcc    3060
gcgcagaagt gatacttat tacgtaacag acgaccttgg caggcgtcgg gtagggaggt   3120
ggtggtgatg gcgtctcgat gccatcgcac gcatccaacg accgtatacg catcgtccaa   3180
tgaccgtcgg tgtcctctct gcctccgttt tgtgagatgt ctcaggcttg gtgcatcctc   3240
gggtggccag ccacgttgcg cgtcgtgctg cttgcctctc ttgcgcctct gtggtactgg   3300
```

-continued

```
aaaatatcat cgaggcccgt tttttttgctc ccatttcctt tccgctacat cttgaaagca    3360
aacgacaaac gaagcagcaa gcaaagagca cgaggacggt gaacaagtct gtcacctgta    3420
tacatctatt tccccgcggg tgcacctact ctctctcctg ccccggcaga gtcagctgcc    3480
ttacgtgacg gatcccgcgt ctcgaacaga gcgcgcagag gaacgctgaa ggtctcgcct    3540
ctgtcgcacc tcagcgcggc atacaccaca ataaccacct gacgaatgcg cttggttctt    3600
cgtccattag cgaagcgtcc ggttcacaca cgtgccacgt tggcgaggtg gcaggtgaca    3660
atgatcggtg gagctgatgg tcgaaacgtt cacagcctag ggatatcggg agcagttgtc    3720
gaccgcccgc gtcccgcagg cagcgatgac gtgtgcgtgg cctgggtgtt tcgtcgaaag    3780
gccagcaacc ctaaatcgca ggcgatccgg agattgggat ctgatccgag tttggaccag    3840
atccgccccg atgcggcacg ggaactgcat cgactcggcg cggaacccag ctttcgtaaa    3900
tgccagattg gtgtccgata cctggatttg ccatcagcga aacaagactt cagcagcgag    3960
cgtatttggc gggcgtgcta ccaggggttgc atacattgcc catttctgtc tggaccgctt    4020
tactggcgca gagggtgagt tgatgggggtt ggcaggcatc gaaacgcgcg tgcatggtgt    4080
gcgtgtctgt tttcggctgc acgaattcaa tagtcggatg ggcgacggta gaattgggtg    4140
tggcgctcgc gtgcatgcct cgccccgtcg ggtgtcatga ccgggactgg aatccccct    4200 cgcgaccatc ttgctaacgc tcccgactct cccgaccgcg cgcaggatag actcttgttc    4260
aaccaatcga caactagtac atatggcttc cgcggcattc accatgtcgg cgtgccccgc    4320
gatgactggc agggcccctg gggcacgtcg ctccggacgg ccagtcgcca cccgcctgag    4380
gggctccacc ttccagtgcc tggtgaactc ccacatcgac ccctgcaacc agaacgtgtc    4440
ctccgcctcc ctgtccttcc tgggcgacaa cggcttcggc tccaacccct tccgctccaa    4500
ccgcggccac cgccgcctgg gccgcgcctc ccactccggc gaggccatgg ccgtggccct    4560
gcagcccgcc caggaggtgg ccaccaagaa gaagcccgcc atcaagcagc gccgcgtggt    4620
ggtgaccggc atgggcgtgg tgacccccct gggccacgag cccgacgtgt tctacaacaa    4680
cctgctggac ggcgtgtccg gcatctccga gatcgagacc ttcgactgca cccagttccc    4740 caccccgcatc gccggcgaga tcaagtcctt ctccaccgac ggctgggtgg ccccccaagct    4800 gtccaagcgc atggacaagt tcatgctgta cctgctgacc gccggcaaga aggccctggc    4860
cgacgccggc atcaccgagg acgtgatgaa ggagctggac aagcgcaagt gcggcgtgct    4920
gatcggctcc ggcatgggcg gcatgaagct gttcaacgac tccatcgagg ccctgcgcgt    4980
gtcctacaag aagatgaacc ccttctgcgt gcccttcgcc accaccaaca tgggctccgc    5040
catgctggcc atggacctgg ctggatgggg ccccaactac tccatctcca ccgcctgcgc    5100
cacctccaac ttctgcatcc tgaacgccgc caaccacatc atccgcggcg aggccgacat    5160
gatgctgtgc ggcggctccg acgccgtgat catccccatc ggcctgggcg gcttcgtggc    5220
ctgccgcgcc ctgtcccagc gcaactccga ccccaccaag gcctcccgcc cctgggactc    5280
caaccgcgac ggcttcgtga tgggcgaggg cgccggcgtg ctgctgctgg aggagctgga    5340
gcacgccaag aagcgcggcg ccaccatcta cgccgagttc ctgggcggct ccttcacctg    5400
cgacgcctac cacatgaccg agccccaccc cgacggcgcc ggcgtgatcc tgtgcatcga    5460
gaaggccctg gccccagtccg gcgtgtcccg cgaggacgtg aactacatca cgcccacgc    5520 cacctccacc cccgccggcg acatcaagga gtaccaggcc ctggcccact gcttcggcca    5580
gaactccgag ctgcgcgtga actccaccaa gtccatgatc ggccacctgc tgggcgccgc    5640
```

-continued

```
cggcggcgtg gaggccgtga ccgtgatcca ggccatccgc accggctgga tccaccccaa      5700
cctgaacctg gaggaccccg acgaggccgt ggacgccaag ttcctggtgg gccccaagaa      5760
ggagcgcctg aacgtgaagg tgggcctgtc caactccttc ggcttcggcg gccacaactc      5820
ctccatcctg ttcgccccct acaacaccat gtacccctac gacgtgcccg actacgcctg      5880
agatatcgga gcgacgagtg tgcgtgcggg gctggcggga gtgggacgcc ctcctcgctc      5940
ctctctgttc tgaacggaac aatcggccac cccgcgctac gcgccacgca tcgagcaacg      6000
aagaaaaccc cccgatgata ggttgcggtg gctgccggga tatagatccg gccgcacatc      6060
aaagggcccc tccgccagag aagaagctcc tttcccagca gactccttct gctgccaaaa      6120
cacttctctg tccacagcaa caccaaagga tgaacagatc aacttgcgtc tccgcgtagc      6180
ttcctcggct agcgtgcttg caacaggtcc ctgcactatt atcttcctgc tttcctctga      6240
attatgcggc aggcgagcgc tcgctctggc gagcgctcct tcgcgccgcc ctcgctgatc      6300
gagtgtacag tcaatgaatg gtgagctcag cgtctgcgtg ttgggagctg gagtcgtggg      6360
cttgacgacg gcgctgcagc tgttgcagga tgtgcctggc gtgcgcgttc acgtcgtggc      6420
tgagaaatat ggcgacgaaa cgttgacggc tggggccggc gggctgtgga tgccatacgc      6480
attgggtacg cggccattgg atgggattga taggcttatg gagggataat agagtttttg      6540
ccggatccaa cgcatgtgga tgcggtatcc cggtgggctg aaagtgtgga aggatagtgc      6600
attggctatt cacatgcact gcccaccccct tttggcagga aatgtgccgg catcgttggt      6660
gcaccgatgg ggaaaatcga cgttcgacca ctacatgaag atttatacgt ctgaagatgc      6720
agcgactgcg ggtgcgaaac ggatgacggt ttggtcgtgt atgtcacagc atgtgctgga      6780
tcttgcgggc taactcccccc tgccacggcc cattgcaggt gtcatgttga ctggagggta      6840
cgacctttcg tccgtcaaat tcccagagga ggacccgctc tgggccgaca ttgtgcccac      6900
tgaagagcgt ttaaaccgcc tctccccgcg cgttggccga ttcattaatg cagctggcac      6960
gacaggtttc ccgactggaa agcgggcagt gagcgcaacg caattaatgt gagttagctc      7020
actcattagg cacccccaggc tttacacttt atgcttccgg ctcgtatgtt gtgtggaatt      7080
gtgagcggat aacaatttca cacaggaaac agctatgacc atgattacgc caagctcgaa      7140
attaaccctc actaaaggga acaaaagctg gccaattcgc cctatagtga gtcgtattac      7200
aattcactgg ccgtcgtttt acaacgtcgt gactgggaaa accctggcgt tacccaactt      7260
aatcgccttg cagcacatcc ccctttcgcc agctggcgta atagcgaaga ggcccgcacc      7320
gatcgccctt cccaacagtt gcgcagcctg aatggcgaat gggacgcgcc ctgtagcggc      7380
gcattaagcg cggcgggtgt ggtggttacg cgcagcgtga ccgctacact tgccagcgcc      7440
ctagcgcccg ctcctttcgc tttcttccct tcctttctcg ccacgttcgc cggctttccc      7500
cgtcaagctc taaatcgggg gctccctta gggttccgat ttagtgcttt acggcacctc      7560 gacccccaaaa aacttgatta gggtgatggt tcacgtagtg ggccatcgcc ctgatagacg      7620
gtttttcgcc ctttgacgtt ggagtccacg ttctttaata gtggactctt gttccaaact      7680
ggaacaacac tcaaccctat ctcggtctat tcttttgatt tataagggat tttgccgatt      7740
tcggcctatt ggttaaaaaa tgagctgatt taacaaaaat ttaacgcgaa ttttaacaaa      7800
atattaacgc ttacaattta ggtggcactt ttcggggaaa tgtgcgcgga acccctattt      7860
gtttattttt ctaaatacat tcaaatatgt atccgctcat gagacaataa ccctgataaa      7920
tgcttcaata atattgaaaa aggaagagta tgagtattca acatttccgt gtcgccctta      7980
ttcccttttt tgcggcattt tgccttcctg tttttgctca cccagaaacg ctggtgaaag      8040
```

```
taaaagatgc tgaagatcag ttgggtgcac gagtgggtta catcgaactg gatctcaaca    8100
gcggtaagat ccttgagagt tttcgccccg aagaacgttt tccaatgatg agcactttta    8160
aagttctgct atgtggcgcg gtattatccc gtattgacgc cgggcaagag caactcggtc    8220
gccgcataca ctattctcag aatgacttgg ttgagtactc accagtcaca gaaaagcatc    8280
ttacggatgg catgacagta agagaattat gcagtgctgc cataaccatg agtgataaca    8340
ctgcggccaa cttacttctg acaacgatcg gaggaccgaa ggagctaacc gcttttttgc    8400
acaacatggg ggatcatgta actcgccttg atcgttggga accggagctg aatgaagcca    8460
taccaaacga cgagcgtgac accacgatgc ctgtagcaat ggcaacaacg ttgcgcaaac    8520
tattaactgg cgaactactt actctagctt cccggcaaca attaatagac tggatggagg    8580
cggataaagt tgcaggacca cttctgcgct cggcccttcc ggctggctgg tttattgctg    8640
ataaatctgg agccggtgag cgtgggtctc gcggtatcat tgcagcactg gggccagatg    8700
gtaagccctc ccgtatcgta gttatctaca cgacggggag tcaggcaact atggatgaac    8760
gaaatagaca gatcgctgag ataggtgcct cactgattaa gcattggtaa ctgtcagacc    8820
aagtttactc atatatactt tagattgatt taaaacttca tttttaattt aaaaggatct    8880
aggtgaagat cctttttgat aatctcatga ccaaaatccc ttaacgtgag ttttcgttcc    8940
actgagcgtc agacccgta gaaaagatca aaggatcttc ttgagatcct tttttttctgc     9000 gcgtaatctg ctgcttgcaa acaaaaaaac caccgctacc agcggtggtt tgtttgccgg    9060
atcaagagct accaactctt tttccgaagg taactggctt cagcagagcg cagataccaa    9120
atactgtcct tctagtgtag ccgtagttag gccaccactt caagaactct gtagcaccgc    9180
ctacatacct cgctctgcta atcctgttac cagtggctgc tgccagtggc gataagtcgt    9240
gtcttaccgg gttggactca agacgatagt taccggataa ggcgcagcgg tcgggctgaa    9300
cggggggttc gtgcacacag cccagcttgg agcgaacgac ctacaccgaa ctgagatacc    9360
tacagcgtga gctatgagaa agcgccacgc ttcccgaagg gagaaaggcg gacaggtatc    9420
cggtaagcgg cagggtcgga acaggagagc gcacgaggga gcttccaggg ggaaacgcct    9480
ggtatcttta tagtcctgtc gggtttcgcc acctctgact tgagcgtcga tttttgtgat    9540
gctcgtcagg ggggcggagc ctatggaaaa acgccagcaa cgcggccttt ttacggttcc    9600
tggccttttg ctggcctttt gctcacatgt tctttcctgc gttatcccct gattctgtgg    9660
ataaccgtat taccgccttt gagtgagctg ataccgctcg ccgcagccga acgaccgagc    9720
gcagcgagtc agtgagcgag ga                                             9742
```

```
<210> SEQ ID NO 3
<211> LENGTH: 532
<212> TYPE: PRT
<213> ORGANISM: Artificial Sequence
<220> FEATURE:
<223> OTHER INFORMATION: synthetic

<400> SEQUENCE: 3

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Val Asn Ser His Ile Asp Pro Cys
        35                  40                  45

Asn Gln Asn Val Ser Ser Ala Ser Leu Ser Phe Leu Gly Asp Asn Gly
```

-continued

```
            50                  55                  60

Phe Gly Ser Asn Pro Phe Arg Ser Asn Arg Gly His Arg Arg Leu Gly
65                  70                  75                  80

Arg Ala Ser His Ser Gly Glu Ala Met Ala Val Ala Leu Gln Pro Ala
                85                  90                  95

Gln Glu Val Ala Thr Lys Lys Lys Pro Ala Ile Lys Gln Arg Arg Val
                100                 105                 110

Val Val Thr Gly Met Gly Val Val Thr Pro Leu Gly His Glu Pro Asp
            115                 120                 125

Val Phe Tyr Asn Asn Leu Leu Asp Gly Val Ser Gly Ile Ser Glu Ile
        130                 135                 140

Glu Thr Phe Asp Cys Thr Gln Phe Pro Thr Arg Ile Ala Gly Glu Ile
145                 150                 155                 160

Lys Ser Phe Ser Thr Asp Gly Trp Val Ala Pro Lys Leu Ser Lys Arg
                165                 170                 175

Met Asp Lys Phe Met Leu Tyr Leu Leu Thr Ala Gly Lys Lys Ala Leu
                180                 185                 190

Ala Asp Ala Gly Ile Thr Glu Asp Val Met Lys Glu Leu Asp Lys Arg
            195                 200                 205

Lys Cys Gly Val Leu Ile Gly Ser Gly Met Gly Gly Met Lys Leu Phe
        210                 215                 220

Asn Asp Ser Ile Glu Ala Leu Arg Val Ser Tyr Lys Lys Met Asn Pro
225                 230                 235                 240

Phe Cys Val Pro Phe Ala Thr Thr Asn Met Gly Ser Ala Met Leu Ala
                245                 250                 255

Met Asp Leu Gly Trp Met Gly Pro Asn Tyr Ser Ile Ser Thr Ala Cys
                260                 265                 270

Ala Thr Ser Asn Phe Cys Ile Leu Asn Ala Ala Asn His Ile Ile Arg
            275                 280                 285

Gly Glu Ala Asp Met Met Leu Cys Gly Gly Ser Asp Ala Val Ile Ile
        290                 295                 300

Pro Ile Gly Leu Gly Gly Phe Val Ala Cys Arg Ala Leu Ser Gln Arg
305                 310                 315                 320

Asn Ser Asp Pro Thr Lys Ala Ser Arg Pro Trp Asp Ser Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
            355                 360                 365

Gly Ser Phe Thr Cys Asp Ala Tyr His Met Thr Glu Pro His Pro Asp
        370                 375                 380

Gly Ala Gly Val Ile Leu Cys Ile Glu Lys Ala Leu Ala Gln Ser Gly
385                 390                 395                 400

Val Ser Arg Glu Asp Val Asn Tyr Ile Asn Ala His Ala Thr Ser Thr
                405                 410                 415

Pro Ala Gly Asp Ile Lys Glu Tyr Gln Ala Leu Ala His Cys Phe Gly
                420                 425                 430

Gln Asn Ser Glu Leu Arg Val Asn Ser Thr Lys Ser Met Ile Gly His
            435                 440                 445

Leu Leu Gly Ala Ala Gly Gly Val Glu Ala Val Thr Val Ile Gln Ala
        450                 455                 460

Ile Arg Thr Gly Trp Ile His Pro Asn Leu Asn Leu Glu Asp Pro Asp
465                 470                 475                 480
```

-continued

```
Glu Ala Val Asp Ala Lys Phe Leu Val Gly Pro Lys Lys Glu Arg Leu
            485             490             495

Asn Val Lys Val Gly Leu Ser Asn Ser Phe Gly Phe Gly Gly His Asn
            500             505             510

Ser Ser Ile Leu Phe Ala Pro Tyr Asn Thr Met Tyr Pro Tyr Asp Val
            515             520             525

Pro Asp Tyr Ala
    530

<210> SEQ ID NO 4
<211> LENGTH: 532
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (146)..(146)
<223> OTHER INFORMATION: wherein Xaa is A,C,D,E,F,G,H,I,K,L,M,N,P,Q,R,S,
     V,W, or Y.

<400> SEQUENCE: 4

Met Ala Ser Ala Ala Phe Thr Met Ser Ala Cys Pro Ala Met Thr Gly
1               5               10              15

Arg Ala Pro Gly Ala Arg Arg Ser Gly Arg Pro Val Ala Thr Arg Leu
            20              25              30

Arg Gly Ser Thr Phe Gln Cys Leu Val Asn Ser His Ile Asp Pro Cys
            35              40              45

Asn Gln Asn Val Ser Ser Ala Ser Leu Ser Phe Leu Gly Asp Asn Gly
    50              55              60

Phe Gly Ser Asn Pro Phe Arg Ser Asn Arg Gly His Arg Arg Leu Gly
65              70              75              80

Arg Ala Ser His Ser Gly Glu Ala Met Ala Val Ala Leu Gln Pro Ala
            85              90              95

Gln Glu Val Ala Thr Lys Lys Lys Pro Ala Ile Lys Gln Arg Arg Val
            100             105             110

Val Val Thr Gly Met Gly Val Val Thr Pro Leu Gly His Glu Pro Asp
            115             120             125

Val Phe Tyr Asn Asn Leu Leu Asp Gly Val Ser Gly Ile Ser Glu Ile
    130             135             140

Glu Xaa Phe Asp Cys Thr Gln Phe Pro Thr Arg Ile Ala Gly Glu Ile
145             150             155             160

Lys Ser Phe Ser Thr Asp Gly Trp Val Ala Pro Lys Leu Ser Lys Arg
            165             170             175

Met Asp Lys Phe Met Leu Tyr Leu Leu Thr Ala Gly Lys Lys Ala Leu
            180             185             190

Ala Asp Ala Gly Ile Thr Glu Asp Val Met Lys Glu Leu Asp Lys Arg
            195             200             205

Lys Cys Gly Val Leu Ile Gly Ser Gly Met Gly Gly Met Lys Leu Phe
    210             215             220

Asn Asp Ser Ile Glu Ala Leu Arg Val Ser Tyr Lys Lys Met Asn Pro
225             230             235             240

Phe Cys Val Pro Phe Ala Thr Thr Asn Met Gly Ser Ala Met Leu Ala
            245             250             255

Met Asp Leu Gly Trp Met Gly Pro Asn Tyr Ser Ile Ser Thr Ala Cys
            260             265             270
```

```
Ala Thr Ser Asn Phe Cys Ile Leu Asn Ala Ala Asn His Ile Ile Arg
        275                 280                 285

Gly Glu Ala Asp Met Met Leu Cys Gly Gly Ser Asp Ala Val Ile Ile
    290                 295                 300

Pro Ile Gly Leu Gly Gly Phe Val Ala Cys Arg Ala Leu Ser Gln Arg
305                 310                 315                 320

Asn Ser Asp Pro Thr Lys Ala Ser Arg Pro Trp Asp Ser Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
        355                 360                 365

Gly Ser Phe Thr Cys Asp Ala Tyr His Met Thr Glu Pro His Pro Asp
    370                 375                 380

Gly Ala Gly Val Ile Leu Cys Ile Glu Lys Ala Leu Ala Gln Ser Gly
385                 390                 395                 400

Val Ser Arg Glu Asp Val Asn Tyr Ile Asn Ala His Ala Thr Ser Thr
                405                 410                 415

Pro Ala Gly Asp Ile Lys Glu Tyr Gln Ala Leu Ala His Cys Phe Gly
            420                 425                 430

Gln Asn Ser Glu Leu Arg Val Asn Ser Thr Lys Ser Met Ile Gly His
        435                 440                 445

Leu Leu Gly Ala Ala Gly Gly Val Glu Ala Val Thr Val Ile Gln Ala
    450                 455                 460

Ile Arg Thr Gly Trp Ile His Pro Asn Leu Asn Leu Glu Asp Pro Asp
465                 470                 475                 480

Glu Ala Val Asp Ala Lys Phe Leu Val Gly Pro Lys Lys Glu Arg Leu
            485                 490                 495

Asn Val Lys Val Gly Leu Ser Asn Ser Phe Gly Phe Gly Gly His Asn
                500                 505                 510

Ser Ser Ile Leu Phe Ala Pro Tyr Asn Thr Met Tyr Pro Tyr Asp Val
            515                 520                 525

Pro Asp Tyr Ala
    530
```

```
<210> SEQ ID NO 5
<211> LENGTH: 400
<212> TYPE: PRT
<213> ORGANISM: Artificial Sequence
<220> FEATURE:
<223> OTHER INFORMATION: synthetic

<400> SEQUENCE: 5

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
                20                  25                  30

Pro Val Arg Ala Ala Ile Asn Ala Ser Ala His Pro Lys Ala Asn Gly
            35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Val Asp Ser Val Gly Leu Lys Ser Val Val Leu Asp Gly
            85                  90                  95
```

-continued

```
Leu Val Ser Arg Gln Ile Phe Ser Ile Arg Ser Tyr Glu Ile Gly Ala
             100                 105                 110

Asp Arg Thr Ala Ser Ile Glu Thr Leu Met Asn His Leu Gln Glu Thr
             115                 120                 125

Ser Ile Asn His Cys Lys Ser Leu Gly Leu Leu Asn Asp Gly Phe Gly
             130                 135                 140

Arg Thr Pro Gly Met Cys Lys Asn Asp Leu Ile Trp Val Leu Thr Lys
145                 150                 155                 160

Met Gln Ile Met Val Asn Arg Tyr Pro Thr Trp Gly Asp Thr Val Glu
                 165                 170                 175

Ile Asn Thr Trp Phe Ser His Ser Gly Lys Ile Gly Met Ala Ser Asp
                 180                 185                 190

Trp Leu Ile Thr Asp Cys Asn Thr Gly Glu Ile Leu Ile Arg Ala Thr
                 195                 200                 205

Ser Val Trp Ala Met Met Asn Gln Lys Thr Arg Arg Phe Ser Arg Leu
             210                 215                 220

Pro Tyr Glu Val Arg Gln Glu Leu Thr Pro His Tyr Val Asp Ser Pro
225                 230                 235                 240

His Val Ile Glu Asp Asn Asp Arg Lys Leu His Lys Phe Asp Val Lys
                 245                 250                 255

Thr Gly Asp Ser Ile Arg Lys Gly Leu Thr Pro Arg Trp Asn Asp Leu
                 260                 265                 270

Asp Val Asn Gln His Val Ser Asn Val Lys Tyr Ile Gly Trp Ile Leu
                 275                 280                 285

Glu Ser Met Pro Ile Glu Val Leu Glu Thr Gln Glu Leu Cys Ser Leu
             290                 295                 300

Thr Val Glu Tyr Arg Arg Glu Cys Gly Met Asp Ser Val Leu Glu Ser
305                 310                 315                 320

Val Thr Ala Met Asp Pro Ser Glu Asp Glu Gly Arg Ser Gln Tyr Lys
                 325                 330                 335

His Leu Leu Arg Leu Glu Asp Gly Thr Asp Ile Val Lys Gly Arg Thr
                 340                 345                 350

Glu Trp Arg Pro Lys Asn Ala Gly Thr Asn Gly Ala Ile Ser Thr Ala
                 355                 360                 365

Lys Pro Ser Asn Gly Asn Ser Val Ser Met Asp Tyr Lys Asp His Asp
             370                 375                 380

Gly Asp Tyr Lys Asp His Asp Ile Asp Tyr Lys Asp Asp Asp Asp Lys
385                 390                 395                 400

<210> SEQ ID NO 6
<211> LENGTH: 9693
<212> TYPE: DNA
<213> ORGANISM: Artificial Sequence
<220> FEATURE:
<223> OTHER INFORMATION: synthetic

<400> SEQUENCE: 6
agcggaagag cgcccaatgt ttaaacccct caactgcgac gctgggaacc ttctccgggc      60
aggcgatgtg cgtgggtttg cctccttggc acggctctac accgtcgagt acgccatgag     120
gcggtgatgg ctgtgtcggt tgccacttcg tccagagacg gcaagtcgtc catcctctgc     180
gtgtgtggcg cgacgctgca gcagtccctc tgcagcagat gagcgtgact ttggccattt     240
cacgcactcg agtgtacaca atccattttt cttaaagcaa atgactgctg attgaccaga     300
tactgtaacg ctgatttcgc tccagatcgc acagatagcg accatgttgc tgcgtctgaa     360
```

-continued

```
aatctggatt ccgaattcga ccctggcgct ccatccatgc aacagatggc gacacttgtt    420
acaattcctg tcacccatcg gcatggagca ggtccactta gattcccgat cacccacgca    480
catctcgcta atagtcattc gttcgtgtct tcgatcaatc tcaagtgagt gtgcatggat    540
cttggttgac gatgcggtat gggtttgcgc cgctggctgc agggtctgcc caaggcaagc    600
taacccagct cctctccccg acaatactct cgcaggcaaa gccggtcact tgccttccag    660
attgccaata aactcaatta tggcctctgt catgccatcc atgggtctga tgaatggtca    720
cgctcgtgtc ctgaccgttc cccagcctct ggcgtcccct gccccgccca ccagcccacg    780
ccgcgcggca gtcgctgcca aggctgtctc ggaggtaccc tttcttgcgc tatgacactt    840
ccagcaaaag gtagggcggg ctgcgagacg gcttcccggc gctgcatgca acaccgatga    900
tgcttcgacc ccccgaagct ccttcggggc tgcatgggcg ctccgatgcc gctccagggc    960
gagcgctgtt taaatagcca ggcccccgat tgcaaagaca ttatagcgag ctaccaaagc   1020
catattcaaa cacctagatc actaccactt ctacacaggc cactcgagct tgtgatcgca   1080
ctccgctaag ggggcgcctc ttcctcttcg tttcagtcac aacccgcaaa ctctagaata   1140
tcaatgctgc tgcaggcctt cctgttcctg ctggccggct cgccgccaa gatcagcgcc   1200 tccatgacga acgagacgtc cgaccgcccc ctggtgcact tcacccccaa caagggctgg   1260
atgaacgacc ccaacggcct gtggtacgac gagaaggacg ccaagtggca cctgtacttc   1320
cagtacaacc cgaacgacac cgtctggggg acgcccttgt tctggggcca cgccacgtcc   1380
gacgacctga ccaactggga ggaccagccc atcgccatcg ccccgaagcg caacgactcc   1440
ggcgccttct ccggctccat ggtggtggac tacaacaaca cctccggctt cttcaacgac   1500
accatcgacc cgcgccagcg ctgcgtggcc atctggacct acaacacccc ggagtccgag   1560
gagcagtaca tctcctacag cctggacggc ggctacacct tcaccgagta ccagaagaac   1620
cccgtgctgg ccgccaactc cacccagttc cgcgacccga aggtcttctg gtacgagccc   1680
tcccagaagt ggatcatgac cgcggccaag tcccaggact acaagatcga gatctactcc   1740
tccgacgacc tgaagtcctg gaagctggag tccgcgttcg ccaacgaggg cttcctcggc   1800
taccagtacg agtgccccgg cctgatcgag gtccccaccg agcaggaccc cagcaagtcc   1860
tactgggtga tgttcatctc catcaacccc ggcgccccgg ccggcggctc cttcaaccag   1920
tacttcgtcg gcagcttcaa cggcacccac ttcgaggcct cgacaaacca gtcccgcgtg   1980
gtggacttcg gcaaggacta ctacgccctg cagacccttct tcaacaccga cccgacctac   2040
gggagcgccc tggcatcgc gtgggcctcc aactgggagt actccgcctt cgtgcccacc   2100 aaccctggc gctcctccat gtccctcgtg cgcaagttct ccctcaacac cgagtaccag   2160 gccaaccgg agacggagct gatcaacctg aaggccgagc cgatcctgaa catcagcaac   2220
gccggcccct ggagccggtt cgccaccaac accacgttga cgaaggccaa cagctacaac   2280
gtcgacctgt ccaacagcac cggcacccctg gagttcgagc tggtgtacgc cgtcaacacc   2340
acccagacga tctccaagtc cgtgttcgcg gacctctccc tctggttcaa gggcctggag   2400
gaccccgagg agtacctccg catgggcttc gaggtgtccg cgtcctcctt cttcctggac   2460
cgcgggaaca gcaaggtgaa gttcgtgaag gagaacccct acttcaccaa ccgcatgagc   2520
gtgaacaacc agcccttcaa gagcgagaac gacctgtcct actacaaggt gtacggcttg   2580
ctggaccaga acatcctgga gctgtacttc aacgacggcg acgtcgtgtc caccaacacc   2640
tacttcatga ccaccgggaa cgccctgggc tccgtgaaca tgacgacggg ggtggacaac   2700
ctgttctaca tcgacaagtt ccaggtgcgc gaggtcaagt gacaattgac gcccgcgcgg   2760
```

-continued

```
cgcacctgac ctgttctctc gagggcgcct gttctgcctt gcgaaacaag cccctggagc    2820
atgcgtgcat gatcgtctct ggcgccccgc cgcgcggttt gtcgccctcg cgggcgccgc    2880
ggccgcgggg gcgcattgaa attgttgcaa accccacctg acagattgag ggcccaggca    2940
ggaaggcgtt gagatggagg tacaggagtc aagtaactga aagtttttat gataactaac    3000
aacaaagggt cgtttctggc cagcgaatga caagaacaag attccacatt tccgtgtaga    3060
ggcttgccat cgaatgtgag cgggcgggcc gcggacccga caaaaccctt acgacgtggt    3120
aagaaaaacg tggcgggcac tgtccctgta gcctgaagac cagcaggaga cgatcggaag    3180
catcacagca caggatcccg cgtctcgaac agagcgcgca gaggaacgct gaaggtctcg    3240
cctctgtcgc acctcagcgc ggcatacacc acaataacca cctgacgaat gcgcttggtt    3300
cttcgtccat tagcgaagcg tccggttcac acacgtgcca cgttggcgag gtggcaggtg    3360
acaatgatcg gtggagctga tggtcgaaac gttcacagcc tagggattat caaaaacgcc    3420
tgagacactt gcccaggatt gaaactccct gaagggacca ccaggggccc tgagttgttc    3480
cttccccccg tggcgagctg ccagccaggc tgtacctgtg atcggggctg gcgggaaaac    3540
aggcttcgtg tgctcaggtt atgggaggtg caggacagct cattaaacgc caacaatcgc    3600
acaattcatg gcaagctaat cagttatttc ccattaacga gctataattg tcccaaaatt    3660
ctggtctacc gggggtgatc cttcgtgtac gggcccttcc ctcaacccta ggtatgcgca    3720
catgcggtcg ccgcgcaacg cgcgcgaggg ccgagggttt gggacgggcc gtcccgaaat    3780
gcagttgcac ccggatgcgt ggcacctttt ttgcgataat ttatgcaatg gactgctctg    3840
caaaattctg gctctgtcgc caaccctagg atcagcggtg taggatttcg taatcattcg    3900
tcctgatggg gagctaccga ctgccctagt atcagcccga ctgcctgacg ccagcgtcca    3960
cttttgtgca cacattccat tcgtgcccaa gacatttcat tgtggtgcga agcgtcccca    4020
gttacgctca cctgatcccc aacctcctta ttgttctgtc gacagagtgg gcccagaggc    4080
cggtcgcagc cactagtaca tatggcttcc gcggcattca ccatgtcggc gtgccccgcg    4140
atgactggca gggccctgg ggcacgtcgc tccggacggc cagtcgccac ccgcctgagg    4200
ggctccacct tccagtgcct ggtgaactcc cacatcgacc cctgcaacca gaacgtgtcc    4260
tccgcctccc tgtccttcct gggcgacaac ggcttcggct ccaacccctt ccgctccaac    4320
cgcggccacc gccgcctggg ccgcgcctcc cactccggcg aggccatggc cgtggccctg    4380
cagcccgccc aggaggtggc caccaagaag aagcccgcca tcaagcagcg ccgcgtggtg    4440
gtgaccggca tgggcgtggt gaccccgctg ggccacgagc ccgacgtgtt ctacaacaac    4500
ctgctggacg gcgtgtccgg catctccgag atcgagagct cgactgcac ccagttcccc    4560 accgcatcg ccggcgagat caagtccttc tccaccgacg ctgggtggc cccgaagctg    4620 tccaagcgca tggacaagtt catgctgtac ctgctgaccg ccggcaagaa ggccctggcc    4680
gacgccggca tcaccgagga cgtgatgaag gagctggaca agcgcaagtg cggcgtgctg    4740
atcggctccg gcatgggcgg catgaagctg ttcaacgact ccatcgaggc cctgcgcgtg    4800
tcctacaaga agatgaaccc cttctgcgtg cccttcgcca ccaccaacat gggctccgcc    4860
atgctggcca tggacctggg ctggatgggc cccaactact ccatctccac cgcctgcgcc    4920
acctccaact tctgcatcct gaacgccgcc aaccacatca tccgcggcga ggccgacatg    4980
atgctgtgcg gcggctccga cgccgtgatc atccccatcg gctgggcgg cttcgtggcc    5040 tgccgcgccc tgtcccagcg caactccgac cccaccaagg cctcccgccc ctgggactcc    5100
```

-continued

```
aaccgcgacg gcttcgtgat gggcgagggc gccggcgtgc tgctgctgga ggagctggag      5160
cacgccaaga agcgcggcgc caccatctac gccgagttcc tgggcggctc cttcacctgc      5220
gacgcctacc acatgaccga gccgcacccg gacggcgccg gcgtgatcct gtgcatcgag      5280
aaggccctgg cccagtccgg cgtgtcccgc gaggacgtga actacatcaa cgcccacgcc      5340
acctccaccc cggccggcga catcaaggag taccaggccc tggcccactg cttcggccag      5400
aactccgagc tgcgcgtgaa ctccaccaag tccatgatcg gccacctgct gggcgccgcc      5460
ggcggcgtgg aggccgtgac cgtgatccag gccatccgca ccggctggat ccaccccaac      5520
ctgaacctgg aggaccccga cgaggccgtg gacgccaagt cctggtgggg ccccaagaag      5580
gagcgcctga acgtgaaggt gggcctgtcc aactccttcg gcttcggcgg ccacaactcc      5640
tccatcctgt tcgccccgta caacaccatg taccccctacg acgtgcccga ctacgcctga      5700
gatatcggag cgacgagtgt gcgtgcgggg ctggcgggag tgggacgccc tcctcgctcc      5760
tctctgttct gaacggaaca atcggccacc ccgcgctacg cgccacgcat cgagcaacga      5820
agaaaacccc ccgatgatag gttgcggtgg ctgccgggat atagatccgg ccgcacatca      5880
aagggcccct ccgccagaga agaagctcct ttcccagcag actccttctg ctgccaaaac      5940
acttctctgt ccacagcaac accaaaggat gaacagatca acttgcgtct ccgcgtagct      6000
tcctcggcta gcgtgcttgc aacaggtccc tgcactatta tcttcctgct ttcctctgaa      6060
ttatgcggca ggcgagcgct cgctctggcg agcgctcctt cgcgccgccc tcgctgatcg      6120
agtgtacagt caatgaatgg tgagctccag cgccatgcca cgcccttttga tggcttcaag      6180 tacgattacg gtgttggatt gtgtgtttgt tgcgtagtgt gcatggttta gaataataca      6240
cttgatttct tgctcacggc aatctcggct tgtccgcagg ttcaaccccca tttcggagtc      6300 tcaggtcagc cgcgcaatga ccagccgcta cttcaaggac ttgcacgaca acgccgaggt      6360
gagctatgtt taggacttga ttggaaattg tcgtcgacgc atattcgcgc tccgcgacag      6420
cacccaagca aaatgtcaag tgcgttccga tttgcgtccg caggtcgatg ttgtgatcgt      6480
cggcgccgga tccgccggtc tgtcctgcgc ttacgagctg accaagcacc ctgacgtccg      6540
ggtacgcgag ctgagattcg attagacata aattgaagat taaacccgta gaaaaatttg      6600
atggtcgcga aactgtgctc gattgcaaga aattgatcgt cctccactcc gcaggtcgcc      6660
atcatcgagc agggcgttgc tcccggcggc ggcgcctggc tggggggaca gctgttctcg      6720
gccatgtgtg tacgtagaag gatgaatttc agctggtttt cgttgcacag ctgtttgtgc      6780
atgatttgtt tcagactatt gttgaatgtt tttagatttc ttaggatgca tgatttgtct      6840
gcatgcgact gaagagcgtt taaaccgcct ctccccgcgc gttggccgat tcattaatgc      6900
agctggcacg acaggtttcc cgactggaaa gcgggcagtg agcgcaacgc aattaatgtg      6960
agttagctca ctcattaggc accccaggct ttacacttta tgcttccggc tcgtatgttg      7020
tgtggaattg tgagcggata acaatttcac acaggaaaca gctatgacca tgattacgcc      7080
aagctcgaaa ttaaccctca ctaaagggaa caaaagctgg caattcgccc tatagtgagt      7140
cgtattacgc gcgctcactg gccgtcgttt tacaacgtcg tgactgggaa aaccctggcg      7200
ttacccaact taatcgcctt gcagcacatc cccctttcgc cagctggcgt aatagcgaag      7260
aggcccgcac cgatcgccct tcccaacagt tgcgcagcct gaatggcgaa tgggacgcgc      7320
cctgtagcgg cgcattaagc gcggcgggtg tggtggttac gcgcagcgtg accgctacac      7380
ttgccagcgc cctagcgccc gctcctttcg ctttcttccc ttcctttctc gccacgttcg      7440
ccggctttcc ccgtcaagct ctaaatcggg ggctcccttt agggttccga tttagtgctt      7500
```

```
tacggcacct cgaccccaaa aaacttgatt agggtgatgg ttcacgtagt gggccatcgc   7560
cctgatagac ggttttttcgc cctttgacgt tggagtccac gttctttaat agtggactct   7620
tgttccaaac tggaacaaca ctcaaccta tctcggtcta ttcttttgat ttataaggga   7680
ttttgccgat ttcggcctat tggttaaaaa atgagctgat ttaacaaaaa tttaacgcga   7740
attttaacaa aatattaacg cttacaattt aggtggcact tttcggggaa atgtgcgcgg   7800 aaccccttatt tgtttatttt tctaaataca ttcaaatatg tatccgctca tgagacaata   7860
accctgataa atgcttcaat aatattgaaa aaggaagagt atgagtattc aacatttccg   7920
tgtcgccctt attcccttttt ttgcggcatt ttgccttcct gttttttgctc acccagaaac   7980 gctggtgaaa gtaaaagatg ctgaagatca gttgggtgca cgagtgggtt acatcgaact   8040
ggatctcaac agcggtaaga tccttgagag ttttcgcccc gaagaacgtt ttccaatgat   8100
gagcactttt aaagttctgc tatgtggcgc ggtattatcc cgtattgacg ccgggcaaga   8160
gcaactcggt cgccgcatac actattctca gaatgacttg gttgagtact caccagtcac   8220
agaaaagcat cttacggatg gcatgacagt aagagaatta tgcagtgctg ccataaccat   8280
gagtgataac actgcggcca acttacttct gacaacgatc ggaggaccga aggagctaac   8340
cgcttttttg cacaacatgg gggatcatgt aactcgcctt gatcgttggg aaccggagct   8400
gaatgaagcc ataccaaacg acgagcgtga caccacgatg cctgtagcaa tggcaacaac   8460
gttgcgcaaa ctattaactg gcgaactact tactctagct tcccggcaac aattaataga   8520
ctggatggag gcggataaag ttgcaggacc acttctgcgc tcggcccttc cggctggctg   8580
gtttattgct gataaatctg gagccggtga gcgtgggtct cgcggtatca ttgcagcact   8640
ggggccagat ggtaagccct cccgtatcgt agttatctac acgacgggga gtcaggcaac   8700
tatggatgaa cgaaatagac agatcgctga gataggtgcc tcactgatta agcattggta   8760
actgtcagac caagtttact catatatact ttagattgat ttaaaacttc attttttaatt   8820 taaaaggatc taggtgaaga tcctttttga taatctcatg accaaaatcc cttaacgtga   8880
gttttcgttc cactgagcgt cagaccccgt agaaaagatc aaaggatctt cttgagatcc   8940 ttttttttctg cgcgtaatct gctgcttgca aacaaaaaaa ccaccgctac cagcggtggt   9000
ttgtttgccg gatcaagagc taccaactct ttttccgaag gtaactggct tcagcagagc   9060
gcagatacca aatactgtcc ttctagtgta gccgtagtta ggccaccact tcaagaactc   9120
tgtagcaccg cctacatacc tcgctctgct aatcctgtta ccagtggctg ctgccagtgg   9180
cgataagtcg tgtcttaccg ggttggactc aagacgatag ttaccggata aggcgcagcg   9240
gtcgggctga acggggggtt cgtgcacaca gcccagcttg gagcgaacga cctacaccga   9300
actgagatac ctacagcgtg agctatgaga aagcgccacg cttcccgaag ggagaaaggc   9360
ggacaggtat ccggtaagcg gcagggtcgg aacaggagag cgcacgaggg agcttccagg   9420
gggaaacgcc tggtatcttt atagtcctgt cgggtttcgc cacctctgac ttgagcgtcg   9480 attttttgtga tgctcgtcag ggggcggag cctatggaaa aacgccagca acgcggcctt   9540
tttacggttc ctggcctttt gctggccttt tgctcacatg ttctttcctg cgttatcccc   9600
tgattctgtg ataaccgta ttaccgcctt tgagtgagct gataccgctc gccgcagccg   9660
aacgaccgag cgcagcgagt cagtgagcga gga                                9693
```

<210> SEQ ID NO 7
<211> LENGTH: 1599
<212> TYPE: DNA

-continued

```
<213> ORGANISM: Artificial Sequence
<220> FEATURE:
<223> OTHER INFORMATION: synthetic

<400> SEQUENCE: 7
atggcttccg cggcattcac catgtcggcg tgccccgcga tgactggcag ggcccctggg      60
gcacgtcgct ccggacggcc agtcgccacc cgcctgaggg gctccacctt ccagtgcctg     120
gtgaactccc acatcgaccc ctgcaaccag aacgtgtcct ccgcctccct gtccttcctg     180
ggcgacaacg gcttcggctc caaccccttc cgctccaacc gcggccaccg ccgcctgggc     240
cgcgcctccc actccggcga ggccatggcc gtggccctgc agcccgccca ggaggtggcc     300
accaagaaga agcccgccat caagcagcgc cgcgtggtgg tgaccggcat gggcgtggtg     360
accccgctgg gccacgagcc cgacgtgttc tacaacaacc tgctggacgg cgtgtccggc     420
atctccgaga tcgagacctt cgactgcacc cagttcccca cccgcatcgc cggcgagatc     480
aagtccttct ccaccgacgg ctgggtggcc ccgaagctgt ccaagcgcat ggacaagttc     540
atgctgtacc tgctgaccgc cggcaagaag gccctggccg acgccggcat caccgaggac     600
gtgatgaagg agctggacaa cgcaagtgc ggcgtgctga tcggctccgg catgggcggc     660
atgaagctgt tcaacgactc catcgaggcc ctgcgcgtgt cctacaagaa gatgaacccc     720
ttctgcgtgc ccttcgccac caccaacatg ggctccgcca tgctggccat ggacctgggc     780
tggatgggcc ccaactactc catctccacc gcctgcgcca cctccaactt ctgcatcctg     840
aacgccgcca accacatcat ccgcggcgag gccgacatga tgctgtgcgg cggctccgac     900
gccgtgatca tccccatcgg cctgggcggc ttcgtggcct gccgcgccct gtcccagcgc     960
aactccgacc ccaccaaggc ctcccgcccc tgggactcca accgcgacgg cttcgtgatg    1020
ggcgagggcg ccggcgtgct gctgctggag gagctggagc acgccaagaa gcgcggcgcc    1080
accatctacg ccgagttcct gggcggctcc ttcacctgcg acgcctacca catgaccgag    1140
ccgcacccgg acggcgccgg cgtgatcctg tgcatcgaga aggccctggc ccagtccggc    1200
gtgtcccgcg aggacgtgaa ctacatcaac gcccacgcca cctccacccc ggccggcgac    1260
atcaaggagt accaggccct ggcccactgc ttcggccaga actccgagct gcgcgtgaac    1320
tccaccaagt ccatgatcgg ccacctgctg ggcgccgccg gcggcgtgga ggccgtgacc    1380
gtgatccagg ccatccgcac cggctggatc cacccccaacc tgaacctgga ggaccccgac    1440
gaggccgtgg acgccaagtt cctggtgggc cccaagaagg agcgcctgaa cgtgaaggtg    1500
ggcctgtcca actccttcgg cttcggcggc cacaactcct ccatcctgtt cgccccgtac    1560
aacaccatgt acccctacga cgtgcccgac tacgcctga               1599

<210> SEQ ID NO 8
<211> LENGTH: 9520
<212> TYPE: DNA
<213> ORGANISM: Artificial Sequence
<220> FEATURE:
<223> OTHER INFORMATION: synthetic

<400> SEQUENCE: 8
gatcttcttg agatcctttt tttctgcgcg taatctgctg cttgcaaaca aaaaaaccac      60
cgctaccagc ggtggtttgt ttgccggatc aagagctacc aactcttttt ccgaaggtaa     120
ctggcttcag cagagcgcag ataccaaata ctgtccttct agtgtagccg tagttaggcc     180
accacttcaa gaactctgta gcaccgccta cataccctcgc tctgctaatc ctgttaccag     240
tggctgctgc cagtggcgat aagtcgtgtc ttaccgggtt ggactcaaga cgatagttac     300
```

-continued

```
cggataaggc gcagcggtcg ggctgaacgg ggggttcgtg cacacagccc agcttggagc    360
gaacgaccta caccgaactg agatacctac agcgtgagct atgagaaagc gccacgcttc    420
ccgaagggag aaaggcggac aggtatccgg taagcggcag ggtcggaaca ggagagcgca    480
cgagggagct tccaggggga aacgcctggt atctttatag tcctgtcggg tttcgccacc    540
tctgacttga gcgtcgattt ttgtgatgct cgtcagggg gcggagccta tggaaaaacg    600
ccagcaacgc ggccttttta cggttcctgg ccttttgctg gccttttgct cacatgttct    660
ttcctgcgtt atcccctgat tctgtggata accgtattac cgcctttgag tgagctgata    720
ccgctcgccg cagccgaacg accgagcgca gcgagtcagt gagcgaggaa gcggaagagc    780
gcccaatgtt taaacagccc gcaccctcgt tgatctggga gccctgcgca gcccccttaaa    840 tcatctcagt caggtttctg tgttcaactg agcctaaagg gctttcgtca tgcgcacgag    900
cacacgtata tcggccacgc agtttctcaa aagcggtaga acagttcgcg agccctcgta    960
ggtcgaaaac ttgcgccagt actattaaat taaattaatt gatcgaacga gacgcgaaac   1020
ttttgcagaa tgccaccgag tttgcccaga gaatgggagt ggcgccattc accatccgcc   1080
tgtgcccggc ttgattcgcc gagacgatgg acggcgagac cagggagcgg cttgcgagcc   1140
ccgagccggt agcaggaaca atgatcgaca atcttcctgt ccaattactg gcaaccatta   1200
gaaagagccg gagcgcgttg aaagtctgca atcgagtaat ttttcgatac gtcgggcctg   1260
ctgaacccta aggctccgga ctttgtttaa ggcgatccaa gatgcacgcg gccccaggca   1320
cgtatctcaa gcacaaaccc cagccttagt ttcgagactt tgggagatag cgaccgatat   1380
ctagtttggc attttgtata ttaattacct caagcaatgg agcgctctga tgcggtgcag   1440
cgtcggctgc agcacctggc agtggcgcta gggtcgccct atcgctcgga acctggtcag   1500
ctggctcccg cctcctgctc agcctcttcc ggtaccccgc tcccgtctgg tcctcacgtt   1560
cgtgtacggc ctggatcccg gaaagggcgg atgcacgtgg tgttgccccg ccattggcgc   1620
ccacgtttca aagtccccgg ccagaaatgc acaggaccgg cccggctcgc acaggccatg   1680
acgaatgccc agatttcgac agcaaaacaa tctggaataa tcgcaaccat tcgcgttttg   1740
aacgaaacga aaagacgctg tttagcacgt ttccgatatc gtgggggccg aagcatgatt   1800 gggggggagga aagcgtggcc ccaaggtagc ccattctgtg ccacgcgccg acgaggacca   1860
atccccggca tcagccttca tcgacggctg cgccgcacat ataaagccgg acgccttccc   1920
gacacgttca aacagtttta tttcctccac ttcctgaatc aaacaaatct tcaaggaaga   1980
tcctgctctt gagcagctag caccatggcc accgcatcca cttttctcggc gttcaatgcc   2040 cgctgcggcg acctgcgtcg ctcggcgggc tccgggcccc ggcgccagc gaggcccctc   2100 cccgtgcgcg ggcgcgcccg cgccacgctg acgttcgacc cccccacgac caactccgag   2160
cgcgccaagc agcgcaagca caccatcgac ccctcctccc ccgacttcca gcccatcccc   2220
tccttcgagg agtgcttccc caagtccacg aaggagcaca aggaggtggt gcacgaggag   2280
tccggccacg tcctgaaggt gcccttccgc cgcgtgcacc tgtccggcgg cgagcccgcc   2340
ttcgacaact acgacacgtc cggccccccag aacgtcaacg cccacatcgg cctggcgaag   2400
ctgcgcaagg agtggatcga ccgccgcgag aagctgggca cgcccccgcta cacgcagatg   2460 tactacgcga agcagggcat catcacggag gagatgctgt actgcgcgac gcgcgagaag   2520
ctggaccccg agttcgtccg ctccgaggtc gcgcggggcc gcgccatcat ccctccaac   2580 aagaagcacc tggagctgga gcccatgatc gtgggccgca agttcctggt gaaggtgaac   2640
```

-continued

```
gcgaacatcg gcaactccgc cgtggcctcc tccatcgagg aggaggtcta caaggtgcag    2700
tgggccacca tgtggggcgc cgacaccatc atggacctgt ccacgggccg ccacatccac    2760
gagacgcgcg agtggatcct gcgcaactcc gcggtccccg tgggcaccgt ccccatctac    2820
caggcgctgg agaaggtgga cggcatcgcg gagaacctga actggaggt gttccgcgag     2880 acgctgatcg agcaggccga gcagggcgtg gactacttca cgatccacgc gggcgtgctg    2940
ctgcgctaca tccccctgac cgccaagcgc atgacgggca tcgtgtcccg cggcggctcc    3000
atccacgcga agtggtgcct ggcctaccac aaggagaact tcgcctacga gcactgggac    3060
gacatcctgg acatctgcaa ccagtacgac gtcgccctgt ccatcggcga cggcctgcgc    3120
cccggctcca tctacgacgc caacgacacg gcccagttcg ccgagctgct gacccagggc    3180
gagctgacgc gccgcgcgtg ggagaaggac gtgcaggtga tgaacgaggg ccccggccac    3240
gtgcccatgc acaagatccc cgagaacatg cagaagcagc tggagtggtg caacgaggcg    3300
cccttctaca ccctgggccc cctgacgacc gacatcgcgc ccggctacga ccacatcacc    3360
tccgccatcg gcgcggccaa catcggcgcc ctgggcaccg ccctgctgtg ctacgtgacg    3420
cccaaggagc acctgggcct gcccaaccgc gacgacgtga aggcgggcgt catcgcctac    3480
aagatcgccg cccacgcggc cgacctggcc aagcagcacc cccacgccca ggcgtgggac    3540
gacgcgctgt ccaaggcgcg cttcgagttc cgctggatgg accagttcgc gctgtccctg    3600
gaccccatga cggcgatgtc cttccacgac gagacgctgc ccgcggacgg cgcgaaggtc    3660
gcccacttct gctccatgtg cggccccaag ttctgctcca tgaagatcac ggaggacatc    3720
cgcaagtacg ccgaggagaa cggctacggc tccgccgagg aggccatccg ccagggcatg    3780
gacgccatgt ccgaggagtt caacatcgcc aagaagacga tctccggcga gcagcacggc    3840
gaggtcggcg gcgagatcta cctgcccgag tcctacgtca aggccgcgca gaagtgatac    3900
cttattacgt aacagacgac cttggcaggc gtcgggtagg gaggtggtgg tgatggcgtc    3960
tcgatgccat cgcacgcatc caacgaccgt atacgcatcg tccaatgacc gtcggtgtcc    4020
tctctgcctc cgttttgtga gatgtctcag gcttggtgca tcctcgggtg gccagccacg    4080
ttgcgcgtcg tgctgcttgc ctctcttgcg cctctgtggt actggaaaat atcatcgagg    4140
cccgtttttt tgctcccatt tcctttccgc tacatcttga aagcaaacga caaacgaagc    4200
agcaagcaaa gagcacgagg acggtgaaca agtctgtcac ctgtatacat ctatttcccc    4260
gcgggtgcac ctactctctc tcctgccccg gcagagtcag ctgccttacg tgacggatcc    4320
cgcgtctcga acagagcgcg cagaggaacg ctgaaggtct cgcctctgtc gcacctcagc    4380
gcggcataca ccacaataac cacctgacga atgcgcttgg ttcttcgtcc attagcgaag    4440
cgtccggttc acacacgtgc cacgttggcg aggtggcagg tgacaatgat cggtggagct    4500
gatggtcgaa acgttcacag cctagggata tcatcaaaaa cgcctgagac acttgcccag    4560
gattgaaact ccctgaaggg accaccaggg gccctgagtt gttccttccc cccgtggcga    4620
gctgccagcc aggctgtacc tgtgatcggg gctggcggga aaacaggctt cgtgtgctca    4680
ggttatggga ggtgcaggac agctcattaa acgccaacaa tcgcacaatt catggcaagc    4740
taatcagtta tttcccatta acgagctata attgtcccaa aattctggtc taccgggggt    4800
gatccttcgt gtacgggccc ttccctcaac cctaggtatg cgcacatgcg gtcgccgcgc    4860
aacgcgcgcg agggccgagg gtttgggacg ggccgtcccg aaatgcagtt gcacccggat    4920
gcgtggcacc tttttttgcga taatttatgc aatggactgc tctgcaaaat tctggctctg    4980
tcgccaaccc taggatcagc ggtgtaggat ttcgtaatca ttcgtcctga tggggagcta    5040
```

-continued

```
ccgactgccc  tagtatcagc  ccgactgcct  gacgccagcg  tccacttttg  tgcacacatt  5100
ccattcgtgc  ccaagacatt  tcattgtggt  gcgaagcgtc  cccagttacg  ctcacctgat  5160
ccccaacctc  cttattgttc  tgtcgacaga  gtgggcccag  aggccggtcg  cagccactag  5220
taacaatggc  caccgcctcc  accttctccg  ccttcaacgc  ccgctgcggc  gacctgcgcc  5280
gctccgccgg  ctccggcccc  cgccgccccg  cccgccccct  gcccgtgcgc  gccgccatca  5340
acgcctccgc  ccaccccaag  gccaacggct  ccgccgtgaa  cctgaagtcc  ggctccctga  5400
acacccagga  ggacacctcc  tcctctccgc  ctccccgcgc  cttcctgaac  cagctgcccg  5460
actggtccat  gctggtggac  tccgtgggcc  tgaagtccgt  ggtgctggac  ggcctggtgt  5520
cccgccagat  cttctccatc  cgctcctacg  agatcggcgc  cgaccgcacc  gcctccatcg  5580
agaccctgat  gaaccacctg  caggagacct  ccatcaacca  ctgcaagtcc  ctgggcctgc  5640
tgaacgacgg  cttcggccgc  acccccggca  tgtgcaagaa  cgacctgatc  tgggtgctga  5700
ccaagatgca  gatcatggtg  aaccgctacc  ccacctgggg  cgacaccgtg  gagatcaaca  5760
cctggttctc  ccactccggc  aagatcggca  tggcctccga  ctggctgatc  accgactgca  5820
acaccggcga  gatcctgatc  cgcgccacct  ccgtgtgggc  catgatgaac  cagaagaccc  5880
gccgcttctc  ccgcctgccc  tacgaggtgc  gccaggagct  gacccctcac  tacgtggact  5940
ccccgcacgt  gatcgaggac  aacgaccgca  agctgcacaa  gttcgacgtg  aagaccggcg  6000
actccatccg  caagggcctg  accctcgct  ggaacgacct  ggacgtgaac  cagcacgtgt  6060
ccaacgtgaa  gtacatcggc  tggatcctgg  agtccatgcc  catcgaggtg  ctggagaccc  6120
aggagctgtg  ctccctgacc  gtggagtacc  gccgcgagtg  cggcatggac  tccgtgctgg  6180
agtccgtgac  cgccatggac  ccctccgagg  acgagggccg  ctcccagtac  aagcacctgc  6240
tgcgcctgga  ggacggcacc  gacatcgtga  agggccgcac  cgagtggcgc  cccaagaacg  6300
ccggcaccaa  cggcgccatc  tccaccgcca  agccctccaa  cggcaactcc  gtgtccatgg  6360
actacaagga  ccacgacggc  gactacaagg  accacgacat  cgactacaag  gacgacgacg  6420
acaagtgact  cgagggagcg  acgagtgtgc  gtgcggggct  ggcgggagtg  ggacgccctc  6480
ctcgctcctc  tctgttctga  acggaacaat  cggccacccc  gcgctacgcg  ccacgcatcg  6540
agcaacgaag  aaaaccccccc  gatgataggt  tgcggtggct  gccgggatat  agatccggcc  6600
gcacatcaaa  gggcccctcc  gccagagaag  aagctccttt  cccagcagac  tccttctgct  6660
gccaaaacac  ttctctgtcc  acagcaacac  caaaggatga  acagatcaac  ttgcgtctcc  6720
gcgtagcttc  ctcggctagc  gtgcttgcaa  caggtccctg  cactattatc  ttcctgcttt  6780
cctctgaatt  atgcggcagg  cgagcgctcg  ctctggcgag  cgctccttcg  cgccgccctc  6840
gctgatcgag  tgtacagtca  atgaatggtg  agctcagcgt  ctgcgtgttg  ggagctggag  6900
tcgtgggctt  gacgacggcg  ctgcagctgt  tgcaggatgt  gcctggcgtg  cgcgttcacg  6960
tcgtggctga  gaaatatggc  gacgaaacgt  tgacggctgg  ggccggcggg  ctgtggatgc  7020
catacgcatt  gggtacgcgg  ccattggatg  ggattgatag  gcttatggag  ggataataga  7080 gttttttgccg  gatccaacgc  atgtggatgc  ggtatcccgg  tgggctgaaa  gtgtggaagg  7140
atagtgcatt  ggctattcac  atgcactgcc  cacccctttt  ggcaggaaat  gtgccggcat  7200
cgttggtgca  ccgatgggga  aaatcgacgt  tcgaccacta  catgaagatt  tatacgtctg  7260
aagatgcagc  gactgcgggt  gcgaaacgga  tgacggtttg  gtcgtgtatg  tcacagcatg  7320
tgctggatct  tgcgggctaa  ctccccctgc  cacggcccat  tgcaggtgtc  atgttgactg  7380
```

-continued

```
gagggtacga cctttcgtcc gtcaaattcc cagaggagga cccgctctgg gccgacattg    7440
tgcccactga agagcgttta aaccgcctct ccccgcgcgt tggccgattc attaatgcag    7500
ctggcacgac aggtttcccg actggaaagc gggcagtgag cgcaacgcaa ttaatgtgag    7560
ttagctcact cattaggcac cccaggcttt acactttatg cttccggctc gtatgttgtg    7620
tggaattgtg agcggataac aatttcacac aggaaacagc tatgaccatg attacgccaa    7680
gctcgaaatt aaccctcact aaagggaaca aaagctggcc aattcgccct atagtgagtc    7740
gtattacaat tcactggccg tcgttttaca acgtcgtgac tgggaaaacc ctggcgttac    7800
ccaacttaat cgccttgcag cacatccccc tttcgccagc tggcgtaata gcgaagaggc    7860
ccgcaccgat cgcccttccc aacagttgcg cagcctgaat ggcgaatggg acgcgccctg    7920
tagcggcgca ttaagcgcgg cgggtgtggt ggttacgcgc agcgtgaccg ctacacttgc    7980
cagcgcccta gcgcccgctc ctttcgcttt cttcccttcc tttctcgcca cgttcgccgg    8040
ctttccccgt caagctctaa atcgggggct ccctttaggg ttccgattta gtgctttacg    8100
gcacctcgac cccaaaaaac ttgattaggg tgatggttca cgtagtgggc catcgccctg    8160
atagacggtt tttcgccctt tgacgttgga gtccacgttc tttaatagtg gactcttgtt    8220
ccaaactgga acaacactca accctatctc ggtctattct tttgatttat aagggatttt    8280
gccgatttcg gcctattggt taaaaaatga gctgatttaa caaaaattta acgcgaattt    8340
taacaaaata ttaacgctta caatttaggt ggcacttttc ggggaaatgt gcgcggaacc    8400
cctatttgtt tatttttcta aatacattca aatatgtatc cgctcatgag acaataaccc    8460
tgataaatgc ttcaataata ttgaaaaagg aagagtatga gtattcaaca tttccgtgtc    8520
gcccttattc cctttttttgc ggcattttgc cttcctgttt ttgctcaccc agaaacgctg    8580
gtgaaagtaa aagatgctga agatcagttg ggtgcacgag tgggttacat cgaactggat    8640
ctcaacagcg gtaagatcct tgagagtttt cgccccgaag aacgttttcc aatgatgagc    8700
acttttaaag ttctgctatg tggcgcggta ttatcccgta ttgacgccgg gcaagagcaa    8760
ctcggtcgcc gcatacacta ttctcagaat gacttggttg agtactcacc agtcacagaa    8820
aagcatctta cggatggcat gacagtaaga gaattatgca gtgctgccat aaccatgagt    8880
gataacactg cggccaactt acttctgaca acgatcggag gaccgaagga gctaaccgct    8940
tttttgcaca acatggggga tcatgtaact cgccttgatc gttgggaacc ggagctgaat    9000
gaagccatac caaacgacga gcgtgacacc acgatgcctg tagcaatggc aacaacgttg    9060
cgcaaactat taactggcga actacttact ctagcttccc ggcaacaatt aatagactgg    9120
atggaggcgg ataaagttgc aggaccactt ctgcgctcgg cccttccggc tggctggttt    9180
attgctgata atctggagc cggtgagcgt gggtctcgcg gtatcattgc agcactgggg    9240
ccagatggta gccctcccg tatcgtagtt atctacacga cggggagtca ggcaactatg    9300
gatgaacgaa atagacagat cgctgagata ggtgcctcac tgattaagca ttggtaactg    9360
tcagaccaag tttactcata tatactttag attgatttaa aacttcattt ttaatttaaa    9420
aggatctagg tgaagatcct ttttgataat ctcatgacca aaatccctta acgtgagttt    9480
tcgttccact gagcgtcaga ccccgtagaa aagatcaaag                          9520
```

<210> SEQ ID NO 9
<211> LENGTH: 1599
<212> TYPE: DNA
<213> ORGANISM: Artificial Sequence
<220> FEATURE:
<223> OTHER INFORMATION: synthetic

```
<400> SEQUENCE: 9
atggcttccg cggcattcac catgtcggcg tgccccgcga tgactggcag ggcccctggg      60
gcacgtcgct ccggacggcc agtcgccacc cgcctgaggg gctccacctt ccagtgcctg     120
gtgaactccc acatcgaccc ctgcaaccag aacgtgtcct ccgcctccct gtccttcctg     180
ggcgacaacg gcttcggctc caaccccttc cgctccaacc gcggccaccg ccgcctgggc     240
cgcgcctccc actccggcga ggccatggcc gtggccctgc agcccgccca ggaggtggcc     300
accaagaaga agcccgccat caagcagcgc cgcgtggtgg tgaccggcat gggcgtggtg     360
accccgctgg ccaccgagcc cgacgtgttc tacaacaacc tgctggacgg cgtgtccggc     420
atctccgaga tcgagagctt cgactgcacc cagttcccca cccgcatcgc cggcgagatc     480
aagtccttct ccaccgacgg ctgggtggcc ccgaagctgt ccaagcgcat ggacaagttc     540
atgctgtacc tgctgaccgc cggcaagaag gccctggccg acgccggcat caccgaggac     600
gtgatgaagg agctggacaa cgcaagtgc ggcgtgctga tcggctccgg catgggcggc     660
atgaagctgt tcaacgactc catcgaggcc ctgcgcgtgt cctacaagaa gatgaacccc     720
ttctgcgtgc ccttcgccac caccaacatg ggctccgcca tgctggccat ggacctgggc     780
tggatgggcc ccaactactc catctccacc gcctgcgcca cctccaactt ctgcatcctg     840
aacgccgcca accacatcat ccgcggcgag gccgacatga tgctgtgcgg cggctccgac     900
gccgtgatca tccccatcgg cctgggcggc ttcgtggcct gccgcgccct gtcccagcgc     960
aactccgacc ccaccaaggc ctcccgcccc tgggactcca accgcgacgg cttcgtgatg    1020
ggcgagggcg ccggcgtgct gctgctggag gagctggagc acgccaagaa gcgcggcgcc    1080
accatctacg ccgagttcct gggcggctcc ttcacctgcg acgcctacca catgaccgag    1140
ccgcacccgg acggcgccgg cgtgatcctg tgcatcgaga aggccctggc ccagtccggc    1200
gtgtcccgcg aggacgtgaa ctacatcaac gcccacgcca cctccacccc ggccggcgac    1260
atcaaggagt accaggccct ggcccactgc ttcggccaga actccgagct cgcgtgaac     1320 tccaccaagt ccatgatcgg ccacctgctg ggcgccgccg cggcgtgga ggccgtgacc      1380 gtgatccagg ccatccgcac cggctggatc cacccaacc tgaacctgga ggaccccgac    1440
gaggccgtgg acgccaagtt cctggtgggc cccaagaagg agcgcctgaa cgtgaaggtg    1500
ggcctgtcca actccttcgg cttcggcggc cacaactcct ccatcctgtt cgccccgtac    1560
aacaccatgt accccctacga cgtgcccgac tacgcctga                          1599

<210> SEQ ID NO 10
<211> LENGTH: 38
<212> TYPE: PRT
<213> ORGANISM: Artificial Sequence
<220> FEATURE:
<223> OTHER INFORMATION: synthetic

<400> SEQUENCE: 10

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala
            35

<210> SEQ ID NO 11
<211> LENGTH: 38
```

-continued

```
<212> TYPE: PRT
<213> ORGANISM: Artificial Sequence
<220> FEATURE:
<223> OTHER INFORMATION: synthetic

<400> SEQUENCE: 11

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile
        35

<210> SEQ ID NO 12
<211> LENGTH: 114
<212> TYPE: DNA
<213> ORGANISM: Artificial Sequence
<220> FEATURE:
<223> OTHER INFORMATION: synthetic

<400> SEQUENCE: 12
atggccaccg cctccacctt ctccgccttc aacgcccgct gcggcgacct gcgccgctcc       60
gccggctccg gcccccgccg ccccgcccgc cccctgcccg tgcgcgccgc catc            114

<210> SEQ ID NO 13
<211> LENGTH: 9574
<212> TYPE: DNA
<213> ORGANISM: Artificial Sequence
<220> FEATURE:
<223> OTHER INFORMATION: synthetic

<400> SEQUENCE: 13
agcggaagag cgcccaatgt ttaaacccct caactgcgac gctgggaacc ttctccgggc       60
aggcgatgtg cgtgggtttg cctccttggc acggctctac accgtcgagt acgccatgag      120
gcggtgatgg ctgtgtcggt tgccacttcg tccagagacg gcaagtcgtc catcctctgc      180
gtgtgtggcg cgacgctgca gcagtccctc tgcagcagat gagcgtgact ttggccattt      240
cacgcactcg agtgtacaca atccattttt cttaaagcaa atgactgctg attgaccaga      300
tactgtaacg ctgatttcgc tccagatcgc acagatagcg accatgttgc tgcgtctgaa      360
aatctggatt ccgaattcga ccctggcgct ccatccatgc aacagatggc gacacttgtt      420
acaattcctg tcacccatcg gcatggagca ggtccactta gattcccgat cacccacgca      480
catctcgcta atagtcattc gttcgtgtct cgatcaatc tcaagtgagt gtgcatggat       540
cttggttgac gatgcggtat gggtttgcgc cgctggctgc agggtctgcc caaggcaagc      600
taacccagct cctctccccg acaatactct cgcaggcaaa gccggtcact tgccttccag      660
attgccaata aactcaatta tggcctctgt catgccatcc atgggtctga tgaatggtca      720
cgctcgtgtc ctgaccgttc cccagcctct ggcgtccct gccccgccca ccagcccacg       780
ccgcgcggca gtcgctgcca aggctgtctc ggaggtaccc tttcttgcgc tatgacactt      840
ccagcaaaag gtagggcggg ctgcgagacg gcttcccggc gctgcatgca acaccgatga      900
tgcttcgacc ccccgaagct ccttcggggc tgcatgggcg ctccgatgcc gctccagggc      960
gagcgctgtt taaatagcca ggcccccgat tgcaaagaca ttatagcgag ctaccaaagc     1020
catattcaaa cacctagatc actaccactt ctacacaggc cactcgagct tgtgatcgca     1080
ctccgctaag ggggcgcctc ttcctcttcg tttcagtcac aacccgcaaa ctctagaata     1140
tcaatgctgc tgcaggcctt cctgttcctg ctggccggct cgccgccaa gatcagcgcc      1200
```

-continued

```
tccatgacga acgagacgtc cgaccgcccc ctggtgcact tcacccccaa caagggctgg    1260
atgaacgacc ccaacggcct gtggtacgac gagaaggacg ccaagtggca cctgtacttc    1320
cagtacaacc cgaacgacac cgtctggggg acgcccttgt tctggggcca cgccacgtcc    1380
gacgacctga ccaactggga ggaccagccc atcgccatcg ccccgaagcg caacgactcc    1440
ggcgccttct ccggctccat ggtggtggac tacaacaaca cctccggctt cttcaacgac    1500
accatcgacc cgcgccagcg ctgcgtggcc atctggacct acaacacccc ggagtccgag    1560
gagcagtaca tctcctacag cctggacggc ggctacacct tcaccgagta ccagaagaac    1620
cccgtgctgg ccgccaactc cacccagttc cgcgacccga aggtcttctg gtacgagccc    1680
tcccagaagt ggatcatgac cgcggccaag tcccaggact acaagatcga gatctactcc    1740
tccgacgacc tgaagtcctg gaagctggag tccgcgttcg ccaacgaggg cttcctcggc    1800
taccagtacg agtgccccgg cctgatcgag gtccccaccg agcaggaccc cagcaagtcc    1860
tactgggtga tgttcatctc catcaacccc ggcgccccgg ccggcggctc cttcaaccag    1920
tacttcgtcg gcagcttcaa cggcacccac ttcgaggcct tcgacaacca gtcccgcgtg    1980
gtggacttcg gcaaggacta ctacgccctg cagaccttct tcaacaccga cccgaccta c   2040 gggagcgccc tgggcatcgc gtgggcctcc aactgggagt actccgcctt cgtgcccacc    2100
aacccctggc gctcctccat gtccctcgtg cgcaagttct ccctcaacac cgagtaccag    2160
gccaacccgg agacggagct gatcaacctg aaggccgagc cgatcctgaa catcagcaac    2220 gccgcccct ggagccggtt cgccaccaac accacgttga cgaaggccaa cagctacaac     2280
gtcgacctgt ccaacagcac cggcaccctg gagttcgagc tggtgtacgc cgtcaacacc    2340
acccagacga tctccaagtc cgtgttcgcg gacctctccc tctggttcaa gggcctggag    2400
gaccccgagg agtacctccg catgggcttc gaggtgtccg cgtcctcctt cttcctggac    2460
cgcgggaaca gcaaggtgaa gttcgtgaag gagaacccct acttcaccaa ccgcatgagc    2520
gtgaacaacc agcccttcaa gagcgagaac gacctgtcct actacaaggt gtacggcttg    2580
ctggaccaga acatcctgga gctgtacttc aacgacggcg acgtcgtgtc caccaacacc    2640
tacttcatga ccaccgggaa cgccctgggc tccgtgaaca tgacgacggg ggtggacaac    2700
ctgttctaca tcgacaagtt ccaggtgcgc gaggtcaagt gacaattgac gcccgcgcgg    2760
cgcacctgac ctgttctctc gagggcgcct gttctgcctt gcgaaacaag ccctggagc     2820 atgcgtgcat gatcgtctct ggcgccccgc cgcgcggttt gtcgccctcg cgggcgccgc    2880
ggccgcgggg gcgcattgaa attgttgcaa accccacctg acagattgag ggcccaggca    2940
ggaaggcgtt gagatggagg tacaggagtc aagtaactga aagttttat gataactaac     3000 aacaaagggt cgtttctggc cagcgaatga caagaacaag attccacatt ccgtgtagga    3060
ggcttgccat cgaatgtgag cgggcggcc gcggacccga caaaaccctt acgacgtggt      3120
aagaaaaacg tggcgggcac tgtccctgta gcctgaagac cagcaggaga cgatcggaag    3180
catcacagca caggatcccg cgtctcgaac agagcgcgca gaggaacgct gaaggtctcg    3240
cctctgtcgc acctcagcgc ggcatacacc acaataacca cctgacgaat gcgcttggtt    3300
cttcgtccat tagcgaagcg tccggttcac acacgtgcca cgttggcgag gtggcaggtg    3360
acaatgatcg gtggagctga tggtcgaaac gttcacagcc tagggatggg agcagttgtc    3420 gaccgccgc gtcccgcagg cagcgatgac gtgtgcgtgg cctgggtgtt tcgtcgaaag     3480
gccagcaacc ctaaatcgca ggcgatccgg agattgggat ctgatccgag tttggaccag    3540
```

-continued

```
atccgccccg atgcggcacg ggaactgcat cgactcggcg cggaacccag ctttcgtaaa    3600
tgccagattg gtgtccgata cctggatttg ccatcagcga aacaagactt cagcagcgag    3660
cgtatttggc gggcgtgcta ccagggttgc atacattgcc catttctgtc tggaccgctt    3720
tactggcgca gagggtgagt tgatgggggtt ggcaggcatc gaaacgcgcg tgcatggtgt    3780
gcgtgtctgt tttcggctgc acgaattcaa tagtcggatg ggcgacggta gaattgggtg    3840
tggcgctcgc gtgcatgcct cgccccgtcg ggtgtcatga ccgggactgg aatcccccct    3900
cgcgaccatc ttgctaacgc tcccgactct cccgaccgcg cgcaggatag actcttgttc    3960
aaccaatcga caactagtac atatggcttc cgcggcattc accatgtcgg cgtgccccgc    4020
gatgactggc agggcccctg gggcacgtcg ctccggacgg ccagtcgcca cccgcctgag    4080
gggctccacc ttccagtgcc tggtgaactc ccacatcgac ccctgcaacc agaacgtgtc    4140
ctccgcctcc ctgtccttcc tgggcgacaa cggcttcggc tccaaccccct tccgctccaa    4200 ccgcggccac cgccgcctgg gccgcgcctc ccactccggc gaggccatgg ccgtggccct    4260
gcagcccgcc caggaggtgg ccaccaagaa gaagcccgcc atcaagcagc gccgcgtggt    4320
ggtgaccggc atgggcgtgg tgacccccgct gggccacgag cccgacgtgt tctacaacaa    4380
cctgctggac ggcgtgtccg gcatctccga gatcgagacc ttcgactgca cccagttccc    4440
cacccgcatc gccggcgaga tcaagtcctt ctccaccgac ggctgggtgg ccccgaagct    4500
gtccaagcgc atggacaagt tcatgctgta cctgctgacc gccggcaaga aggccctggc    4560
cgacgccggc atcaccgagg acgtgatgaa ggagctggac aagcgcaagt gcggcgtgct    4620
gatcggctcc ggcatgggcg gcatgaagct gttcaacgac tccatcgagg ccctgcgcgt    4680
gtcctacaag aagatgaacc ccttctgcgt gcccttcgcc accaccaaca tgggctccgc    4740
catgctggcc atggacctgg gctggatggg ccccaactac tccatctcca ccgcctgcgc    4800
cacctccaac ttctgcatcc tgaacgccgc caaccacatc atccgcggcg aggccgacat    4860
gatgctgtgc ggcggctccg acgccgtgat catccccatc ggcctgggcg gcttcgtggc    4920
ctgccgcgcc ctgtcccagc gcaactccga ccccaccaag gcctcccgcc ctgggactc    4980 caaccgcgac ggcttcgtga tgggcgaggg cgccggcgtg ctgctgctgg aggagctgga    5040
gcacgccaag aagcgcggcg ccaccatcta cgccgagttc ctgggcggct ccttcacctg    5100
cgacgcctac cacatgaccg agccgcaccc ggacggcgcc ggcgtgatcc tgtgcatcga    5160
gaaggccctg gcccagtccg gcgtgtcccg cgaggacgtg aactacatca acgcccacgc    5220
cacctccacc ccgccgcggcg acatcaagga gtaccaggcc ctggcccact gcttcggcca    5280
gaactccgag ctgcgcgtga actccaccaa gtccatgatc ggccacctgc tgggcgccgc    5340
cggcggcgtg gaggccgtga ccgtgatcca ggccatccgc accggctgga tccaccccaa    5400
cctgaacctg gaggaccccg acgaggccgt ggacgccaag ttcctggtgg ccccaagaa    5460 ggagcgcctg aacgtgaagg tgggcctgtc caactccttc ggcttcggcg ccacaactc    5520 ctccatcctg ttcgccccgt acaacaccat gtaccccctac gacgtgcccg actacgcctg    5580
agatatcgga gcgacgagtg tgcgtgcggg gctggcggga gtgggacgcc ctcctcgctc    5640
ctctctgttc tgaacggaac aatcggccac cccgcgctac gcgccacgca tcgagcaacg    5700
aagaaaaccc cccgatgata ggttgcggtg gctgccggga tatagatccg gccgcacatc    5760
aaagggcccc tccgccagag aagaagctcc tttcccagca gactccttct gctgccaaaa    5820
cacttctctg tccacagcaa caccaaagga tgaacagatc aacttgcgtc tccgcgtagc    5880
ttcctcggct agcgtgcttg caacaggtcc ctgcactatt atcttcctgc tttcctctga    5940
```

-continued

```
attatgcggc aggcgagcgc tcgctctggc gagcgctcct tcgcgccgcc ctcgctgatc   6000
gagtgtacag tcaatgaatg gtgagctcca gcgccatgcc acgcccttg atggcttcaa     6060 gtacgattac ggtgttggat tgtgtgtttg ttgcgtagtg tgcatggttt agaataatac    6120
acttgatttc ttgctcacgg caatctcggc ttgtccgcag gttcaacccc atttcggagt    6180
ctcaggtcag ccgcgcaatg accagccgct acttcaagga cttgcacgac aacgccgagg   6240
tgagctatgt ttaggacttg attggaaatt gtcgtcgacg catattcgcg ctccgcgaca    6300
gcacccaagc aaaatgtcaa gtgcgttccg atttgcgtcc gcaggtcgat gttgtgatcg   6360 tcggcgccg atccgccggt ctgtcctgcg cttacgagct gaccaagcac cctgacgtcc     6420
gggtacgcga gctgagattc gattagacat aaattgaaga ttaaaccgt agaaaaattt      6480 gatggtcgcg aaactgtgct cgattgcaag aaattgatcg tcctccactc cgcaggtcgc    6540
catcatcgag cagggcgttg ctcccggcgg cggcgcctgg ctggggggac agctgttctc   6600
ggccatgtgt gtacgtagaa ggatgaattt cagctggttt tcgttgcaca gctgtttgtg   6660
catgatttgt ttcagactat tgttgaatgt ttttagattt cttaggatgc atgatttgtc    6720
tgcatgcgac tgaagagcgt ttaaaccgcc tctccccgcg cgttggccga ttcattaatg    6780
cagctggcac gacaggtttc ccgactggaa agcgggcagt gagcgcaacg caattaatgt     6840
gagttagctc actcattagg cacccaggc tttacacttt atgcttccgg ctcgtatgtt       6900
gtgtggaatt gtgagcggat aacaatttca cacaggaaac agctatgacc atgattacgc    6960
caagctcgaa attaaccctc actaaaggga acaaaagctg gcaattcgcc ctatagtgag    7020
tcgtattacg cgcgctcact ggccgtcgtt ttacaacgtc gtgactggga aaaccctggc    7080
gttacccaac ttaatcgcct tgcagcacat cccccttcg ccagctggcg taatagcgaa      7140
gaggcccgca ccgatcgccc ttcccaacag ttgcgcagcc tgaatggcga atgggacgcg   7200
ccctgtagcg gcgcattaag cgcggcgggt gtggtggtta cgcgcagcgt gaccgctaca   7260
cttgccagcg ccctagcgcc cgctcctttc gctttcttcc cttcctttct cgccacgttc    7320
gccggctttc cccgtcaagc tctaaatcgg gggctccctt tagggttccg atttagtgct     7380
ttacggcacc tcgacccca aaaacttgat tagggtgatg gttcacgtag tgggccatcg     7440
ccctgataga cggtttttcg ccctttgacg ttggagtcca cgttctttaa tagtggactc    7500
ttgttccaaa ctggaacaac actcaaccct atctcggtct attcttttga tttataaggg   7560
attttgccga tttcggccta ttggttaaaa aatgagctga tttaacaaaa atttaacgcg   7620
aattttaaca aaatattaac gcttacaatt taggtggcac ttttcgggga aatgtgcgcg   7680
gaacccctat ttgtttattt ttctaaatac attcaaatat gtatccgctc atgagacaat    7740
aaccctgata aatgcttcaa taatattgaa aaaggaagag tatgagtatt caacatttcc    7800
gtgtcgccct tattcccttt tttgcggcat tttgccttcc tgtttttgct cacccagaaa   7860
cgctggtgaa agtaaaagat gctgaagatc agttgggtgc acgagtgggt tacatcgaac    7920
tggatctcaa cagcggtaag atccttgaga gttttcgccc cgaagaacgt tttccaatga    7980
tgagcacttt taaagttctg ctatgtggcg cggtattatc ccgtattgac gccgggcaag   8040
agcaactcgg tcgccgcata cactattctc agaatgactt ggttgagtac tcaccagtca    8100
cagaaaagca tcttacggat ggcatgacag taagagaatt atgcagtgct gccataacca    8160
tgagtgataa cactgcggcc aacttacttc tgacaacgat cggaggaccg aaggagctaa    8220 ccgcttttt gcacaacatg ggggatcatg taactcgcct tgatcgttgg gaaccggagc     8280
```

-continued

```
tgaatgaagc cataccaaac gacgagcgtg acaccacgat gcctgtagca atggcaacaa      8340
cgttgcgcaa actattaact ggcgaactac ttactctagc ttcccggcaa caattaatag      8400
actggatgga ggcggataaa gttgcaggac cacttctgcg ctcggccctt ccggctggct      8460
ggtttattgc tgataaatct ggagccggtg agcgtgggtc tcgcggtatc attgcagcac      8520
tggggccaga tggtaagccc tcccgtatcg tagttatcta cacgacgggg agtcaggcaa      8580
ctatggatga acgaaataga cagatcgctg agataggtgc ctcactgatt aagcattggt      8640
aactgtcaga ccaagtttac tcatatatac tttagattga tttaaaactt cattttaat      8700 ttaaaaggat ctaggtgaag atcctttttg ataatctcat gaccaaaatc ccttaacgtg      8760
agttttcgtt ccactgagcg tcagacccg tagaaaagat caaaggatct tcttgagatc      8820 cttttttct gcgcgtaatc tgctgcttgc aaacaaaaaa accaccgcta ccagcggtgg      8880
tttgtttgcc ggatcaagag ctaccaactc tttttccgaa ggtaactggc ttcagcagag      8940
cgcagatacc aaatactgtc cttctagtgt agccgtagtt aggccaccac ttcaagaact      9000
ctgtagcacc gcctacatac ctcgctctgc taatcctgtt accagtggct gctgccagtg      9060
gcgataagtc gtgtcttacc gggttggact caagacgata gttaccggat aaggcgcagc      9120
ggtcgggctg aacgggggt tcgtgcacac agcccagctt ggagcgaacg acctacaccg      9180
aactgagata cctacagcgt gagctatgag aaagcgccac gcttcccgaa gggagaaagg      9240
cggacaggta tccggtaagc ggcagggtcg gaacaggaga gcgcacgagg gagcttccag      9300
ggggaaacgc ctggtatctt tatagtcctg tcgggtttcg ccacctctga cttgagcgtc      9360
gatttttgtg atgctcgtca gggggcgga gcctatggaa aaacgccagc aacgcggcct      9420
ttttacggtt cctggccttt tgctggcctt ttgctcacat gttctttcct gcgttatccc      9480
ctgattctgt ggataaccgt attaccgcct ttgagtgagc tgataccgct cgccgcagcc      9540
gaacgaccga gcgcagcgag tcagtgagcg agga                                  9574
```

```
<210> SEQ ID NO 14
<211> LENGTH: 1599
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (436)..(438)
<223> OTHER INFORMATION: n is, independently, a, c, g, or t

<400> SEQUENCE: 14
```

```
atggcttccg cggcattcac catgtcggcg tgccccgcga tgactggcag ggcccctggg        60
gcacgtcgct ccggacggcc agtcgccacc cgcctgaggg gctccacctt ccagtgcctg       120
gtgaactccc acatcgaccc ctgcaaccag aacgtgtcct ccgcctccct gtccttcctg       180
ggcgacaacg gcttcggctc caaccccttc cgctccaacc gcggccaccg ccgcctgggc       240
cgcgcctccc actccggcga ggccatggcc gtggccctgc agcccgccca ggaggtggcc       300
accaagaaga agcccgccat caagcagcgc cgcgtggtgg tgaccggcat gggcgtggtg       360
accccgctgg gccacgagcc cgacgtgttc tacaacaacc tgctggacgg cgtgtccggc       420
atctccgaga tcgagnnntt cgactgcacc cagttcccca cccgcatcgc cggcgagatc       480
aagtccttct ccaccgacgg ctgggtggcc ccgaagctgt ccaagcgcat ggacaagttc       540
atgctgtacc tgctgaccgc cggcaagaag gccctggccg acgccggcat caccgaggac       600
gtgatgaagg agctggacaa cgcgcaagtgc ggcgtgctga tcggctccgg catgggcggc       660
```

-continued

```
atgaagctgt tcaacgactc catcgaggcc ctgcgcgtgt cctacaagaa gatgaacccc      720
ttctgcgtgc ccttcgccac caccaacatg ggctccgcca tgctggccat ggacctgggc      780
tggatgggcc ccaactactc catctccacc gcctgcgcca cctccaactt ctgcatcctg      840
aacgccgcca accacatcat ccgcggcgag gccgacatga tgctgtgcgg cggctccgac      900
gccgtgatca tccccatcgg cctgggcggc ttcgtggcct gccgcgccct gtcccagcgc      960
aactccgacc ccaccaaggc ctcccgcccc tgggactcca accgcgacgg cttcgtgatg     1020
ggcgagggcg ccggcgtgct gctgctggag gagctggagc acgccaagaa gcgcggcgcc     1080
accatctacg ccgagttcct gggcggctcc ttcacctgcg acgcctacca catgaccgag     1140
ccgcacccgg acggcgccgg cgtgatcctg tgcatcgaga aggccctggc ccagtccggc     1200
gtgtcccgcg aggacgtgaa ctacatcaac gcccacgcca cctccacccc ggccggcgac     1260
atcaaggagt accaggccct ggcccactgc ttcggccaga actccgagct gcgcgtgaac     1320
tccaccaagt ccatgatcgg ccacctgctg ggcgccgccg cgggcgtgga ggccgtgacc     1380
gtgatccagg ccatccgcac cggctggatc cacccccaacc tgaacctgga ggaccccgac    1440
gaggccgtgg acgccaagtt cctggtgggc cccaagaagg agcgcctgaa cgtgaaggtg     1500
ggcctgtcca actccttcgg cttcggcggc cacaactcct ccatcctgtt cgccccgtac     1560
aacaccatgt accctacga cgtgcccgac tacgcctga                             1599
```

```
<210> SEQ ID NO 15
<211> LENGTH: 9402
<212> TYPE: DNA
<213> ORGANISM: Artificial Sequence
<220> FEATURE:
<223> OTHER INFORMATION: synthetic

<400> SEQUENCE: 15
```

```
gatcttcttg agatcctttt tttctgcgcg taatctgctg cttgcaaaca aaaaaaccac       60
cgctaccagc ggtggtttgt ttgccggatc aagagctacc aactcttttt ccgaaggtaa      120
ctggcttcag cagagcgcag ataccaaata ctgtccttct agtgtagccg tagttaggcc      180
accacttcaa gaactctgta gcaccgccta catacctcgc tctgctaatc ctgttaccag      240
tggctgctgc cagtggcgat aagtcgtgtc ttaccgggtt ggactcaaga cgatagttac      300
cggataaggc gcagcggtcg ggctgaacgg ggggttcgtg cacacagccc agcttggagc      360
gaacgaccta caccgaactg agatacctac agcgtgagct atgagaaagc gccacgcttc      420
ccgaagggag aaaggcggac aggtatccgg taagcggcag ggtcggaaca ggagagcgca      480
cgagggagct ccagggggaa acgcctggt atctttatag tcctgtcggg tttcgccacc      540
tctgacttga gcgtcgattt ttgtgatgct cgtcaggggg gcggagccta tggaaaaacg      600
ccagcaacgc ggcctttta cggttcctgg ccttttgctg gccttttgct cacatgttct      660
ttcctgcgtt atccctgat tctgtggata accgtattac cgcctttgag tgagctgata      720
ccgctcgccg cagccgaacg accgagcgca gcgagtcagt gagcgaggaa gcggaagagc      780
gcccaatgtt aaacagccc gcaccctcgt tgatctggga gccctgcgca gcccttaaa      840 tcatctcagt caggtttctg tgttcaactg agcctaaagg gctttcgtca tgcgcacgag      900
cacacgtata tcggccacgc agtttctcaa aagcggtaga acagttcgcg agccctcgta      960
ggtcgaaaac ttgcgccagt actattaaat taaattaatt gatcgaacga gacgcgaaac     1020
ttttgcagaa tgccaccgag tttgcccaga gaatgggagt ggcgccattc accatccgcc     1080
```

-continued

```
tgtgcccggc ttgattcgcc gagacgatgg acggcgagac cagggagcgg cttgcgagcc      1140
ccgagccggt agcaggaaca atgatcgaca atcttcctgt ccaattactg gcaaccatta      1200
gaaagagccg gagcgcgttg aaagtctgca atcgagtaat ttttcgatac gtcgggcctg      1260
ctgaacccta aggctccgga ctttgtttaa ggcgatccaa gatgcacgcg gccccaggca      1320
cgtatctcaa gcacaaaccc cagccttagt ttcgagactt tgggagatag cgaccgatat      1380
ctagtttggc attttgtata ttaattacct caagcaatgg agcgctctga tgcggtgcag      1440
cgtcggctgc agcacctggc agtggcgcta gggtcgccct atcgctcgga acctggtcag      1500
ctggctcccg cctcctgctc agcctcttcc ggtaccccgc tcccgtctgg tcctcacgtt      1560
cgtgtacggc ctggatcccg gaaagggcgg atgcacgtgg tgttgccccg ccattggcgc      1620
ccacgtttca aagtccccgg ccagaaatgc acaggaccgg cccggctcgc acaggccatg      1680
acgaatgccc agatttcgac agcaaaacaa tctggaataa tcgcaaccat tcgcgttttg      1740
aacgaaacga aaagacgctg tttagcacgt ttccgatatc gtgggggccg aagcatgatt      1800
ggggggagga aagcgtggcc ccaaggtagc ccattctgtg ccacacgccg acgaggacca      1860
atccccggca tcagccttca tcgacggctg cgccgcacat ataaagccgg acgccttccc      1920
gacacgttca aacagttta ttt cctccac ttcctgaatc aaacaaatct tcaaggaaga      1980
tcctgctctt gagcagctag caccatggcc accgcatcca ctttctcggc gttcaatgcc      2040
cgctgcggcg acctgcgtcg ctcggcgggc tccgggcccc ggcgcccagc gaggcccctc      2100
cccgtgcgcg ggcgcgcccg cgccacgctg acgttcgacc cccccacgac caactccgag      2160
cgcgccaagc agcgcaagca caccatcgac ccctcctccc ccgacttcca gcccatcccc      2220
tccttcgagg agtgcttccc caagtccacg aaggagcaca aggaggtggt gcacgaggag      2280
tccggccacg tcctgaaggt gcccttccgc cgcgtgcacc tgtccggcgg cgagcccgcc      2340
ttcgacaact acgacacgtc cggcccccag aacgtcaacg cccacatcgg cctggcgaag      2400
ctgcgcaagg agtggatcga ccgccgcgag aagctgggca cgccccgcta cacgcagatg      2460
tactacgcga agcagggcat catcacggag gagatgctgt actgcgcgac gcgcgagaag      2520
ctggaccccg agttcgtccg ctccgaggtc gcgcggggcc gcgccatcat ccctccaac      2580 aagaagcacc tggagctgga gcccatgatc gtgggccgca agttcctggt gaaggtgaac      2640
gcgaacatcg gcaactccgc cgtggcctcc tccatcgagg aggaggtcta caaggtgcag      2700
tgggccacca tgtggggcgc cgacaccatc atggacctgt ccacgggccg ccacatccac      2760
gagacgcgcg agtggatcct gcgcaactcc gcggtccccg tgggcaccgt ccccatctac      2820
caggcgctgg agaaggtgga cggcatcgcg gagaacctga actgggaggt gttccgcgag      2880
acgctgatcg agcaggccga gcagggcgtg gactacttca cgatccacgc gggcgtgctg      2940
ctgcgctaca tccccctgac cgccaagcgc atgacgggca tcgtgtcccg cggcggctcc      3000
atccacgcga gtggtgcct ggcctaccac aaggagaact cgcctacga gcactgggac      3060 gacatcctgg acatctgcaa ccagtacgac gtcgccctgt ccatcggcga cggcctgcgc      3120
cccggctcca tctacgacgc caacgacacg gcccagttcg ccgagctgct gacccagggc      3180
gagctgacgc gccgcgcgtg ggagaaggac gtgcaggtga tgaacgaggg ccccggccac      3240
gtgcccatgc acaagatccc cgagaacatg cagaagcagc tggagtggtg caacgaggcg      3300
cccttctaca ccctgggccc cctgacgacc gacatcgcgc ccggctacga ccacatcacc      3360
tccgccatcg gcgcggccaa catcggcgcc ctgggcaccg ccctgctgtg ctacgtgacg      3420
cccaaggagc acctgggcct gcccaaccgc gacgacgtga aggcgggcgt catcgcctac      3480
```

```
aagatcgccg cccacgcggc cgacctggcc aagcagcacc cccacgccca ggcgtgggac   3540
gacgcgctgt ccaaggcgcg cttcgagttc cgctggatgg accagttcgc gctgtccctg   3600
gaccccatga cggcgatgtc cttccacgac gagacgctgc ccgcggacgg cgcgaaggtc   3660
gcccacttct gctccatgtg cggccccaag ttctgctcca tgaagatcac ggaggacatc   3720
cgcaagtacg ccgaggagaa cggctacggc tccgccgagg aggccatccg ccagggcatg   3780
gacgccatgt ccgaggagtt caacatcgcc aagaagacga tctccggcga gcagcacggc   3840
gaggtcggcg gcgagatcta cctgcccgag tcctacgtca aggccgcgca gaagtgatac   3900
cttattacgt aacagacgac cttggcaggc gtcgggtagg gaggtggtgg tgatggcgtc   3960
tcgatgccat cgcacgcatc caacgaccgt atacgcatcg tccaatgacc gtcggtgtcc   4020
tctctgcctc cgttttgtga gatgtctcag gcttggtgca tcctcgggtg gccagccacg   4080
ttgcgcgtcg tgctgcttgc ctctcttgcg cctctgtggt actggaaaat atcatcgagg   4140
cccgtttttt tgctcccatt tcctttccgc tacatcttga aagcaaacga caaacgaagc   4200
agcaagcaaa gagcacgagg acggtgaaca agtctgtcac ctgtatacat ctatttcccc   4260
gcgggtgcac ctactctctc tcctgccccg gcagagtcag ctgccttacg tgacggatcc   4320
cgcgtctcga acagagcgcg cagaggaacg ctgaaggtct cgcctctgtc gcacctcagc   4380
gcggcataca ccacaataac cacctgacga atgcgcttgg ttcttcgtcc attagcgaag   4440
cgtccggttc acacacgtgc cacgttggcg aggtggcagg tgacaatgat cggtggagct   4500
gatggtcgaa acgttcacag cctagggata tcgggagcag ttgtcgaccg cccgcgtccc   4560
gcaggcagcg atgacgtgtg cgtggcctgg gtgtttcgtc gaaaggccag caaccctaaa   4620
tcgcaggcga tccggagatt gggatctgat ccgagtttgg accagatccg ccccgatgcg   4680
gcacgggaac tgcatcgact cggcgcggaa cccagctttc gtaaatgcca gattggtgtc   4740
cgatacctgg atttgccatc agcgaaacaa gacttcagca gcgagcgtat ttggcgggcg   4800
tgctaccagg gttgcataca ttgcccattt ctgtctggac cgctttactg gcgcagaggg   4860
tgagttgatg gggttggcag gcatcgaaac gcgcgtgcat ggtgtgcgtg tctgttttcg   4920
gctgcacgaa ttcaatagtc ggatgggcga cggtagaatt gggtgtggcg ctcgcgtgca   4980
tgcctcgccc cgtcgggtgt catgaccggg actggaatcc cccctcgcga ccatcttgct   5040
aacgctcccg actctcccga ccgcgcgcag gatagactct tgttcaacca atcgacaact   5100
agtaacaatg gccaccgcct ccaccttctc cgccttcaac gcccgctgcg gcgacctgcg   5160
ccgctccgcc ggctccggcc cccgcgcgcc cgcccgcccc ctgcccgtgc gcgccgccat   5220
caacgcctcc gcccacccca aggccaacgg ctccgccgtg aacctgaagt ccggctccct   5280
gaacacccag gaggacacct cctcctctcc gcctccccgc gccttcctga accagctgcc   5340
cgactggtcc atgctggtgg actccgtggg cctgaagtcc gtggtgctgg acggcctggt   5400
gtcccgccag atcttctcca tccgctccta cgagatcggc gccgaccgca ccgcctccat   5460
cgagaccctg atgaaccacc tgcaggagac ctccatcaac cactgcaagt ccctgggcct   5520
gctgaacgac ggcttcggcc gcaccccggg catgtgcaag aacgacctga tctgggtgct   5580
gaccaagatg cagatcatgg tgaaccgcta ccccacctgg ggcgacaccg tggagatcaa   5640
cacctggttc tcccactccg gcaagatcgg catggcctcc gactggctga tcaccgactg   5700
caacaccggc gagatcctga tccgcgccac ctccgtgtgg gccatgatga accagaagac   5760
ccgccgcttc tcccgcctgc cctacgaggt gcgccaggag ctgacccctc actacgtgga   5820
```

-continued

```
ctccccgcac gtgatcgagg acaacgaccg caagctgcac aagttcgacg tgaagaccgg    5880
cgactccatc cgcaagggcc tgacccctcg ctggaacgac ctggacgtga accagcacgt    5940
gtccaacgtg aagtacatcg gctggatcct ggagtccatg cccatcgagg tgctggagac    6000
ccaggagctg tgctccctga ccgtggagta ccgccgcgag tgcggcatgg actccgtgct    6060
ggagtccgtg accgccatgg acccctccga ggacgagggc cgctcccagt acaagcacct    6120
gctgcgcctg gaggacggca ccgacatcgt gaagggccgc accgagtggc gccccaagaa    6180
cgccggcacc aacggcgcca tctccaccgc caagccctcc aacggcaact ccgtgtccat    6240
ggactacaag gaccacgacg gcgactacaa ggaccacgac atcgactaca aggacgacga    6300
cgacaagtga ctcgagggag cgacgagtgt gcgtgcgggg ctggcgggag tgggacgccc    6360
tcctcgctcc tctctgttct gaacggaaca atcggccacc ccgcgctacg cgccacgcat    6420
cgagcaacga agaaaacccc ccgatgatag gttgcggtgg ctgccgggat atagatccgg    6480
ccgcacatca aagggcccct ccgccagaga agaagctcct ttcccagcag actccttctg    6540
ctgccaaaac acttctctgt ccacagcaac accaaaggat gaacagatca acttgcgtct    6600
ccgcgtagct tcctcggcta gcgtgcttgc aacaggtccc tgcactatta tcttcctgct    6660
ttcctctgaa ttatgcggca ggcgagcgct cgctctggcg agcgctcctt cgcgccgccc    6720
tcgctgatcg agtgtacagt caatgaatgg tgagctcagc gtctgcgtgt tgggagctgg    6780
agtcgtgggc ttgacgacgg cgctgcagct gttgcaggat gtgcctggcg tgcgcgttca    6840
cgtcgtggct gagaaatatg cgacgaaac gttgacggct ggggccggcg ggctgtggat    6900
gccatacgca ttgggtacgc ggccattgga tgggattgat aggcttatgg agggataata    6960
gagtttttgc cggatccaac gcatgtggat gcggtatccc ggtgggctga aagtgtggaa    7020
ggatagtgca ttggctattc acatgcactg cccacccctt ttggcaggaa atgtgccggc    7080
atcgttggtg caccgatggg gaaaatcgac gttcgaccac tacatgaaga tttatacgtc    7140
tgaagatgca gcgactgcgg gtgcgaaacg gatgacggtt tggtcgtgta tgtcacagca    7200
tgtgctggat cttgcgggct aactccccct gccacggccc attgcaggtg tcatgttgac    7260
tggagggtac gacctttcgt ccgtcaaatt cccagaggag gacccgctct gggccgacat    7320
tgtgcccact gaagagcgtt taaaccgcct ctccccgcgc gttggccgat tcattaatgc    7380
agctggcacg acaggtttcc cgactggaaa gcgggcagtg agcgcaacgc aattaatgtg    7440
agttagctca ctcattaggc accccaggct ttacacttta tgcttccggc tcgtatgttg    7500
tgtggaattg tgagcggata acaatttcac acaggaaaca gctatgacca tgattacgcc    7560
aagctcgaaa ttaaccctca ctaaagggaa caaaagctgg ccaattcgcc ctatagtgag    7620
tcgtattaca attcactggc cgtcgtttta caacgtcgtg actgggaaaa ccctggcgtt    7680
acccaactta atcgccttgc agcacatccc cctttcgcca gctggcgtaa tagcgaagag    7740
gcccgcaccg atcgcccttc ccaacagttg cgcagcctga atggcgaatg ggacgcgccc    7800
tgtagcggcg cattaagcgc ggcgggtgtg gtggttacgc gcagcgtgac cgctacactt    7860
gccagcgccc tagcgcccgc tcctttcgct ttcttccctt cctttctcgc cacgttcgcc    7920
ggctttcccc gtcaagctct aaatcggggg ctccctttag ggttccgatt tagtgcttta    7980
cggcacctcg accccaaaaa acttgattag ggtgatggtt cacgtagtgg gccatcgccc    8040
tgatagacgg tttttcgccc tttgacgttg gagtccacgt tctttaatag tggactcttg    8100
ttccaaactg gaacaacact caaccctatc tcggtctatt cttttgattt ataagggatt    8160
ttgccgattt cggcctattg gttaaaaaat gagctgattt aacaaaaatt taacgcgaat    8220
```

```
tttaacaaaa tattaacgct tacaatttag gtggcacttt tcggggaaat gtgcgcggaa      8280
cccctatttg tttattttc taaatacatt caaatatgta tccgctcatg agacaataac       8340
cctgataaat gcttcaataa tattgaaaaa ggaagagtat gagtattcaa catttccgtg       8400
tcgcccttat tccctttttt gcggcatttt gccttcctgt ttttgctcac ccagaaacgc       8460
tggtgaaagt aaaagatgct gaagatcagt tgggtgcacg agtgggttac atcgaactgg       8520
atctcaacag cggtaagatc cttgagagtt ttcgccccga agaacgtttt ccaatgatga       8580
gcacttttaa agttctgcta tgtggcgcgg tattatcccg tattgacgcc gggcaagagc       8640
aactcggtcg ccgcatacac tattctcaga atgacttggt tgagtactca ccagtcacag       8700
aaaagcatct tacggatggc atgacagtaa gagaattatg cagtgctgcc ataaccatga       8760
gtgataacac tgcggccaac ttacttctga caacgatcgg aggaccgaag gagctaaccg       8820
cttttttgca caacatgggg gatcatgtaa ctcgccttga tcgttgggaa ccggagctga       8880
atgaagccat accaaacgac gagcgtgaca ccacgatgcc tgtagcaatg gcaacaacgt       8940
tgcgcaaact attaactggc gaactactta ctctagcttc ccggcaacaa ttaatagact       9000
ggatggaggc ggataaagtt gcaggaccac ttctgcgctc ggcccttccg gctggctggt       9060
ttattgctga taaatctgga gccggtgagc gtgggtctcg cggtatcatt gcagcactgg       9120
ggccagatgg taagccctcc cgtatcgtag ttatctacac gacggggagt caggcaacta       9180
tggatgaacg aaatagacag atcgctgaga taggtgcctc actgattaag cattggtaac       9240
tgtcagacca gtttactca tatatacttt agattgattt aaaacttcat ttttaattta       9300
aaaggatcta ggtgaagatc cttttttgata atctcatgac caaaatccct taacgtgagt       9360
tttcgttcca ctgagcgtca gaccccgtag aaaagatcaa ag                          9402
```

<210> SEQ ID NO 16
<211> LENGTH: 13
<212> TYPE: PRT
<213> ORGANISM: Artificial Sequence
<220> FEATURE:
<223> OTHER INFORMATION: synthetic

<400> SEQUENCE: 16

```
Ser Gly Pro Arg Arg Pro Ala Arg Pro Leu Pro Val Arg
1               5                   10
```

<210> SEQ ID NO 17
<211> LENGTH: 28
<212> TYPE: PRT
<213> ORGANISM: Artificial Sequence
<220> FEATURE:
<223> OTHER INFORMATION: synthetic

<400> SEQUENCE: 17

```
Ser Gly Pro Arg Arg Pro Ala Arg Pro Leu Pro Val Arg Ala Ala Ile
1               5                   10                  15

Ala Ser Glu Val Pro Val Ala Thr Thr Ser Pro Arg
            20                  25
```

<210> SEQ ID NO 18
<211> LENGTH: 12
<212> TYPE: PRT
<213> ORGANISM: Artificial Sequence
<220> FEATURE:
<223> OTHER INFORMATION: synthetic

<400> SEQUENCE: 18

-continued

```
Arg Pro Ala Arg Pro Leu Pro Val Arg Gly Arg Ala
1               5               10

<210> SEQ ID NO 19
<211> LENGTH: 24
<212> TYPE: PRT
<213> ORGANISM: Artificial Sequence
<220> FEATURE:
<223> OTHER INFORMATION: synthetic

<400> SEQUENCE: 19

Arg Pro Ala Arg Pro Leu Pro Val Arg Ala Ala Ile Ala Ser Glu Val
1               5               10              15

Pro Val Ala Thr Thr Ser Pro Arg
            20

<210> SEQ ID NO 20
<211> LENGTH: 26
<212> TYPE: PRT
<213> ORGANISM: Artificial Sequence
<220> FEATURE:
<223> OTHER INFORMATION: synthetic

<400> SEQUENCE: 20

Arg Cys Gly Asp Leu Arg Arg Ser Ala Gly Ser Gly Pro Arg Arg Pro
1               5               10              15

Ala Arg Pro Leu Pro Val Arg Gly Arg Ala
            20              25

<210> SEQ ID NO 21
<211> LENGTH: 38
<212> TYPE: PRT
<213> ORGANISM: Artificial Sequence
<220> FEATURE:
<223> OTHER INFORMATION: synthetic

<400> SEQUENCE: 21

Arg Cys Gly Asp Leu Arg Arg Ser Ala Gly Ser Gly Pro Arg Arg Pro
1               5               10              15

Ala Arg Pro Leu Pro Val Arg Ala Ala Ile Ala Ser Glu Val Pro Val
            20              25              30

Ala Thr Thr Ser Pro Arg
        35

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Pro Ala Arg Pro Leu Pro Val Arg
1               5

<210> SEQ ID NO 23
<211> LENGTH: 23
<212> TYPE: PRT
<213> ORGANISM: Artificial Sequence
<220> FEATURE:
<223> OTHER INFORMATION: synthetic

<400> SEQUENCE: 23

Pro Ala Arg Pro Leu Pro Val Arg Ala Ala Ile Ala Ser Glu Val Pro
```

```
1               5                10               15

Val Ala Thr Thr Ser Pro Arg
            20

<210> SEQ ID NO 24
<211> LENGTH: 10
<212> TYPE: PRT
<213> ORGANISM: Artificial Sequence
<220> FEATURE:
<223> OTHER INFORMATION: synthetic

<400> SEQUENCE: 24

Arg Arg Pro Ala Arg Pro Leu Pro Val Arg
1               5                10

<210> SEQ ID NO 25
<211> LENGTH: 25
<212> TYPE: PRT
<213> ORGANISM: Artificial Sequence
<220> FEATURE:
<223> OTHER INFORMATION: synthetic

<400> SEQUENCE: 25

Arg Arg Pro Ala Arg Pro Leu Pro Val Arg Ala Ala Ile Ala Ser Glu
1               5                10               15

Val Pro Val Ala Thr Thr Ser Pro Arg
            20             25
```

β-KETOACYL-ACP SYNTHASE IV VARIANTS

CROSS-REFERENCE TO RELATED APPLICATIONS

This patent application is the U.S. national stage of PCT/US2021/013575, filed Jan. 15, 2021, which claims the benefit of U.S. Provisional Patent Application No. 62/961, 996, filed Jan. 16, 2020, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 103,415 Byte ASCII (Text) file named "764369_ST25.txt," dated Jul. 14, 2022.

BACKGROUND

*Prototheca moriformis* base or wild-type strains produce oils with primarily palmitic acid (C16:0) and oleic acid (C18:1), which account for nearly 85% of the fatty acids present at the end of fermentation. The amount of medium-chain fatty acids, C8:0 to C14:0, is negligible with C12:0 and C14:0 present at low, non-zero levels. Chain lengthening from short chain fatty acids to longer chain fatty acids is catalyzed by β-ketoacyl-ACP synthase (KAS) enzymes. Medium-chain fatty acid levels near zero imply that the endogenous KAS enzymes in *P. moriformis* are not evolved for producing medium-chain fatty acids.

SUMMARY

In one aspect, provided are polynucleotides encoding a non-natural or variant β-ketoacyl-ACP synthase (KAS) IVa enzyme (KASIVa). In some embodiments, the non-natural KASIVa comprises at least about 80%, 85%, 90%, 91%, 92%, 93%, 94%, 95%, 96%, 97%, 98% or 99% identity to amino acid residues 34-523 of SEQ ID NO: 4 and comprises an X at the position corresponding to position 146; wherein X is an amino acid residue selected from the group consisting of glycine (G), asparagine (N), or serine (S), wherein the positions are with reference to SEQ ID NO: 4. In some embodiments, the non-natural KASIVa catalyzes the elongation of a medium-chain fatty acyl-ACP, e.g., from C8 to C10. In some embodiments, the non-natural KASIVa preferentially produces C10-ACP. In some embodiments, the non-natural KASIVa facilitates the production of increased levels of C10 fatty acids or the production of an oil with increased levels of C10 fatty acids in comparison to a wild-type KASIVa. In some embodiments, the non-natural KASIVa catalyzes the production of increased levels of C10 fatty acids in comparison to a wild-type KASIVa. In some embodiments, the non-natural KASIVa has increased activity on a C8-acyl substrate and/or has increased specificity for a C8-acyl substrate in the formation of the C10-acyl product (e.g., increases the ratio of C10 fatty acids to the sum of other fatty acids produced) in comparison to a wild-type KASIVa. In some embodiments, the X at position 146 is a serine (S) residue. In some embodiments, the X at position 146 is a glycine (G) residue. In some embodiments, the X at position 146 is asparagine (N). In some embodiments, the non-natural or variant KASIVa comprises a plastid transit peptide. In some embodiments, the plastid transit peptide comprises at least about 80%, 85%, 90%, 91%, 92%, 93%, 94%, 95%, 96%, 97%, 98% or 99% identity to amino acid residues 1-33 of SEQ ID NO: 3, SEQ ID NO: 4, SEQ ID NO: 10 or SEQ ID NO: 11. In some embodiments, the plastid transit peptide is encoded by a polynucleotide comprising at least about 80%, 85%, 90%, 91%, 92%, 93%, 94%, 95%, 96%, 97%, 98% or 99% identity to SEQ ID NO: 12. In some embodiments, the polynucleotide comprises at least about 80%, 85%, 90%, 91%, 92%, 93%, 94%, 95%, 96%, 97%, 98% or 99% identity to nucleic acid residues 100-1563 of SEQ ID NO: 7, SEQ ID NO: 9, or SEQ ID NO: 14. In some embodiments, the polynucleotide comprises at least about 80%, 85%, 90%, 91%, 92%, 93%, 94%, 95%, 96%, 97%, 98% or 99% identity to SEQ ID NO: 7, SEQ ID NO: 9, or SEQ ID NO: 14. In some embodiments, the polynucleotide comprises codon bias for improved expression in a microalgal host cell, e.g., a Prototheca or *Chlorella* microalgal host cell.

In another aspect, provided are expression cassettes comprising a polynucleotide encoding a non-natural or variant β-ketoacyl-ACP synthase (KAS) IVa enzyme (KASIVa), as described above and herein. In another aspect, provided are vectors comprising a polynucleotide encoding a non-natural or variant β-ketoacyl-ACP synthase (KAS) IVa enzyme (KASIVa), as described above and herein or an expression cassette comprising such a polynucleotide. In some embodiments, the vector further comprises a polynucleotide encoding an exogenous lipid biosynthesis enzyme, e.g., fatty acid biosynthesis enzymes and/or triglyceride biosynthesis enzymes. In some embodiments, the encoded thioesterase preferentially hydrolyzes C10-ACP substrates. In some embodiments, the thioesterase is a *Cuphea* FATB thioesterase. In some embodiments, the thioesterase is a *Cuphea* FATB thioesterase selected from the group consisting of *Cuphea hookeriana* FATB2 (ChFATB2), *Cuphea paucipetala* FATB1 (Cpau FATB1), *Cuphea palustris* FATB1 (Cpal FATB1), *Cuphea ignea* FATB1 (Cignea FATB1), *Cuphea avigera* FATB1 (Ca FATB1, *Cuphea painteri* FATB1 (Cpai FATB1), *Cuphea crassiflora* FATB1 (CcrasFATB1), *Cuphea koehneana* FATB3 (CkoeFATB3), *Cuphea leptopoda* FATB1 (CleptFATB1), *Cuphea angustifolia* FATB1 (CangFATB1), *Cuphea llavea* FATB1 (CllaFATB1), and *Cuphea lophostoma* FATB1 (ClopFATB1). In some embodiments, the encoded thioesterase comprises at least about at least about 80%, 85%, 90%, 91%, 92%, 93%, 94%, 95%, 96%, 97%, 98% or 99% identity to amino acid residues 39-392 of SEQ ID NO: 5, wherein the thioesterase catalyzes the production of increased levels of C10 fatty acids and/or has increased specificity for C10 fatty acids in comparison to a wild-type thioesterase.

In a further aspect, provided are non-natural or variant KASIVa polypeptides encoded by the polynucleotides, as described above and herein. In some embodiments, the KASIVa comprises an amino acid sequence of SEQ ID NO: 4, comprising an X at the position corresponding to position 146; wherein X is an amino acid residue selected from the group consisting of glycine (G), asparagine (N), or serine (S). In some embodiments, X is a serine (S) residue. In some embodiments, X is a glycine (G) residue. In some embodiments, X is a asparagine (N) residue. In a further aspect, provided are fusion proteins comprising the non-natural or variant KASIVa as described above and herein, and a heterologous or an exogenous peptide or polypeptide.

In a further aspect, provided are host cells comprising the polynucleotide encoding a non-natural or variant β-ketoacyl-ACP synthase (KAS) IVa enzyme (KASIVa), as described above and herein, an expression cassette and/or a vector comprising such a polynucleotide. In some embodiments, the host cell further comprises a polynucleotide encoding an exogenous lipid biosynthesis enzyme, e.g., a fatty acyl-ACP thioesterase. In some embodiments, the thioesterase preferentially hydrolyzes C10-ACP substrates. In some embodiments, the thioesterase is a *Cuphea* FATB thioesterase. In some embodiments, the thioesterase is a *Cuphea* FATB thioesterase selected from the group consisting of *Cuphea hookeriana* FATB2 (ChFATB2), *Cuphea paucipetala* FATB1 (Cpau FATB1), *Cuphea palustris* FATB1 (Cpal FATB1), *Cuphea ignea* FATB1 (Cignea FATB1), *Cuphea avigera* FATB1 (Ca FATB1, *Cuphea painteri* FATB1 (Cpai FATB1), *Cuphea procumbens* FATB1 (CprocFATB1), *Cuphea procumbens* FATB3 (CprocFATB3), *Cuphea crassiflora* FATB1 (CcrasFATB1), *Cuphea koehneana* FATB3 (CkoeFATB3), *Cuphea leptopoda* FATB1 (CleptFATB1), *Cuphea angustifolia* FATB1 (CangFATB1), *Cuphea llavea* FATB1 (CllaFATB1), and *Cuphea lophostoma* FATB1 (ClopFATB1), *Cuphea* PSR23 FatB3 (CuPSR23FATB3), *Cuphea viscosissima* FatB1 (CvisFATB1), and *Cuphea glossostoma* FatB1 (CgFATB1). In some embodiments, the thioesterase comprises at least about at least about 80%, 85%, 90%, 91%, 92%, 93%, 94%, 95%, 96%, 97%, 98% or 99% identity to amino acid residues 39-392 of SEQ ID NO: 5, wherein the thioesterase has increased activity on a C10-acyl substrate and/or has increased specificity for a C10-acyl substrate (e.g., increases the ratio of C10 fatty acids to the sum of other fatty acids produced) in comparison to a wild-type thioesterase. In some embodiments, one or more endogenous lipid biosynthesis enzymes (e.g., fatty acid biosynthesis enzymes and/or triglyceride biosynthesis enzymes) are selected from the group consisting of a fatty acyl thioesterase A (FATA), a fatty acyl thioesterase B (FATB), a 1-acylglycerol-3-phosphate O-acyltransferase (LPAAT), a glycerol-3-phosphate acyltransferase (GPAT), an acyl CoA:diacylglycerol acyltransferase (DGAT), a fatty acid elongase (FAE) and a long-chain acyl-CoA synthetase (LACS) are deleted, knocked-out or knocked down. In some embodiments, the host cells further comprise one or more exogenous or heterologous lipid biosynthesis enzymes selected from the group consisting of a fatty acyl thioesterase A (FATA), a fatty acyl thioesterase B (FATB), a 1-acylglycerol-3-phosphate O-acyltransferase (LPAAT), a glycerol-3-phosphate acyltransferase (GPAT), an acyl CoA:diacylglycerol acyltransferase (DGAT), and a fatty acid elongase (FAE), a long-chain acyl-CoA synthetase (LACS). In some embodiments, the host cell further comprises one or more exogenous or heterologous enzymes, such as a sucrose invertase and a 4-amino-5-hydroxymethyl-2-methylpyrimidine phosphate synthase (THIC). In some embodiments, the host cell is an oleaginous microbial cell (e.g., oleaginous yeasts, such as *Yarrowia lipolytica*). In some embodiments, the microbial host cell is an oleaginous microalgal cell. In some embodiments, host cell is a heterotrophic microalga, e.g., a obligate heterotrophic microalga. In some embodiments, the host cell is a microalga of the phylum Chlorpophya, e.g., of the class Trebouxiophytae, e.g., of the order Chlorellales, e.g., of the family Chlorellacae, e.g., of the genus *Prototheca* or *Chlorella*, e.g., of a species selected from the group consisting of *Prototheca moriformis, Prototheca krugani, Prototheca stagnora, Prototheca zopfii* and *Chlorella protothecoides*. In some embodiments, the host cell has a fatty acid profile comprising at least 50%, 55%, 60%, 65%, 70%, 75%, 80%, 85%, 90%, or more, C10 fatty acids.

In a further aspect, provided are methods of producing a host cell that produces an oil having a desired fatty acid profile. In some embodiments, the methods comprise transforming a microalgal host cell with a polynucleotide encoding a non-natural or variant β-ketoacyl-ACP synthase (KAS) IVa enzyme (KASIVa), as described above and herein, an expression cassette and/or a vector comprising such a polynucleotide, and cultivating the microalgal host cell so as to produce the oil. In some embodiments, the microalgal host cell produces on oil comprising at least 50%, 55%, 60%, 65%, 70%, 75%, 80%, 85%, 90%, or more, C10 fatty acids. In some embodiments, the microalgal host cell produces an oil with an increase C10 fatty acid level of at least 5%, 10%, 20%, 40%, 50%, 80%, 100%, 200%, or more, in comparison to an untransformed microalga or a microalga transformed with a wild-type acyl-ACP KASIVa. In some embodiments, the microalgal host cell produces an oil with an increase in C10 fatty acid level of at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type acyl-ACP KASIVa. In some embodiments, the oil is a triglyceride oil. In some embodiments, the methods further comprise the step of recovering the oil.

In another aspect, provided are methods of producing an oil comprising predominantly C10 fatty acids. In some embodiments, the methods comprise transforming a host cell with polynucleotide encoding a non-natural or variant β-ketoacyl-ACP synthase (KAS) IVa enzyme (KASIVa), as described above and herein, an expression cassette and/or a vector comprising such a polynucleotide, and cultivating the microalgal host cell so as to produce an oil comprising at least about 50% C10 fatty acids, e.g., at least about 55%, 60%, 65%, 70%, 75%, 80%, 85%, 90%, or more, C10 fatty acids.

In another aspect, provided are methods for increasing the level of C10 fatty acids and/or the ratio of C10 fatty acids to the sum of other fatty acids composing the fatty acid profile of an oil produced by a host cell. In some embodiments, the methods comprise providing a parent gene encoding a KASIVa enzyme, mutating the gene so as to encode a non-natural or variant KASIVa as described above and herein; expressing the mutated gene in the host cell; and producing the oil, whereby the level of C10 fatty acids and/or the ratio of C10 fatty acids to the sum of other fatty acids composing the fatty acid profile of the oil are increased.

With respect to the methods, in some embodiments, the methods comprise co-expressing a polynucleotide encoding an exogenous lipid biosynthesis enzyme, e.g., a fatty acyl-ACP thioesterase. In some embodiments, the thioesterase preferentially hydrolyzes C10-ACP substrates. In some embodiments, the thioesterase is a *Cuphea* FATB thioesterase. In some embodiments, the thioesterase is a *Cuphea* FATB thioesterase selected from the group consisting of *Cuphea hookeriana* FATB2 (ChFATB2), *Cuphea paucipetala* FATB1 (Cpau FATB1), *Cuphea palustris* FATB1 (Cpal FATB1), *Cuphea ignea* FATB1 (Cignea FATB1), *Cuphea avigera* FATB1 (Ca FATB1, *Cuphea painteri* FATB1 (Cpai FATB1)), *Cuphea procumbens* FATB1 (CprocFATB1), *Cuphea procumbens* FATB3 (CprocFATB3), *Cuphea crassiflora* FATB1 (CcrasFATB1), *Cuphea koehneana* FATB3 (CkoeFATB3), *Cuphea leptopoda* FATB1 (CleptFATB1), *Cuphea angustifolia* FATB1 (CangFATB1), *Cuphea llavea* FATB1 (CllaFATB1), and *Cuphea lophostoma* FATB1 (ClopFATB1), *Cuphea* PSR23 FatB3 (CuPSR23FATB3), *Cuphea viscosissima* FatB1 (CvisFATB1), and *Cuphea glos-*

*sostoma* FatB1 (CgFATB1). In some embodiments, the thioesterase comprises at least about at least about 80%, 85%, 90%, 91%, 92%, 93%, 94%, 95%, 96%, 97%, 98% or 99% identity to amino acid residues 39-392 of SEQ ID NO: 5.

With respect to the methods, in some embodiments, the host cell is an oleaginous microbial cell (e.g., oleaginous yeasts, such as *Yarrowia lipolytica*). In some embodiments, the microbial host cell is an oleaginous microalgal cell. In some embodiments, host cell is a heterotrophic microalga, e.g., a obligate heterotrophic microalga. In some embodiments, the host cell is a microalga of the phylum Chlorpophya, e.g., of the class Trebouxiophytae, e.g., of the order Chlorellales, e.g., of the family Chlorellacae, e.g., of the genus *Prototheca* or *Chlorella*, e.g., of a species selected from the group consisting of *Prototheca moriformis*, *Prototheca krugani*, *Prototheca stagnora*, *Prototheca zopfii* and *Chlorella protothecoides*.

In a further aspect, provided is an oil produced by the methods described above and herein. With respect to the oil, in some embodiments, the oil comprises triglycerides, wherein the oil comprises at least about 35%, at least about 40%, at least about 41%, at least 42%, at least about 43%, or at least about 44% tridecanoin. In some embodiments, the oil is a microbial. In some embodiments, the oil comprises about 35% to about 55% of tridecanoin, about 40% to about 50% of tridecanoin, or about 42% to about 47% tridecanoin. In some embodiments, the oil comprises at least about 40%, at least about 45%, at least about 46%, at least about 47%, at least about 48%, at least about 49%, at least about 50%, or at least about 51%, of medium- and long-chain triglyceride (MLCT). In some embodiments, the oil further comprises about 40% to about 60% of medium- and long-chain triglyceride (MLCT), or about 45% to about 55% of MLCT. In some embodiments, about at least about 5% of MLCT, at least about 10% of MLCT, optionally about 10% to about 15% of MLCT, in the oil is caprate-caprate-laurate (Ca-CaLa) triglyceride. In some embodiments, at least about 5% of MLCT, at least about 10% of MLCT, optionally about 10% to about 15% of MLCT, is caprate-oleate-caprate (CaOCa) triglyceride. In some embodiments, at least about 5% of MLCT, optionally about 5% to about 10% of MLCT, is caprate-caprate-palmitate (CaCaP) triglyceride. In some embodiments at least about 3%, at least about 5%, or optionally about 3% to about 8% of MLCT, is a combination of caprate-caprate-myristate (CaCaM) triglyceride and laurate-laurate-caprate (LaLaCa) triglyceride.

In some embodiments, the C10:0 fatty acid content of the oil is at least about 45%, at least about 50%, at least about 55%, at least about 60%, at least about 65%, or at least about 70% of total fatty acids derivable from the oil. In some embodiments, the C10:0 fatty acid content of the oil is about 40% to about 90%, about 50% to about 80%, about 60% to about 75%, or about 65% to about 75%, or about 70% to about 75% of total fatty acids derivable from the oil. In some embodiments, the C8:0 fatty acid content of the oil is present in an amount less than about 5%, less than about 4%, less than about 3%, less than about 2%, or less than 1% of total fatty acids derivable from the oil. In some embodiments, the C12:0 fatty acid content of the oil is present in an amount less than 15%, less than 10%, optionally about 2% to about 10%, of the total fatty acids derivable from the oil. In some embodiments, the C14:0 fatty acid content of the oil is present in an amount less than about 15%, less than about 10%, optionally about 2% to about 10%, of the total fatty acids derivable from the oil. In some embodiments, the oil is obtained from an oleaginous microbial cell. In some embodiments, the oil is obtained from an oleaginous microalga. In some embodiments, the oil further comprises ergosterol. In some embodiments, the oil further comprises additional sterols, wherein the most abundant sterol is ergosterol. In some embodiments, the oil further comprises brassicasterol. In some embodiments, the ratio of ergosterol to brassicasterol in the oil is at least 5:1, 10:1, 15:1 or 20:1. In some embodiments, the oil is a noninteresterified cell oil.

In a further aspect, provided is a product comprising the microbial oil and/or a chemical composition derived from the microbial oil disclosed herein.

Definitions

As used herein, an "acyl-ACP thioesterase," "fatty acyl-ACP thioesterase," "acyl-ACP TE," or "thioesterase." interchangeably refer to an enzyme that catalyzes the cleavage of a fatty acid from an acyl carrier protein (ACP) during lipid synthesis. Acyl-acyl carrier protein (ACP) thioesterases (TEs) hydrolyze acyl-ACP thioester bonds, releasing free fatty acids and ACP.

The term "acyl-ACP preferring TE" refers to the fatty acyl-ACP substrate specificity of a TE. An acyl-ACP preferring TE preferentially liberates a particular fatty acid from an acyl-ACP substrate. For example, the acyl-ACP preferring TE can preferentially liberate a given fatty acid (e.g., C8:0 fatty acids) over all other fatty acids in the set of C8:0, C10:0, C12:0, C14:0, C16:0, C18:0, C18:1, and C18:2 fatty acids. The preference of the acyl-ACP preferring TE can be detected as a higher $V_{max}$ (or a higher $k_{cat}$, or a higher V/K) in comparison to other non-preferred fatty acid-ACP substrates. The preference can be inferred from changes in fatty acid profile of a cell genetically engineered to overexpress the acyl-ACP preferring TE relative to a control cell that does not overexpress the acyl-ACP preferring TE.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

A "variant" is a polypeptide comprising a sequence which differs in one or more amino acid position(s) from that of a parent polypeptide sequence (e.g., by substitution, deletion, or insertion). A variant may comprise a sequence which differs from the parent polypeptides sequence in up to 40% of the total number of residues of the parent polypeptide sequence, such as in up to 40%, 35%, 30%, 25%, 20%, 15%, 10%, 9%, 8%, 7%, 6%, 5%, 4%, 3% 2% or 1% of the total number of residues of the parent polypeptide sequence. For example, a variant of a 400 amino acid polypeptide sequence comprises a sequence which differs in up to 40% of the total number of residues of the parent polypeptide sequence, that is, in up to 160 amino acid positions within the 400 amino acid polypeptide sequence (such as in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 85, 90, 95, 100, 105, 110, 115, 120, 125, 130, 135, 140, 145, 150, 155, or 160 amino acid positions within the reference sequence.

"Naturally occurring" as applied to a composition that can be found in nature as distinct from being artificially produced by man. For example, a polypeptide or polynucleotide that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

A "cell oil" or "cell fat" shall mean a predominantly triglyceride oil obtained from an organism, where the oil has not undergone blending with another natural or synthetic oil, or fractionation so as to substantially alter the fatty acid profile of the oil. "Microbial oil" is to be understood herein as an oil obtained from microbial cells. Preferably, the microbial oil is an oil comprising triglycerides. In connection with an oil comprising triglycerides of a particular regiospecificity, the cell oil or cell fat has not been subjected to interesterification or other synthetic process to obtain that regiospecific triglyceride profile, rather the regiospecificity is produced naturally, by a cell or population of cells. For a cell oil or cell fat produced by a cell, the sterol profile of oil is generally determined by the sterols produced by the cell, not by artificial reconstitution of the oil by adding sterols in order to mimic the cell oil. In connection with a cell oil or cell fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "cell fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

The terms "lipid", "neutral lipid", "triglyceride", "triacylglyceride", "triacylglycerol", "TAG", and "triglyceride oil" are used interchangeably in the present disclosure, except where otherwise noted.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

As used herein, an oil is said to be "enriched" in one or more particular fatty acids if there is at least a 10% increase in the mass of that fatty acid in the oil relative to the non-enriched oil. For example, in the case of a cell expressing a heterologous or exogenous fatty acyl-ACP thioesterase gene described herein, the oil produced by the cell is said to be enriched in, e.g., C10 fatty acids, if the mass of these fatty acids in the oil is at least 10% greater than in oil produced by a cell of the same type that does not express the heterologous or exogenous fatty acyl-ACP thioesterase gene (e.g., wild type oil).

A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

A "triglyceride (TAG) profile" is the area percent distribution of each triglyceride in a triglyceride mixture generated by HPLC with RID (Refractive Index Detector) using AOCS method C3 5c-93, modified to include two columns as described in Example 1. As used herein, a percent of a specific triglyceride (e.g., tridecanoin) refers to the area percent of the triglyceride in a triglyceride mixture distribution, measured by the above method. The area percent of a triglyceride profile is approximately the mole percent distribution of each triglyceride in a triglyceride mixture. Typically, as is the case here, the possible regioisomers derived from having the same two or three different fatty acids at the different positions of the glycerol backbone are not resolved nor distinguished and are grouped and reported as one of the possible TAGs. Thus, in a triglyceride oil containing a mixture of CaOO (caprate-oleate-oleate), OCaO (oleate-caprate-oleate), and OOCa (oleate-oleate-caprate), the percent indicated for one of these TAGs would represent the sum of all possible isomers.

"Medium-long-chain triglyceride" or "MLCT" means a triglyceride, in which at least one medium chain fatty acid having 6 to 10 carbons (C6-C10) and at least one long chain fatty acid having 12 carbons or more are bound to the glycerol backbone.

"Microalgae" are microbial organisms that contain a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include eukaryotic Chlorophyceae such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca* or *Chlorella*.

An "oleaginous" cell is a non-human cell capable of producing at least 20% lipid by dry cell weight, naturally or through recombinant or classical strain improvement. An "oleaginous microbe" or "oleaginous microorganism is a microbe, including a microalga that is oleaginous.

As used with respect to polypeptides or polynucleotides, the term "isolated" refers to a polypeptide or polynucleotide that has been separated from at least one other component that is typically present with the polypeptide or polynucleotide. Thus, a naturally occurring polypeptide is isolated if it has been purified away from at least one other component that occurs naturally with the polypeptide or polynucleotide. A recombinant polypeptide or polynucleotide is isolated if it has been purified away from at least one other component present when the polypeptide or polynucleotide is produced.

The terms "polypeptide" and "protein" are used interchangeably herein to refer a polymer of amino acids, and unless otherwise limited, include atypical amino acids that can function in a similar manner to naturally occurring amino acids.

The term "sequence", as used in connection with a polypeptide or nucleic acid polymer refers to the order of monomers making up the polymer or the sub-polymer or fragment having that sequence.

A "subsequence" of an amino acid or nucleotide sequence is a portion of a larger sequence or the peptide or nucleic acid sub-polymer or fragment characterized by the portion of the larger sequence.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence (e.g., SEQ ID NOs: 1-15), based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use BLASTN program with its default parameters: (General Parameters: Max target sequences: 100; Expect threshold: 10; Word size: 28, Max matches in a query range: 0; Scoring parameters: Match/Mismatch Scores: 1, –2; Gap Costs: linear). For polypeptide sequence alignment and sequence identity calculations, BLASTP program can be used with its default parameters (General Parameters: Max target sequences: 100, Expect threshold: 10; Word size: 6; Max matches in a query range: 0; Scoring Parameters: Matrix=BLOSUM62; Gap costs: Existence=11, Extension=1; Compositional adjustments=Conditional compositional score). In certain embodiments, the sequence identity between two polypeptide sequences is determined using the Needleman-Wunsch algorithm (Needleman and Wunsch, 1970, J. Mol. Biol. 48: 443-453) as implemented in the Needle program of the EMBOSS package (https://www.ebi.ac.uk/Tools/psa/emboss_needle) from the European Bioinformatics Institute, using its default parameters (Matrix: BLOSUM62; Gap Open: 10; Gap Extend: 0.5; End Gap Penalty: false; End Gap Open: 10; End Gap Extend: 0.5). In certain embodiments, the sequence identity between two nucleic acid sequences is determined using the Needleman-Wunsch algorithm described above using its default parameters (Matrix: DNAfull; Gap Open: 10; Gap Extend: 0.5; End Gap Penalty; false; End Gap Open: 10; End Gap Extend: 0.5). In certain embodiments, the sequence alignment of two or more sequences are performed using Clustal Omega or ClustalW using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: aligned).

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

The term "mutation" shall mean a change in a protein, polypeptide, or peptide sequence or subsequence produced by altering one or more nucleotides in a nucleotide coding for the protein, polypeptide, or peptide, however the alteration is obtained. For example, a mutation can be produced randomly, by PCR mutation, by synthesis of entire gene, or any other method.

The term "vector" is used herein to describe a DNA construct containing a polynucleotide. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

As used herein, the terms "expression vector" or "expression construct" or "expression cassette" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. An "expression cassette" includes a coding nucleic acid (CDS) to be transcribed operably linked to a promoter and a 3'UTR. Optionally, and in the Examples below, the promoter of an expression cassette is a heterologous promoter.

"Exogenous gene" refers to a nucleic acid transformed into a cell. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

The term "heterologous" refers to amino acid subsequences that are not encoded by the naturally occurring gene. This can be accomplished in any way known in the art, including, e.g., swapping of individual domains with an altered and/or non-naturally occurring domain, introduction of point mutations, introduction of altered or non-naturally occurring subsequences, or deletion of single amino acid residues, subsequences and/or domains.

An "inducible promoter" is one that mediates transcription of an operably linked gene in response to a particular stimulus.

As used herein, the phrase "in operable linkage" refers to a functional linkage between two sequences, such a control sequence (typically a promoter) and the linked sequence. A promoter is in operable linkage with an exogenous gene if it can mediate transcription of the gene.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "allele" refers to a copy of a gene where an organism has multiple similar or identical gene copies, even if on the same chromosome. An allele may encode the same or similar protein.

As used herein, the term "recombinant" when used with reference, e.g., to a cell, or nucleic acid, protein, or vector, indicates that the cell, nucleic acid, protein or vector, has been modified by the introduction of an exogenous nucleic acid or protein or the alteration of a native nucleic acid or protein, or that the cell is derived from a cell so modified. Thus, recombinant cells express genes that are not found within the native (non-recombinant) form of the cell or express native genes that are otherwise abnormally expressed, over-expressed, under-expressed or not expressed at all. "Recombinant nucleic acid" as used herein refers to nucleic acid molecules that are initially synthesized through the use of laboratory methods, thereby creating nucleic acid sequences that are not normally found in nature. By using laboratory methods, recombinant nucleic acid molecules in operable linkage with different sequences (e.g., promoter, targeting sequence, etc.) is achieved. Thus an isolated nucleic acid, in a linear form, or an expression vector formed in vitro by ligating DNA molecules that are not normally joined, are both considered recombinant. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes herein. Similarly, a "recombinant protein" is a protein made using recombinant techniques, i.e., through the expression of a recombinant nucleic acid as depicted above.

A "transit peptide" is an amino acid sequence that directs the trafficking of a polypeptide fused to the signal sequence. In connection with plastidic cells expressing the polypeptide, the transit peptide may direct trafficking of the polypeptide to the plastid (i.e., a plastid targeting peptide).

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

The term "host cell" refers to a cell capable of maintaining a vector either transiently or stably. Host cells include, without limitation, bacterial cells, yeast cells, insect cells, algal cells (e.g., microalgal cells), plant cells and mammalian cells. Other host cells known in the art, or which become known, are also suitable for use.

DETAILED DESCRIPTION

1. Introduction

Provided are heterologous KAS enzymes that preferentially produce C10:0-ACP to facilitate the production of appreciable capric acid (C10:0) levels in host cells (e.g., microalgal cells such as *Prototheca*). The KAS enzyme variants can coordinate with a heterologous lipid biosynthesis enzyme, e.g., a thioesterase that preferentially hydrolyzes C10:0-acyl ACP substrates into capric acid and acyl carrier proteins (ACPs), so that the resulting capric acid can be incorporated into triglycerides (TAGs). We have previously identified both KAS (CpauKASIVa) gene from *Cuphea paucipetala* that is specific for C10:0 fatty acid production. See Intl. Appl. No. PCT/US15/39951, which is hereby incorporated herein by reference in its entirety. Here, we report on the identification of more active variants, CpauKASIVa$^{T146S}$, CpauKASIVa$^{T146G}$, and CpauKASIVa$^{T146N}$ for strain engineering. By expressing one or more of these variants in combination with a thioesterase gene, the resulting transgenic strains can produce triglyceride oils with fatty acid profiles comprising a high level of C10:0 (e.g., almost 80% C10:0).

2. KASIVa Variants

The variant β-ketoacyl-ACP synthase (KAS) IVa enzymes (KASIVa) can be used in genetic constructs and genetically engineered oleaginous cells (e.g., plants, algae, microalgae) with one or more exogenous genes to produce fatty acids, acylglycerides, or derivatives thereof. For example, microalgae or oilseed crops that would naturally, or through genetic modification, produce high levels of triglycerides can be engineered (or further engineered) to express an exogenous variant KASIVa, which can catalyze the elongation of a medium-chain fatty acyl-ACP, e.g., from C8 to C10, preferentially produce C10:0-ACP, and/or facilitate the production of increased levels of C10 fatty acids, e.g., in comparison to a wild-type KASIVa. The fatty acids synthesized may be incorporated into acyl glycerides including triacylglycerides (TAGs, triglycerides). The triglycerides can be recovered or, through further enzymatic processing within the cell, or in vitro, yield other useful compounds.

Generally, the variant KASIVa enzymes described herein have preferential substrate specificity for medium-chain ACP-fatty acyl substrates (e.g., to promote the production of C8, C10, and/or C12, and/or C14 fatty acids, particularly C10 fatty acids). The variant KASIVa enzymes described herein catalyze the elongation of growing medium-chain fatty acyl-ACP, e.g., from 4 to 12 carbon atoms in length, particularly from 8 to 10 carbon atoms in length, and are categorized as EC 2.3.1.41 (β-ketoacyl-acyl-carrier-protein (ACP) synthase I).

In some embodiments, the non-natural or variant β-ketoacyl-ACP synthase (KAS) IVa enzymes (KASIVa) comprise at least about 80%, 85%, 90%, 91%, 92%, 93%, 94%, 95%, 96%, 97%, 98% or 99% identity to amino acid residues 34-523 of SEQ ID NO: 4 and comprises an X at the position corresponding to position 146; wherein X is an amino acid residue selected from the group consisting of glycine (G), asparagine (N), or serine (S), wherein the positions are with reference to SEQ ID NO: 4. In some embodiments, the X at position 146 is serine (S). In some embodiments, the X at position 146 is glycine (G). In some embodiments, the X at position 146 is asparagine (N).

In some embodiments, the non-natural or variant β-ketoacyl-ACP synthase (KAS) IVa enzyme (KASIVa) is encoded by a polynucleotide comprising at least about 80%, 85%, 90%, 91%, 92%, 93%, 94%, 95%, 96%, 97%, 98% or 99% identity to nucleic acid residues 100-1563 of SEQ ID NO: 7, SEQ ID NO: 9, or SEQ ID NO: 14. In some embodiments, the non-natural or variant β-ketoacyl-ACP synthase (KAS) IVa enzyme (KASIVa) is encoded by a polynucleotide comprising at least about 80%, 85%, 90%, 91%, 92%, 93%, 94%, 95%, 96%, 97%, 98% or 99% identity to SEQ ID NO: 7, SEQ ID NO: 9, or SEQ ID NO: 14.

In certain embodiments, provided is a fragment any of the above-described proteins or nucleic acids (including fragments of protein or nucleic acid variants), wherein the protein fragment has activity, e.g., to catalyze the elongation of a medium-chain fatty acyl-ACP, e.g., from C8 to C10, preferentially produce C10:0-ACP, and/or facilitate the production of increased levels of C10 fatty acids, e.g., in comparison to a wild-type KASIVa. Also contemplated are nucleic acid fragments encoding such protein fragments. In other embodiments, the fragment includes a domain of an acyl-ACP thioesterase that mediates a particular function, e.g., elongation of C8 to C10 fatty acids. Illustrative fragments can be produced by C-terminal and/or N-terminal truncations and include at least 50%, 55%, 60%, 65%, 70%, 75%, 80%, 85%, 90%, 95%, 96%, 97%, 98%, or 99% of the full-length sequences disclosed herein.

3. Co-Expression with C10-Preferring Thioesterases

In some embodiments, the variant KASIVa enzyme is co-expressed with a heterologous or exogenous fatty acyl-ACP thioesterase. In some embodiments, the thioesterase preferentially hydrolyzes C10-ACP substrates, e.g., catalyzes the production of increased levels of C10 fatty acids and/or has increased specificity for C10 fatty acids in comparison to a wild-type thioesterase. Illustrative C10-preferring thioesterases of use for co-expression include without limitation FATB from *Lythraceae* species, e.g., FATB from *Cuphea* species, including, e.g., *Cuphea hookeriana* FATB2 (ChFATB2), *Cuphea paucipetala* FATB1 (Cpau FATB1), *Cuphea palustris* FATB1 (Cpal FATB1, e.g., accession AAC49179), *Cuphea ignea* FATB1 (Cignea FATB1), *Cuphea avigera* FATB1 (Ca FATB1) (including K228M and K228I variants), *Cuphea painteri* FATB1 (Cpai FATB1), *Cuphea procumbens* FATB1 (CprocFATB1), *Cuphea procumbens* FATB3 (CprocFATB3), *Cuphea crassiflora* FATB1 (CcrasFATB1), *Cuphea koehneana* FATB3 (CkoeFATB3), *Cuphea leptopoda* FATB1 (CleptFATB1), *Cuphea angustifolia* FATB1 (CangFATB1), *Cuphea llavea* FATB1 (CllaFATB1), *Cuphea lophostoma* FATB1 (Clop-FATB1), *Cuphea* PSR23 FatB3 (CuPSR23FATB3), *Cuphea viscosissima* FatB1 (CvisFATB1), and *Cuphea glossostoma* FatB1 (CgFATB1) and FATB thioesterases, variants, deletion mutants and chimeras described in, e.g., WO 2014/120829, WO 2014/151904, WO 2016/014968, and WO2016/044779, which are hereby incorporated herein by reference in their entireties for all purposes. A consensus C10:0 specific thioesterase sequence is provided in WO 2014/151904.

As disclosed in PCT/US2014/013676, we discovered that grafting the *Cuphea avigera* FATB1 (Ca FATB1) N-terminal specificity domain onto the *Cuphea hookeriana* FATB2 improves activity and C8-C10 ratio. *Prototheca moriformis* transfomants expressing Ch FATB2 H163Y, L186P (D3130) mutants exhibited about 2 fold increase in the average C8-C10 sum as well as a shift in fatty acid profile specificity relative to the wild-type Ch FATB2 (D3042).

In some embodiments, the encoded thioesterase comprises at least about 80%, 85%, 90%, 91%, 92%, 93%, 94%, 95%, 96%, 97%, 98% or 99% identity to amino acid residues 39-392 of SEQ ID NO: 5.

4. Co-Expression with Other Lipid Biosynthesis Enzymes

In some embodiments, the variant KASIVa enzyme is co-expressed with one or more heterologous or exogenous lipid biosynthesis enzymes. In some embodiments, the variant KASII enzyme is co-expressed with one or more heterologous or exogenous lipid biosynthesis enzymes selected from the group consisting of a fatty acyl thioesterase A (FATA), a fatty acyl thioesterase B (FATB), a 1-acylglycerol-3-phosphate O-acyltransferase (LPAAT), a glycerol-3-phosphate acyltransferase (GPAT), an acyl CoA:diacylglycerol acyltransferase (DGAT), and a fatty acid elongase (FAE), a long-chain acyl-CoA synthetase (LACS). In some embodiments, the host cell further comprises one or more exogenous or heterologous enzymes, such as a sucrose invertase and a 4-amino-5-hydroxymethyl-2-methylpyrimidine phosphate synthase (THIC). Recombinant expression of heterologous or exogenous lipid biosynthesis enzymes is described, e.g., in U.S. Patent Publ. No. 2014/0178950, which is incorporated herein by reference in its entirety for all purposes. For example, one or more polynucleotides encoding one or more of the aforementioned lipid biosynthesis enzymes can be used in a variety of genetic constructs including plasmids or other vectors for expression or recombination in a host cell. The genes can be codon optimized for expression in a target host cell. The genes can be included in an expression cassette that includes a promoter (e.g., a heterologous promoter) and downstream regulatory element. The vector can include flanking sequences for homologous recombination. For example, the vector can cause insertion into a chromosome of the host cell, where it can be stably expressed. The proteins produced by the genes can be used in vivo or in purified form. In an embodiment, an expression cassette comprises a homologous promoter, a CDS operable to express one or more lipid biosynthesis enzymes and a 3'UTR. The 3'UTR can comprise a polyadenylation site.

In some embodiments, one or more lipid biosynthesis enzymes endogenous to the host cell selected from the group consisting of a fatty acyl thioesterase A (FATA), a fatty acyl thioesterase B (FATB), a 1-acylglycerol-3-phosphate O-acyltransferase (LPAAT), a glycerol-3-phosphate acyltransferase (GPAT), an acyl CoA:diacylglycerol acyltransferase (DGAT), a fatty acid elongase (FAE) and a long-chain acyl-CoA synthetase (LACS) are deleted, knocked out or knocked down. For example, one or more polynucleotides encoding one or more of the aforementioned lipid biosynthesis enzymes can also be used to prepare antisense, or inhibitory RNA (e.g., RNAi or hairpin RNA) to inhibit complementary genes in the microalgal host cell. For example, armed with the knowledge of a gene sequence encoding one of the aforementioned proteins, one can engineer a microalgal host cells with the same or similar gene to express an RNAi construct, gene knockout, knockdown, point mutation, or the like, and thereby reduce the expression and/or activity of one or more of the enzymes in the microalgal host cell. As a result, the microalgae can produce an oil with an altered fatty acid profile in which the mean chain length is decreased or increased, depending on the presence of other fatty acid synthesis genes. In some embodiments, a mutation (including knockout) or inhibition (e.g., using antisense or RNAi) of one or more endogenous desaturase genes (e.g., a stearoyl-ACP desaturase or fatty acid desaturase including a delta 12 fatty acid desaturase) can reduce or eliminate desaturase activity to produce a more fully saturated triglyceride profile.

Depending on the desired properties of the triglyceride molecule to be produced, one or more genes encoding enzymes that utilize fatty acids or fatty acyl molecules as substrates to produce triglyceride molecules may be attenuated or over-expressed in the host cell (e.g., microalga), for example using RNAi, hairpin constructs, knockdowns, double or single knockouts or replacement (e.g., replacing an endogenous gene with a heterologous gene).

5. Codon-Bias for Improved Expression in Microalgal Host Cells

DNA encoding a polypeptide to be expressed in a microorganism, e.g., a KASIVa variant, optionally with an exogenous lipid biosynthesis enzyme, e.g., a fatty acyl-ACP thioesterase, and selectable marker can be codon-optimized cDNA. Methods of recoding genes for expression in microalgae are described in U.S. Pat. No. 7,135,290. Additional information for codon optimization is available, e.g., at the Codon Usage Database at kazusa.or.jp/codon/. The table for *Prototheca* preferred codon usage is also provided in U.S. Patent Publ. No. 2012/0283460. Preferred codon usage in *Prototheca* and *Chlorella protothecoides* is provided in Tables A and B.

TABLE A

| Preferred codon usage in *Prototheca* strains | | |
| --- | --- | --- |
| Amino Acid | Codon | Usage Frequency |
| Ala | GCG | 36% |
| | GCA | 7% |
| | GCT | 11% |
| | GCC | 46% |
| Arg | AGG | 6% |
| | AGA | 2% |
| | CGG | 18% |
| | CGA | 8% |
| | CGT | 9% |
| | CGC | 57% |
| Asn | AAT | 4% |
| | AAC | 96% |
| Asp | GAT | 12% |
| | GAC | 88% |
| Cys | TGT | 10% |
| | TGC | 90% |
| Gln | CAG | 82% |
| | CAA | 18% |
| Glu | GAG | 96% |
| | GAA | 4% |
| Gly | GGG | 12% |
| | GGA | 7% |
| | GGT | 10% |
| | GGC | 71% |
| His | CAT | 21% |
| | CAC | 79% |
| Ile | ATA | 1% |
| | ATT | 8% |
| | ATC | 91% |
| Lys | AAG | 98% |
| | AAA | 2% |
| Leu | TTG | 4% |
| | TTA | 0% |
| | CTG | 61% |
| | CTA | 3% |
| | CTT | 6% |
| | CTC | 26% |
| Met | ATG | 100% |
| Phe | TTT | 29% |
| | TTC | 71% |
| Pro | CCG | 29% |
| | CCA | 9% |
| | CCT | 13% |
| | CCC | 49% |
| Ser | AGT | 3% |
| | AGC | 22% |
| | TCG | 28% |
| | TCA | 6% |
| | TCT | 10% |
| | TCC | 31% |
| Thr | ACG | 38% |
| | ACA | 5% |

TABLE A-continued

| Preferred codon usage in *Prototheca* strains | | |
| --- | --- | --- |
| Amino Acid | Codon | Usage Frequency |
| | ACT | 5% |
| | ACC | 52% |
| Tyr | TAT | 5% |
| | TAC | 95% |
| Trp | TGG | 100% |
| Val | GTG | 50% |
| | GTA | 1% |
| | GTT | 6% |
| | GTC | 43% |
| Stop | | TGA/TAG/TAA |

TABLE B

| Preferred codon usage in *Chlorella protothecoides.* | |
| --- | --- |
| Amino Acid | Preferred Codon |
| Arg | CGC |
| Ala | GCC |
| Asn | AAC |
| Asp | GAC |
| Cys | TGC |
| Gln | CAG |
| Glu | GAG |
| Gly | GGC |
| His | CAC |
| Ile | ATC |
| Leu | CTG |
| Lys | AAG |
| Met | ATG |
| Phe | TTC |
| Pro | CCC |
| Ser | TCC |
| Thr | ACC |
| Trp | TGG |
| Tyr | TAC |
| Val | GTG |
| Stop | TGA |

In various embodiments, the nucleic acids encoding the KASIVa variants, and optionally the co-expressed exogenous lipid biosynthesis enzyme, e.g., fatty acyl-ACP thioesterase, can be codon biased for improved expression in a target host cell. For expression in a *Prototheca* or a *Chlorella* host cell, the encoding polynucleotide can be recoded, using the preferred codons identified in Tables A or B, respectively. For example, in some embodiments, at least 60%, 65%, 70%, 75%, 80%, 85%, 90%, 95%, or 100% of the codons used in the encoding polynucleotide can be the most preferred codon according to Tables A or B. In some embodiments, at least 60%, 65%, 70%, 75%, 80%, 85%, 90%, 95%, or 100% of the codons used in the encoding polynucleotide can be the first or second most preferred codon according to Tables A and B. In some embodiments, the non-natural or variant β-ketoacyl-ACP synthase (KAS) IVa enzyme (KASIVa) is encoded by a polynucleotide comprising at least about 80%, 85%, 90%, 91%, 92%, 93%, 94%, 95%, 96%, 97%, 98% or 99% identity to nucleic acid residues 100-1563 of SEQ ID NO: 7, SEQ ID NO: 9, or SEQ ID NO: 14. In some embodiments, the non-natural or variant β-ketoacyl-ACP synthase (KAS) IVa enzyme (KASIVa) is encoded by a polynucleotide comprising at least about 80%, 85%, 90%, 91%, 92%, 93%, 94%, 95%, 96%, 97%, 98% or 99% identity to SEQ ID NO: 7, SEQ ID NO: 9, or SEQ ID NO: 14.

6. Expression and Targeting to Plastids

Heterologous or exogenous proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors described herein, e.g., to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella prototh-ecoides* cells and are described in the Examples of U.S. Patent Publ. No. 2012/0283460 and in PCT Application No. PCT/US2009/066142. Amino acid sequences of the algal plastid targeting sequences identified from the cDNA librar-ies useful plastid targeting of recombinantly expressed vari-ant KASIV enzymes are provided in U.S. Patent Publ. No. 2012/0283460 and herein. In some embodiments, the plastid transit peptide comprises an amino acid sequence selected from the group consisting of MATASTFSAFNAR-CGDLRRSAGSGPRRPARPLPVRGRA (SEQ ID NO: 10), SGPRRPARPLPVR (SEQ ID NO: 16), SGPRRPAR-PLPVRAAIASEVPVATTSPR (SEQ ID NO: 17), RPAR-PLPVRGRA (SEQ ID NO: 18), RPARPLPVRAAIASEVP-VATTSPR (SEQ ID NO: 19), RCGDLRRSA-GSGPRRPARPLPVRGRA (SEQ ID NO: 20), RCGDLRR-SAGSGPRRPARPLPVRAAIASEVPVATTSPR (SEQ ID NO: 21), PARPLPVR (SEQ ID NO: 22), PARPLPVRAA-IASEVPVATTSPR (SEQ ID NO: 23), RRPARPLPVR (SEQ ID NO: 24), and RRPARPLPVRAAIASEVPVATT-SPR (SEQ ID NO: 25). In some embodiments, the plastid transit peptide comprises at least about 80%, 85%, 90%, 91%, 92%, 93%, 94%, 95%, 96%, 97%, 98% or 99% identity to amino acid residues 1-33 of SEQ ID NO: 3, amino acid residues 1-33 of SEQ ID NO: 4, SEQ ID NO: 10 or SEQ ID NO: 11. In some embodiments, the plastid transit peptide is encoded by a polynucleotide comprising at least about 80%, 85%, 90%, 91%, 92%, 93%, 94%, 95%, 96%, 97%, 98% or 99% identity to SEQ ID NO: 12.

Where novel KASIV variants are disclosed here, it will be understood that a variety of heterologous plastid transit peptides can be used. In other words, the non-targeting peptide domain is more highly conserved. Accordingly, embodiments described herein feature the novel KASIV enzymatic domain with or without a plastid targeting sequence. For example, where a percent identity to a novel KASIV gene is given herein, the same identity can be applied (where specified) to the same sequence absent the targeting peptide. A substitute targeting peptide can option-ally be used in connection with such a sequence.

7. Host Cells

Any species of organism that produces suitable lipids or triglycerides can be used, although microorganisms that naturally produce high levels of suitable triglycerides are preferred. Considerations for the selection of microorgan-isms include, in addition to production of suitable lipids or triglycerides for production of oils and oleochemicals: (1) high lipid content as a percentage of dry cell weight; (2) ease of growth; (3) ease of genetic engineering; and (4) ease of biomass processing. In particular embodiments, the wild-type, classically improved or genetically engineered micro-organism yields cells that are at least 40%, at least 45%, at least 50%, at least 55%, at least 60%, at least 65%, or at least 70% or more lipid as a percentage of their dry cell weight. Preferred organisms grow heterotrophically (on sugars in the absence of light) or can be engineered to do so using, for example, methods disclosed herein. The ease of transforma-tion and availability of selectable markers and promoters, constitutive or inducible, that are functional in the microor-ganism affect the ease of genetic engineering. Examples of selectable markers useful in microalgae include sucrose invertase, alpha galactosidase (for selection on melibiose) and antibiotic resistance genes. Processing considerations can include, for example, the availability of effective means for lysing the cells.

Microalgae

In some embodiments, the microorganism is a microalga. Non-limiting examples of microalgae that can be used for expression of variant KASIV enzymes include, e.g., *Ach-nanthes orientalis*, *Agmenellum*, *Amphiprora hyaline*, *Amphora coffeiformis*, *Amphora coffeiformis linea*, *Amphora coffeiformis punctata*, *Amphora coffeiformis tay-lori*, *Amphora coffeiformis tenuis*, *Amphora delicatissima*, *Amphora delicatissima capitata*, *Amphora* sp., *Anabaena*, *Ankistrodesmus*, *Ankistrodesmus falcatus*, *Boekelovia hooglandii*, *Borodinella* sp., *Botryococcus braunii*, *Botryo-coccus sudeticus*, *Bracteococcus minor*, *Bracteococcus medionucleatus*, *Carteria*, *Chaetoceros gracilis*, *Chaeto-ceros muelleri*, *Chaetoceros muelleri subsalsum*, *Chaeto-ceros* sp., *Chlorella anitrata*, *Chlorella Antarctica*, *Chlorella aureoviridis*, *Chlorella candida*, *Chlorella capsulate*, *Chlo-rella desiccate*, *Chlorella ellipsoidea*, *Chlorella emersonii*, *Chlorella fusca*, *Chlorella fusca* var. *vacuolata*, *Chlorella glucotropha*, *Chlorella infusionum*, *Chlorella infusionum* var. *actophila*, *Chlorella infusionum* var. *auxenophila*, *Chlo-rella kessleri*, *Chlorella lobophora* (strain *SAG* 37.88), *Chlorella luteoviridis*, *Chlorella luteoviridis* var. *aureo-viridis*, *Chlorella luteoviridis* var. *lutescens*, *Chlorella mini-ata*, *Chlorella minutissima*, *Chlorella mutabilis*, *Chlorella nocturna*, *Chlorella ovalis*, *Chlorella parva*, *Chlorella pho-tophila*, *Chlorella pringsheimii*, *Chlorella protothecoides* (including any of UTEX strains 1806, 411, 264, 256, 255, 250, 249, 31, 29, 25), *Chlorella protothecoides* var. *acidi-cola*, *Chlorella regularis*, *Chlorella regularis* var. *minima*, *Chlorella regularis* var. *umbricata*, *Chlorella reisiglii*, *Chlo-rella saccharophila*, *Chlorella saccharophila* var. *ellipsoi-dea*, *Chlorella salina*, *Chlorella simplex*, *Chlorella sorokini-ana*, *Chlorella* sp., *Chlorella sphaerica*, *Chlorella stigmatophora*, *Chlorella vanniellii*, *Chlorella vulgaris*, *Chlorella vulgaris* F. *tertia*, *Chlorella vulgaris* var. *auto-trophica*, *Chlorella vulgaris* var. *viridis*, *Chlorella vulgaris* var. *vulgaris*, *Chlorella vulgaris* var. *vulgaris f tertia*, *Chlo-rella vulgaris* var. *vulgaris f viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cri-cosphaera* sp., *Crypthecodinium cohnii*, *Cryptomonas* sp., *Cyclotella cryptica*, *Cyclotella meneghiniana*, *Cyclotella* sp., *Dunaliella* sp., *Dunaliella bardawil*, *Dunaliella biocu-lata*, *Dunaliella granulate*, *Dunaliella maritime*, *Dunaliella minuta*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertio-lecta*, *Eremosphaera viridis*, *Eremosphaera* sp., *Ellipsoidon* sp., *Euglena*, *Franceia* sp., *Fragilaria crotonensis*, *Fragi-laria* sp., *Gleocapsa* sp., *Gloeothamnion* sp., *Hymenomonas* sp., *Isochrysis aff galbana*, *Isochrysis galbana*, *Lepocinclis*, *Micractinium*, *Micractinium* (UTEX LB 2614), *Monoraphidium minutum*, *Monoraphidium* sp., *Nannochlo-*

*ris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, ParaChlorella kessleri, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, PseudoChlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

Illustrative host cells feature oleaginous cells that yield altered fatty acid profiles and/or altered regiospecific distribution of fatty acids in glycerolipids and products produced by the cells. Examples of oleaginous cells include microbial cells having a type II lipid biosynthesis pathway, including plastidic oleaginous cells such as those of oleaginous algae. Specific examples of cells include heterotrophic or obligate heterotophic microalgae of the phylum Chlorpophya, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca,* a genus comprising obligate heterotrophs. The oleaginous cells can be, for example, capable of producing 25, 30, 40, 50, 60, 70, 80, 85, or about 90% lipid by cell weight, ±5%. The above mentioned publications also disclose methods for cultivating such cells and extracting oil, especially from microalgal cells; such methods are applicable to the cells disclosed herein. In any of the embodiments described herein, the cells can be heterotrophic cells comprising an exogenous sucrose invertase gene so as to allow the cells to produce oil from a sucrose feedstock.

Illustrative embodiments of host cells include recombinant oleaginous cells expressing one or more exogenous genes encoding fatty acid or triacylglyceride biosynthesis enzymes. As a result, some embodiments feature natural oils never before obtainable in a natural oil. In some cases, the natural oils were not obtainable from a non-plant or non-seed oil, or not obtainable at all.

The oleaginous cells produce a storage oil, which may be stored in storage vesicles of the cell. A raw oil may be obtained from the cells by disrupting the cells and isolating the oil. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride cell oil is given, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). Because the cells are oleaginous, in some cases the storage oil will constitute the bulk of all the triglycerides in the cell.

In some embodiments, the host cell is a plastidic cell, e.g., a heterotrophic microalga of the phylum Chlorpophya, the class Trebouxiophytae, the order Chlorellales, or the family Chlorellacae. In some embodiments, the cell is oleaginous and capable of accumulating at least 40% lipid by dry cell weight. The cell can be an obligate heterotroph, such as a species of *Prototheca,* including *Prototheca* moriformis or *Prototheca zopfii.* The nucleic acid encoding the variant KASIV enzymes described herein can also be expressed in autotrophic algae or plants. Optionally, the cell is capable of using sucrose to produce oil and a recombinant invertase gene may be introduced to allow metabolism of sucrose, as described in PCT Publications WO2008/151149, WO2010/06032, WO2011/150410, WO2011/150411, and international patent application PCT/US12/23696. The invertase may be codon-biased and integrated into a chromosome of the cell, as may all of the genes mentioned here. Codon usage for different algal and plant species of interest is known in the art and can be found, e.g., on the internet at the Codon Usage Database at kazusa.or.jp/codon/.

The polynucleotides encoding the variant KASIV described herein further can be expressed in a wide variety of plant and microalgal host cells. Of particular interest are plant cells of plants involved in the production of vegetable oils for edible and industrial uses, including e.g., temperate oilseed crops. Plants of interest include, but are not limited to, rapeseed (Canola and High Erucic Acid varieties), sunflower, safflower, cotton, *Cuphea,* soybean, peanut, coconut and oil palms, and corn. See, U.S. Pat. Nos. 5,850,022; 5,723,761; 5,639,790; 5,807,893; 5,455,167; 5,654,495; 5,512,482; 5,298,421; 5,667,997; and 5,344,771; 5,304,481.

8. Methods of Culturing Microorganisms

Microorganisms are cultured both for purposes of conducting genetic manipulations and for subsequent production of oil or triglycerides (TGs, triacylglycerols, TAGs, or triacylglycerides). The former type of culture is conducted on a small scale and initially, at least, under conditions in which the starting microorganism can grow. For example, if the starting microorganism is a photoautotroph the initial culture is conducted in the presence of light. The culture conditions can be changed if the microorganism is evolved or engineered to grow independently of light. Culture for purposes of oil or triglyceride production is usually conducted on a large scale. Preferably a fixed carbon source is present. The culture can also be exposed to light some or all of the time.

Microalgae can be cultured in liquid media. The culture can be contained within a bioreactor. Optionally, the bioreactor does not allow light to enter. Alternatively, microalgae can also be cultured in photobioreactors that contain a fixed carbon source and allow light to strike the cells. Exposure of microalgae cells to light, even in the presence of a fixed carbon source that the cells transport and utilize (i.e., mixotrophic growth), nonetheless accelerates growth compared to culturing cells in the dark. Culture condition parameters can be manipulated to increase or improve total triglyceride production, the combination of triglyceride species produced, and/or production of a triglyceride species. In some instances it is preferable to culture cells in the dark, such as, for example, when using extremely large (e.g., 10,000 L, 40,000 L, 100,000 L, 500,000 L, or larger, bioreactors) fermentors that do not allow light to strike the culture.

Microalgal culture media typically contain components such as a fixed nitrogen source, trace elements, vitamins (e.g., thiamine), optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2 \cdot 6H_2O$, $CuCl_2 \cdot 2H_2O$, $MnCl_2 \cdot 4H_2O$ and $(NH_4)_6Mo_7O_{24} \cdot 4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, and/or glucuronic acid. The one or more carbon source(s) can be supplied at a concentration of at least about 50 μM, at least about 100 μM, at least about 500 μM, at least about 5 mM, at least about 50 mM, and at least about 500 mM, of one or more exogenously provided fixed carbon source(s). Some microalgae species can grow by utilizing a fixed carbon source such as glucose or acetate in the absence of light. Such growth is known as heterotrophic growth. For *Chlorella* and/or *Prototheca*, for example, heterotrophic growth results in high production of biomass and accumulation of high lipid content in cells.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. The sewage component serves as a nutrient source in the production of triglycerides, and the culture provides an inexpensive source of triglycerides.

Other culture parameters can also be manipulated, such as the pH of the culture media, the identity and concentration of trace elements and other media constituents.

Heterotrophic Growth

As an alternative to photosynthetic growth of microorganisms, some microorganisms can be cultured under heterotrophic growth conditions in which a fixed carbon source provides energy for growth and lipid accumulation.

Provided are significantly improved culture parameters incorporating the use of glycerol for fermentation of multiple genera of both eukaryotic and prokaryotic microbes, including microbes of the genera *Prototheca, Chlorella, Navicula, Scenedesmus,* and *Spirulina*. Standard methods for the growth and propagation of *Chlorella* and/or *Prototheca* are known (see for example Miao and Wu, J. Biotechnology, 2004, 11:85-93 and Miao and Wu, Biosource Technology (2006) 97:841-846). In addition, multiple species of *Chlorella* and/or *Prototheca* and multiple strains within a species can be grown, e.g., in the presence of a sugar (e.g., glucose, sucrose, xylose) and/or glycerol, including glycerol byproduct from biodiesel transesterification.

For oil production, cells, including recombinant cells described herein, are preferably cultured or fermented in large quantities. The culturing may be in large liquid volumes, such as in suspension cultures as an example. Other examples include starting with a small culture of cells which expand into a large biomass in combination with cell growth and propagation as well as oil production. Bioreactors or steel fermentors can be used to accommodate large culture volumes. A fermentor similar to those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other starch (polymerized glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of oil-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

Oil production by cells disclosed herein can occur during the log phase or thereafter, including the stationary phase wherein nutrients are supplied, or still available, to allow the continuation of oil production in the absence of cell division.

In some embodiments, microorganisms grown using conditions described herein and comprise at least about 20% by weight of lipid, preferably at least about 40% by weight, at least about 50% by weight, and more preferably at least about 60% by weight, even more preferably at least about 70%, 75%, 80% or 85% by weight.

In one heterotrophic growth method, sucrose, produced by example from sugar cane or sugar beet, is used as a feedstock. Oil production can be facilitated or made more efficient through the engineering of microbes such as *Chlorella* and/or *Prototheca*, to utilize sucrose as a carbon source. For example, expression of a sucrose transporter and a sucrose invertase allows *Chlorella* and/or *Prototheca* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable sucrose invertases are Genbank accession numbers CAB95010, NP012104 and CAA06839. Examples of suitable fructokinases are Genbank accession numbers P26984, P26420 and CAA43322. Vectors for transformation of microalgae, including *Chlorella* and/or *Prototheca*, encoding one or more of such genes can be designed as described herein.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. For example, expression of a sucrose invertase with a secretion signal generates invertase activity outside the cell. See Hawkins et al., Current Microbiology Vol. 38 (1999), pp. 335-341 for examples of secretion signals active in *Chlo-*

*rella* and/or *Prototheca*. Expression of such a protein, as enabled by the genetic engineering methodology disclosed herein, allows cells already capable of utilizing extracellular glucose as an energy source to utilize sucrose as an extracellular energy source. *Chlorella* and/or *Prototheca* cells can use both extracellular fructose and extracellular glucose as an energy source, secretion of an invertase can provide the sole catalytic activity necessary for use of sucrose as an efficient, inexpensive energy source.

For example, *Chlorella* and/or *Prototheca* cells can be engineered with a sucrose invertase gene under the regulatory control of one of three promoters (Cauliflower mosaic virus 35S promoter (CMV), *Chlorella* virus promoter (CV), or *Chlorella* HUP1 promoter (HUP 1)). The sucrose invertase gene used in this example comprises codon-bias to the *S. cerevisiae* SUC2 gene to improve expression in a *C. protothecoides* host cell. Expression of a secretable sucrose invertase, such as that described herein, permits the use of molasses, sugar cane juice, and other sucrose-containing feedstocks for cell fermentation.

Alternatively, a sucrose invertase can also be expressed intracellularly in cells that express a sucrose transporter, as well as in cells that express any carbohydrate transporter that allows sucrose to enter the cell.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and/or lipid production. Additionally, conditions and heterotrophic growth methods are useful in the selection and/or genetic engineering of microbes, such as microalgae, to produce microbes that are even more suitable for use in the above-described methods. For example, the microbes having a greater ability to utilize any of the above-described feedstocks for increased proliferation and/or lipid (e.g., fatty acid) production are within the scope of the compositions and methods described herein.

Growth Media

Microorganisms useful in accordance with the methods described herein are found in various locations and environments throughout the world. As a consequence of their isolation from other species and their resulting evolutionary divergence, the particular growth medium for optimal growth and generation of triglyceride constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at utex.org/, a site maintained by the University of Texas at Austin for its culture collection of algae (UTEX). For example, various fresh water and salt water media are provided in U.S. Patent Publ. No. 2012/0288930, hereby incorporated herein by reference in its entirety for all purposes.

In a particular example, a medium suitable for culturing *Chlorella* and/or *Prototheca* cells comprises Proteose Medium. This medium is suitable for axenic cultures, and a 1 L volume of the medium (pH .about.6.8) can be prepared by addition of 1 g of proteose peptone to 1 liter of Bristol Medium. Bristol medium comprises 2.94 mM $NaNO_3$, 0.17 mM $CaCl_2 2H_2O$, 0.3 mM $MgSO_4 7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use.

Other suitable media for use with the methods described herein can be readily identified by consulting the URL identified above, or by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany (ccala.butbn.cas.cz/, Czech Republic).

Increasing Production of Lipids

Process conditions can be adjusted to increase the production of lipids suitable for a particular use and/or to reduce production cost. For example, in certain embodiments, an oleaginous cell (e.g., a plant, an algae, a microalga) is cultured in the presence of a limiting concentration of one or more nutrients, such as, for example, carbon and/or nitrogen, phosphorous, or sulfur, while providing an excess of fixed carbon energy such as glucose. Nitrogen limitation tends to increase microbial lipid production over microbial lipid production in a culture in which nitrogen is provided in excess. In particular embodiments, the increase in lipid production is at least about: 10%, 20%, 30%, 40%, 50%, 75%, 100%, 200%, 300%, 400%, or 500%. The oleaginous cells (e.g., plant cells, algae cells, microalgal cells) can be cultured in the presence of a limiting amount of a nutrient for a portion of the total culture period or for the entire period. In particular embodiments, the nutrient concentration is cycled between a limiting concentration and a non-limiting concentration at least twice during the total culture period.

In another embodiment, lipid production is increased by culturing oleaginous cells or an oleaginous organism (e.g., plants, algae, microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) production over microbial lipid production in the absence of the cofactor(s). In a particular embodiment, the cofactor(s) are provided to the culture by including in the culture oleaginous cells (e.g., plant cells, algae cells, microalgae cells) containing an exogenous gene encoding the cofactor(s). Alternatively, cofactor(s) may be provided to a culture by including an oleaginous cell (e.g., a plant, an algae, a microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the present compositions and methods or that participate in the synthesis of such cofactors are well known and can be introduced into oleaginous cells (e.g., plant cells, algae cells, microalgal cells), using constructs and techniques such as those described above and herein.

In some embodiments, the cells can be fully auxotrophic or partially auxotrophic (i.e., synthetic sickness or lethality) with respect to one or more types of fatty acid. The cells are cultured with supplementation of the fatty acid(s) so as to increase the cell number, then allowing the cells to accumulate oil (e.g., to at least 40% by dry cell weight).

Alternatively, the cells comprise a regulatable fatty acid synthesis gene that can be switched in activity based on environmental conditions and the environmental conditions during a first, cell division, phase favor production of the fatty acid and the environmental conditions during a second, oil accumulation, phase disfavor production of the fatty acid.

As a result of applying either of these supplementation or regulation methods, a cell oil may be obtained from the cell that has low amounts of one or more fatty acids essential for optimal cell propagation. Specific examples of oils that can be obtained include those low in stearic, linoleic and/or linolenic acids. Optionally, the cells are oleaginous plastidic microbes such as those of the division Chlorophyta.

Accordingly, in some embodiments, provided are methods for producing an oil or fat. The method comprises cultivating a recombinant oleaginous cell in a growth phase under a first set of conditions that is permissive to cell division so as to increase the number of cells due to the presence of a fatty acid, cultivating the cell in an oil production phase under a second set of conditions that is restrictive to cell division but permissive to production of an oil that is enriched in C8 and/or C10 fatty acids. The cell can be cultivated heterotrophically. In some embodiments, the cell can be a microalgal cell and may produce at least 40%, 50%, 60%, 70%, 80%, or 90% lipid by dry cell weight.

9. Oils with Non-Naturally Occurring Fatty Acid Profiles

Oils disclosed herein can be prepared from the microbial cell biomass by using extraction methods well-known in the art. The microbial biomass may be concentrated from the fermentation broth, and optionally dried prior to cell lysis. Alternatively, cells can be lysed without separation from some or all of the fermentation broth when the fermentation is complete. Any suitable extraction methods can be used. For example, the dried biomass can be mechanically extracted to release a crude microbial oil, e.g., using a screw press. See, e.g., PCT Application Publication WO2010120939. Other suitable methods include organic solvent extraction (see, e.g., Frenz et al. 1989, *Enzyme Microb. Technol.* 11:717); or supercritical $CO_2$ extraction (see, e.g., Mendes et al. 2003, *Inorganica Chimica Acta* 356:328-334). Optionally, the crude oil can be refined using standard edible oil refining steps, including degumming, bleaching, and deodorization.

Oils disclosed herein are distinct from other naturally occurring oils that are high in C8:0 and C10:0 medium-chain fatty acids, such as palm oil, palm kernel oil, and coconut oil. For example, levels of contaminants such as carotenoids are far higher in palm oil and palm kernel oil than in the oils described herein. Palm and palm kernel oils in particular contain alpha and beta carotenes and lycopene in much higher amounts than are in the oils described herein. In addition, over 20 different carotenoids are found in palm and palm kernel oil, whereas the oils described herein contain very few carotenoids species and very low levels. In addition, the levels of vitamin E compounds such as tocotrienols are far higher in palm, palm kernel, and coconut oil than in the oils described herein.

Generally, wild-type *Prototheca* strains have very little or no fatty acids with chain lengths of C8-C14. For example, *Prototheca moriformis* (UTEX 1435), *Prototheca krugani* (UTEX 329), *Prototheca stagnora* (UTEX 1442) and *Prototheca zopfii* (UTEX 1438) produce no (or undetectable amounts of) C8 fatty acids, between 0-0.01% C10 fatty acids, between 0.03-2.1% C12 fatty acids, and between 1.0-2.1% C14 fatty acids.

In some cases, the oleaginous cells (e.g., *Prototheca* strains) containing a transgene encoding a variant KASIVa, optionally co-expressing an exogenous lipid biosynthesis enzyme, e.g., a C10-preferring fatty acyl-ACP thioesterase, has a fatty acid profile characterized by at least about 40%, 45%, 50%, 55%, 60%, 65%, 70%, 75%, 80%, 85%, 90%, 95%, 97%, or more, C10 fatty acids. In other cases, the *Prototheca* strains containing a transgene encoding a variant KASIVa, optionally co-expressing an exogenous lipid biosynthesis enzyme, e.g., a C10-preferring fatty acyl-ACP thioesterase, has activity towards fatty acyl-ACP substrates of chain length C10 and produces fatty acids of the chain length C10.

In some instances, keeping the transgenic *Prototheca* strains under constant and high selective pressure to retain exogenous genes is advantageous due to the increase in the desired fatty acid of a specific chain length. High levels of exogenous gene retention can also be achieved by inserting exogenous genes into the nuclear chromosomes of the cells using homologous recombination vectors and methods disclosed herein. Recombinant cells containing exogenous genes integrated into nuclear chromosomes are also contemplated.

In some embodiments, oleaginous cells expressing one or more of the polynucleotides described herein can produce an oil with at least 50%, 55%, 60%, 65%, 70%, 75%, 80%, 85%, 90%, or more, C10:0 fatty acids. In some embodiments, oleaginous cells expressing one or more of the polynucleotides described herein can produce an oil with at least 70%, 71%, 72%, 73%, 74%, 75%, 76%, 77%, 78%, 79%, 80%, 81%, 82%, 83%, 84%, 85%, 86%, 87%, 88%, 89%, 90%, or more, C10:0 fatty acids.

In some embodiments, a recombinant cell comprises nucleic acids operable to express an exogenous gene encoding a variant KASIVa that catalyzes the elongation of medium-chain fatty acids from the ACP with a preference for C8-acyl ACP substrates, optionally co-expressing an exogenous lipid biosynthesis enzyme, e.g., a C10-preferring fatty acyl-ACP thioesterase.

In some embodiments, the oil produced has a fatty acid profile that is elevated in C10 fatty acids and reduced in C16:0, C18:0, and C18:1 fatty acids as a result of the expression of the recombinant nucleic acids, preferably as compared to a control cell not expressing said recombinant nucleic acids. In some embodiments, the increase in C10:0 fatty acids is greater than 5%, 10%, 20%, 30%, 40%, 50%, 80%, 100%, 200%, or more, in comparison to an untransformed microalga or a microalga transformed with a wild-type KASIVa. Preferably, the untransformed microalga or the microalga transformed with a wild-type KASIVa is an otherwise identical microalga, e.g. of the same species and preferably the same genetic background. In some embodiments, the increase in C10 fatty acids is at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type KASIVa. Preferably, the oil produced by the recombinant cell as defined herein comprises at least about 50%, 55%, 60%, 65%, 70%, 75%, 80%, 85%, 90%, or more, C10:0 fatty acids. The produced oil may further comprise at least one of tridecanoin, MLCT, ergosterol and brassicastol, preferably in an amount as defined herein. Preferably, the produced oil may further comprise at least one of ergosterol and brassicasterol. A preferred MLCT may be selected from the group consisting of CaCaLa triglyceride, CaOCa triglyceride, CaCaP triglyceride and LaLaCa triglyceride, preferably in an amount as described herein.

In some embodiments, the oil produced has a fatty acid profile that is elevated in C10 fatty acids and reduced in C16:0, C18:0, and C18:1 fatty acids as a result of the expression of the KASIVa variant as defined herein, i.e. comprising a glycine at a position corresponding to position 146 of SEQ ID NO: 4, preferably as compared to a control cell not expressing said KASIVa variant. In some embodiments, the increase in C10:0 fatty acids is greater than 5%, 10%, 20%, 30%, 40%, 50%, 80%, 100%, 200%, or more, in comparison to an untransformed microalga or a microalga transformed with a wild-type KASIVa. In some embodiments, the increase in C10 fatty acids is at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type KASIVa. Preferably, the oil produced by the recombinant cell as defined herein comprises at least about 50%, 55%, 60%, 65%, 70%, 75%, 80%, 85%, 90%, or more, C10:0 fatty acids. Preferably, the oil produced by the recombinant cell as defined herein comprises at least about 50%, 55%, 60%, 65%, 70%, 75%, 80%, 85%, 90%, or more, C10:0 fatty acids. The produced oil may further comprise at least one of tridecanoin, MLCT, ergosterol and brassicastol, preferably in an amount as defined herein. Preferably, the produced oil may further comprise at least one of ergosterol and brassicasterol. A preferred MLCT may be selected from the group consisting of CaCaLa triglyceride, CaOCa triglyceride, CaCaP triglyceride and LaLaCa triglyceride, preferably in an amount as described herein.

In some embodiments, the oil produced has a fatty acid profile that is elevated in C10 fatty acids and reduced in C16:0, C18:0, and C18:1 fatty acids as a result of the expression of the KASIVa variant as defined herein, i.e. comprising an asparagine at a position corresponding to position 146 of SEQ ID NO: 4, preferably as compared to a control cell not expressing said KASIVa variant. In some embodiments, the increase in C10:0 fatty acids is greater than 5%, 10%, 20%, 30%, 40%, 50%, 80%, 100%, 200%, or more, in comparison to an untransformed microalga or a microalga transformed with a wild-type KASIVa. In some embodiments, the increase in C10 fatty acids is at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type KASIVa. Preferably, the oil produced by the recombinant cell as defined herein comprises at least about 50%, 55%, 60%, 65%, 70%, 75%, 80%, 85%, 90%, or more, C10:0 fatty acids. Preferably, the oil produced by the recombinant cell as defined herein comprises at least about 50%, 55%, 60%, 65%, 70%, 75%, 80%, 85%, 90%, or more, C10:0 fatty acids. The produced oil may further comprise at least one of tridecanion, MLCT, ergosterol and brassicastol, preferably in an amount as defined herein. Preferably, the produced oil may further comprise at least one of ergosterol and brassicasterol. A preferred MLCT may be selected from the group consisting of CaCaLa triglyceride, CaOCa triglyceride, CaCaP triglyceride and LaLaCa triglyceride, preferably in an amount as described herein.

In some embodiments, the oil produced has a fatty acid profile that is elevated in C10 fatty acids and reduced in C16:0, C18:0, and C18:1 fatty acids as a result of the expression of the KASIVa variant as defined herein, i.e. comprising a serine at a position corresponding to position 146 of SEQ ID NO: 4, preferably as compared to a control cell not expressing said KASIVa variant. In some embodiments, the increase in C10:0 fatty acids is greater than 5%, 10%, 20%, 30%, 40%, 50%, 80%, 100%, 200%, or more, in comparison to an untransformed microalga or a microalga transformed with a wild-type KASIVa. In some embodiments, the increase in C10 fatty acids is at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type KASIVa. Preferably, the oil produced by the recombinant cell as defined herein comprises at least about 50%, 55%, 60%, 65%, 70%, 75%, 80%, 85%, 90%, or more, C10:0 fatty acids. Preferably, the oil produced by the recombinant cell as defined herein comprises at least about 50%, 55%, 60%, 65%, 70%, 75%, 80%, 85%, 90%, or more, C10:0 fatty acids. The produced oil may further comprise at least one of tridecanoin, MLCT, ergosterol and brassicastol, preferably in an amount as defined herein. Preferably, the produced oil may further comprise at least one of ergosterol and brassicasterol. A preferred MLCT may be selected from the group consisting of CaCaLa triglyceride, CaOCa triglyceride, CaCaP triglyceride and LaLaCa triglyceride, preferably in an amount as described herein.

Microalgal oil can also include other constituents produced by the microalgae, or incorporated into the microalgal oil from the culture medium. These other constituents can be present in varying amounts depending on the culture conditions used to culture the microalgae, the species of microalgae, the extraction method used to recover microalgal oil from the biomass and other factors that may affect microalgal oil composition. Non-limiting examples of such constituents include carotenoids, present from 0.1-0.4 micrograms/ml, chlorophyll present from 0-0.02 milligrams/kilogram of oil, gamma tocopherol present from 0.4-0.6 milligrams/100 grams of oil, and total tocotrienols present from 0.2-0.5 milligrams/gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-cryptoxanthin), and various organic or inorganic compounds. Additionally, microalgal oils contain long-chain polyunsaturated fatty acids, particularly eicosapentaenoic acid (EPA).

In some cases, the oil extracted from *Prototheca* species comprises no more than 0.02 mg/kg chlorophyll. In some cases, the oil extracted from *Prototheca* species comprises no more than 0.4 mcg/ml total carotenoids. In some cases the *Prototheca* oil comprises between 0.40-0.60 milligrams of gamma tocopherol per 100 grams of oil. In other cases, the *Prototheca* oil comprises between 0.2-0.5 milligrams of total tocotrienols per gram of oil.

Oils produced from host cells expressing a variant KASIVa, optionally co-expressing an exogenous lipid biosynthesis enzyme, e.g., a C10-preferring fatty acyl-ACP thioesterase, will have an isotopic profile that distinguishes it, e.g., from blended oils from other sources. The stable carbon isotope value $\delta 13C$ is an expression of the ratio of 13C/12C relative to a standard (e.g. PDB, carbonite of fossil skeleton of Belemnite americana from Peedee formation of South Carolina). The stable carbon isotope value $\delta 13C$ (0/00) of the oils can be related to the $\delta 13C$ value of the feedstock used. In some embodiments the oils are derived from oleaginous organisms heterotrophically grown on sugar derived from a C4 plant such as corn or sugarcane. In some embodiments, the $\delta 13C$ (0/00) of the oil is from 10 to −17 0/00 or from 13 to −16 0/00.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. Microalgae of Trebouxiophyceae can be distinguished from vegetable oils based on their sterol profiles. Oil produced by *Chlorella protothecoides* has been found to contain ergosterol and brassicasterols as major sterols. Both of these sterols feature C24β stereochemistry, in contrast to the C24a stereochemistry found in the majority of common plant sterols. Additional minor sterols present in *Chlorella* are also believed to primarily have C24β stereochemistry. Thus, the oils produced by the microalgae described above can be distinguished from plant oils by the preponderance of sterols with C24β stereochemistry in the sterols present. For example, the oils produced may contain 22, 23-dihydrobrassicasterol while lacking campesterol; contain clionasterol, while lacking in β-sitosterol, and/or contain poriferasterol while lacking stigmasterol. Alternately, or in addition, the oils may contain significant amounts of Δ⁷-poriferasterol. Accordingly, in some embodiments, the oils produced according to the methods described herein lack C24-α sterols.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, β-sitosterol, and stigamsterol are common plant sterols, with β-sitosterol being a principle plant sterol. For example, β-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 was separately clarified (CL), refined and bleached (RB), or refined, bleached and deodorized (RBD) and was tested for sterol content according to the procedure described in JAOCS vol. 60, no. 8, August 1983. Results of the analysis are shown below (units in mg/100 g) in Table C:

TABLE C

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 15 (2.1%) | 19 (2.6%) | 14 (2.4%) | 15 (2.5%) |

TABLE C-continued

| | Sterol | Crude | Clarified | Refined & bleached | Refined, bleached, & deodorized |
|---|---|---|---|---|---|
| 3 | Other sterols | 287 | 302 | 283 | 284 |
| | Total sterols | 686 | 719 | 590 | 601 |

These results show three striking features. First, ergosterol was found to be the most abundant of all the sterols, accounting for about 50% or more of the total sterols. Ergosterol is a sterol commonly found in fungus and not commonly found in plants, and its presence particularly in significant amounts serves as a useful marker for non-plant oils. Secondly, the oil was found to contain brassicasterol. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments most abundant sterol is ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols β-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than 0-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

The oils provided herein have many applications. Certain foods which contain medium chain triglycerides (MCT) are known to provide an instance energy source. Because the shorter chain length of the MCT fatty acids are rapidly broken down, they are known to be rapidly absorbed into the body. Because the calories contained in MCTs are more efficiently turned into energy and used by the body, they are less likely stored as fat, potentially aiding in weight loss. In a recent study, ketogenic MCTs were shown to increase brain energy metabolism in Alzheimer's disease. See *J. Alzheimer's Disease* 64 (2018:551-561). Therefore, the MCTs in the oils provided herein may be potentially useful in providing alternative energy source, and in treating or enhancing various neurological conditions.

The oils provided herein also contain a significant amount of medium-long-chain triglycerides (MLCT). Certain MLCTs were shown to be effective in decreasing the accumulation of body fat in animals and humans. MLCTs are also shown to have health benefits in targeting specific disease and metabolic conditions. Further, MLCTs can be incorporated in the mainstream foods to substitute soybean oil or palm olein in salad dressing formulation and frying oil, respectively. See Koh et al., *International Food Research Journal* 18:355-366 (2011).

The medium-chain fatty acids derived from hydrolysis of these oils may be particularly useful in food, fuel and oleochemical applications including the production of lubricants and surfactants. For example, fatty acids derived from the cells can be esterified, cracked, reduced to an aldehyde or alcohol, aminated, sulfated, sulfonated, or subjected to other chemical process known in the art.

The following examples, which are offered to illustrate, but not to limit, the compositions and methods described herein.

EXAMPLES

The following examples are offered to illustrate, but not to limit the claimed invention.

Example 1. Production of an Oil Enriched in C10:0 Fatty Acids

A method to produce an oil enriched in fatty acids with a 10-carbon chain length (C10 fatty acids) in *P. moriformis* is to introduce a β-ketoacyl-ACP synthase (KAS) gene and a fatty acyl-ACP thioesterase (FAT) gene from an oilseed plant known to make C10 fatty acids, such as *Cuphea paucipetala*, into the algal genome. Here, we report on the ability to produce an oil with >70% C10:0 fatty acids using the transgenic *P. moriformis* strain S9109, which is derived from the non-recombinant base strain S7485 and expresses two copies of the *C. paucipetala* FATB1Δ128 (CpauFATB1Δ28, SEQ ID NO: 1) thioesterase gene variant and three copies of the wild-type *C. paucipetala* KASIVa (CpauKASIVa, SEQ ID NO: 1, 2) gene through two successive transformations. S7485 is a classically-improved derivative of the wild-type strain UTEX 1435, which was obtained from the University of Texas culture collection and classically mutagenized to increase oil yield and productivity. The classical mutagenesis did not substantively alter the fatty acid profile of the oil produced by S7485 when compared to UTEX 1435. Neither S7485 nor UTEX 1435 produces an oil with a detectable amount of C10:0 fatty acids.

The expression construct pSZ5767 (SEQ ID NO: 1) was initially transformed into strain S7485 to introduce one copy of CpauFATB1 Δ28 and one copy of CpauKASIVa into each allele of the THI4 locus through a double integration event (total of two copies of each heterologous gene in the algal genome) to generate the intermediate strain S8714. Construct pSZ5767 also contains an expression cassette for the *Saccharomyces cerevisiae* SUC2 (ScSUC2) gene, which enables the transformed cells to grow on media with sucrose as the sole carbon source. The expression construct pSZ6156 (SEQ ID NO: 2) was then transformed into strain S8714 (a clonally-purified isolate) to introduce a third copy of Cpau-KASIVa to the algal geneome at the DAOlb locus to generate the final strain S9109. In addition to the CpauKA-SIVa gene, construct pSZ6156 also contains an expression cassette for the *Arabidopsis thaliana* THIC$^{L337}$ gene variant (AtTHIC$^{L337M}$) which is used for the selection of transformed cells on medium without thiamine supplementation. Expression of the CpauFATB1Δ28 and CpauKASIVa genes in the transgenic strains is driven by the constitutive PmSAD2 promoter.

To obtain sufficient oil for fatty acid and TAG profile analyses, strain 9109 (a clonally-purified isolate) was cultured under low nitrogen conditions at pH 5 and 28° C. in 250-mL baffled flasks for 5 days with an 8% (v/v) inoculum. Each flask contained 46 mL of lipid production medium that comprised 60 g/L sucrose as the sole carbon source. After 3 days of fermentation, an additional 10 g/L of sucrose was added to each production culture. Other details pertaining to the seed train, media composition, and culture conditions are described in the Examples of PCT Patent Application WO 2018/067849.

Cells from the production cultures were recovered by centrifugation and dried by lyophilization for analysis for fatty acid profile and lipid (as glycerides) titer. Ten to forty milligrams of lyophilized biomass were resuspended in 2 mL of 5% (v/v) $H_2SO_4$ in methanol, and 200 ρt of toluene containing an appropriate amount of a suitable internal standard (C19:0) were added. The resulting mixture was sonicated briefly to disperse the biomass, and then heated at 70-75° C. for 3.5 hours with intermittent sonicating and vortex mixing. Heptane (2 mL) was added for the extraction of the fatty acid methyl esters, followed by addition of 2 mL of 10% (w/v) $K_3PO_4$ (aq) to neutralize. The mixture was agitated vigorously, and a portion of the upper layer was transferred to a vial containing $Na_2SO_4$ (anhydrous) for gas chromatography analysis using standard FAME GC/FID (fatty acid methyl ester gas chromatography flame ionization detection) methods.

Triacylglycerols were identified by LC/MS analysis using a Shimadzu Nexera ultra high performance liquid chromatography system that included a SIL-30AC autosampler, two LC-30AD pumps, and a DGU-20A5 in-line degasser, coupled to a Shimadzu LCMS 8030 triple quadrupole mass spectrometer equipped with an APCI source. Data was acquired using a Q3 scan of m/z 300-950 at a scan speed of 1363 u/sec in positive ion mode with the CID gas (argon) pressure set to 230 kPa. The APCI, desolvation line, and heat block temperatures were set to 300, 250, and 200° C., respectively, the flow rates of the nebulizing and drying gases were 3.0 L/min and 5.0 L/min, respectively, and the interface voltage was 4500 V. Oil samples were dissolved in dichloromethane-methanol (1:1) to a concentration of 5 mg/mL, and 0.4 µL of sample was injected onto an Thermo Scientific Acclaim RSLC 120 C18 (2.2 µm, 2.1×250 mm) column maintained at 15° C. in a Cole-Parmer column heater/chiller. A linear gradient from 30% dichloromethane-2-propanol (1:1)/acetonitrile to 56% dichloromethane-2-propanol (1:1)/acetonitrile over 34 minutes at 0.48 mL/min was used for chromatographic separations.

Triacylglycerol profiles were generated by HPLC with RID (Refractive Index Detector) using AOCS method Ce 5c-93, modified to include two columns. Hichrom Alltima HP C18-HL and Acclaim 120 C18 columns, both 5 µm, 4.6×250 mm, in series, were used.

As shown in Table 1, strain S9109 is capable of producing an oil with a high level of C10:0 fatty acids, which account for 72% of the total fatty acids. At the same time, 46% of the triglycerides produced are medium-chain fatty acid triglycerides (MCTs), in which all three fatty acids bound to the glycerol backbone are medium-chain fatty acids having 6 to 10 carbons (C6-C10) (Table 2). Tridecanoin (CaCaCa), which comprise 45% of the total triglycerides, is the major MCT species. In addition, 51% of the triglycerides produced are also medium and long chain fatty acid triglycerides (MLCTs), in which at least one medium chain fatty acid having 6 to 10 carbons (C6-C10) and at least one long chain fatty acid having 12 carbons or more are bound to the glycerol backbone. These results demonstrate that an oil rich in C10:0 fatty acids, MCTs, and MLCTs can be produced through the introduction of two heterologous genes from the oilseed plant *C. paucipetala* into the oleaginous microalga *P. moriformis*.

TABLE 2-continued

Non-regiospecific TAG profile of oil extracted
from dried biomass of strain S9109.*

| TAG (non-regiospecific) | % of Triglycerides |
|---|---|
| CaOLa | 3.0 |
| CaOL | 0.3 |
| CaLP | 1.6 |
| CaOM | 0.5 |
| CaOO | 0.8 |
| CaOP | 2.0 |
| Total TAGs identified: | 97.4 |

Strain S9109 was cultured in 250-mL baffled flasks under low-nitrogen conditions at pH 5 and 28° C. for 5 days.
Cy = caprylate (C8:0), Ca = caprate (C10:0), La = laurate (C12:0), M = myristate (C14:0), P = palmitate (C16:0), O = oleate (C18:1), L = linoleate (C18:2), and Ln = α-linolenate (C18:3 α).

Example 2. Improved Variant of *Cuphea paucipetala* KASIVa Enzyme

To minimize the number of copies of the CpauKASIVa gene needed to produce an oil with >70% C10:0 fatty acids in *P. moriformis*, the heterologous KAS enzyme was subjected to site-directed mutagenesis using known techniques familiar to those skilled in the art to increase its activity. Here, we report on the improvement in C10 activity achieved by replacing the native threonine residue at position 146 of the *C. paucipetala* KASIVa (CpauKASIVa) with a serine residue. Results obtained from expression of the wild-type CpauKASIVa (SEQ NO ID: 3) or the improved CpauKASIVa$^{T146S}$ variant with the Thr146 to Ser mutation (SEQ NO ID: 4) in conjunction with the *C. paucipetala* FATB1 Δ28 thioesterase variant (CpauFATB1Δ28, SEQ NO ID: 5) for C10 production in *P. moriformis* are also described.

An expression construct that targets integration of the CpauKASIVa$^{T146S}$ gene variant (pSZ6871, SEQ ID NO: 6)

TABLE 1

Fatty acid profile of oil extracted from dried biomass of strain S9109.*

Fatty Acid Profile (%)

| Sample | C8:0 | C10:0 | C11:0 | C12:0 | C14:0 | C14:1 cis-9 | C16:0 | C16:1 cis-9 | C17:0 | C18:0 | C18:1 | C18:2 | C18:3 α | C20:0 | C20:1 | C21:0 | C22:0 |
|---|---|---|---|---|---|---|---|---|---|---|---|---|---|---|---|---|---|
| S9109 dried biomass | 0.5 | 72.0 | 0.1 | 6.8 | 2.6 | 0.0 | 5.4 | 0.1 | 0.0 | 0.5 | 9.0 | 2.5 | 0.3 | 0.1 | 0.0 | 0.1 | 0.0 |

Strain S9109 was cultured in 250-mL baffled flasks under low-nitrogen conditions at pH 5 and 28° C. for 5 days. Results are presented as average values from replicate analyses.

TABLE 2

Non-regiospecific TAG profile of oil extracted
from dried biomass of strain S9109.*

| TAG (non-regiospecific) | % of Triglycerides |
|---|---|
| CyCaCa | 1.5 |
| CaCaCa | 44.8 |
| CaLnCa | 0.3 |
| CaCaLa | 12.6 |
| CaLCa | 3.4 |
| CaCaM + LaLaCa | 5.5 |
| CaLLa | 0.4 |
| CaOCa | 12.5 |
| CaCaP | 8.3 | or the wild-type CpauKASIVa gene (pSZ6757, SEQ ID NO: 7) to the THI4 locus in *P. moriformis* was transformed into the host strain S9189, which already harbors two copies of the CpauFATB1Δ28 thioesterase gene, one at each allele of its DAO1b locus. Constructs pSZ6757 and pSZ6871 also contain an expression cassette for the *S. cerevisiae* SUC2 (ScSUC2) gene, which enables growth of the resulting transformants on medium containing sucrose as the sole carbon source. Strain S9189 is a clonally-purified transformant that is stable in phenotype and was obtained through transformation of the expression construct pSZ6712 (SEQ ID NO: 8) into the base strain S9112, which itself does not produce oil with C10:0 fatty acids. In addition to the CpauFATB1Δ28 gene, construct pSZ6712 also contains an expression cassette for the *Arabidopsis thaliana* THIC$^{L337M}$ gene variant, which is used as a selectable marker for the growth of transformants on medium without thiamine supplementation. The expression of CpauKASIVa, CpauKASIVa$^{T146S}$ and CpauFATB1Δ28 in the transgenic strains is driven by the pH 7-inducible PmAMT3 promoter.

Clonally-purified transformants derived from strain S9189 and expressing the CpauKASIVa$^{T146S}$ gene variant (pSZ6871) or wild-type CpauKASIVa gene (pSZ6757) were evaluated in 3-day lipid production cultures at pH 7 (as detailed in the Examples of PCT Patent Application WO 2018/067849) to determine their fatty acid profiles. The parental strain S9189 and the base strain S9112 were also assessed under the same conditions as controls. As presented in Table 3, single and double integrants of the wild-type CpauKASIVa gene (pSZ6757) can produce oils with average C10:0 levels of 56% and 76%, respectively. In comparison, single and double integrants of the CpauKASIVa$^{T146S}$ gene variant (pSZ6871) yielded oils with higher C10:0 levels, which reached 59% and 79%, respectively. These results also indicate that the expression of a second copy of the KAS transgene can significantly boost the C10:0 level of the oils. In contrast, the parental strain S9189, which harbors two copies of the CpauFATB1Δ28 thioesterase gene but does not express either one of the KAS transgenes, produced oils with only approximately 21% C10:0. No C10:0 fatty acids were detected in the oil accumulated by the base strain S9112.

the sole carbon source. Similar to strain S9189 in Example 2, strain S9316 is a clonally-purified transformant that is stable in phenotype and was obtained through transformation of the expression construct pSZ6769 (SEQ NO ID: 15) into the base strain S9281, which itself does not produce oil with C10:0 fatty acids. In addition to the CpauFATB1Δ28 gene, construct pSZ6769 also contains an expression cassette for the A. thaliana THIC$^{L337M}$ gene variant, which is used as a selectable marker for the growth of transformants on medium without thiamine supplementation. The expression of the CpauKASIVa$^{L146X}$ variants and CpauFATB1Δ28 in the transgenic strains is driven by the constitutive PmSAD2-1 promoter.

Clonally-purified transformants derived from strain S9316 and expressing a single copy of one of the CpauKASIVa$^{L146X}$ variants (pSZ6756, pSZ6921, or pSZ7123-pSZ7140) were evaluated in 5-day lipid production cultures at pH 7 (as detailed in the Examples of PCT Patent Application WO2018/067849) to determine their fatty acid profiles. The parental strain S9316 and a base strain, 57485, which itself does not produce oil with C10:0 fatty acids, were also assessed under the same conditions as controls. The average C10:0 fatty acid levels of the oils produced by these transformants and strains are presented in Table 4. While the parental strain S9316 can produce an oil with 19% C10:0, the addition of one copy of the wild-type CpauKASIVa (pSZ6756) enabled the resulting transfor-

TABLE 3

| Strain/Transformants | CpauKASIVa | Integration | n | C8:0 (%) | C10:0 (%) | C12:0 (%) | C14:0 (%) |
|---|---|---|---|---|---|---|---|
| | | | | | Average | | |
| S9189-pSZ6871 | T146S | Single | 8 | 0.6 | 58.3 | 6.1 | 4.2 |
| S9189-pSZ6871 | T146S | Double | 12 | 0.9 | 78.9 | 5.6 | 2.3 |
| S9189-pSZ6757 | Wild-type | Single | 6 | 0.6 | 54.9 | 5.8 | 4.6 |
| S9189-pSZ6757 | Wild-type | Double | 13 | 0.9 | 75.9 | 5.9 | 2.7 |
| S9189 (parent) | — | — | 2 | 0.2 | 21.2 | 2.8 | 4.2 |
| S9112 (base strain) | — | — | 2 | 0.1 | 0.0 | 0.1 | 2.3 |

The parental strain S9189 was transformed with construct pSZ6871 (CpauKASIVa $^{T146S}$) or construct pSZ6757 (wild-type CpauKASIVa). Clonally-purified transformants were tested in three-day lipid production cultures at pH 7 under low nitrogen conditions. Day-3 fatty acid profiles are shown for both single and double integrants of the heterologous KAS genes.
n = total of replicates or transformants tested.

Example 3. Saturation Mutagenesis at Amino Acid Residue 146 of the *Cuphea paucipetala* KASIVa Enzyme Example 2 demonstrated that a Thr to Ser mutation at amino acid residue 146 of the CpauKASIVa enzyme (SEQ NO ID: 4) can increase the C10:0 fatty acid level of the oil produced by *P. moriformis* when co-expressed with a thioesterase (CpauFATB1Δ28, SEQ NO ID: 5) enzyme. In this example, results from saturation mutagenesis at position 146 of CpauKASIVa indicating the importance of that amino acid position in producing oils with elevated C10:0 fatty acids are described.

An expression construct that targets integration of the wild-type CpauKASIVa gene (pSZ6756, SEQ NO ID: 13), the CpauKASIVa$^{T146S}$ gene variant (pSZ6921, SEQ NO ID: 14), or the remaining eighteen CpauKASIVa$^{T146X}$ gene variants (pSZ7123-pSZ7140, SEQ NO ID: 14) to the THI4 locus in *P. moriformis* was transformed into the host strain S9316, which harbors two copies of the CpauFATB1Δ28 thioesterase gene, one at each allele of its DAO 1 locus. These constructs also contain an expression cassette for the *S. cerevisiae* SUC2 (ScSUC2) gene, which enables growth of the resulting transformants on medium containing sucrose as mants to reach 44% C10:0. Expression of the T146S variant (pSZ6921) instead of the wild-type CpauKASIVa further elevated the C10:0 level to 52%. This was the highest C10:0 level observed across all twenty amino acid substitutions. Replacement of Thr146 with one of the other eighteen amino acids yielded C10:0 levels that ranged from 25% to 50%. Although the C10:0 levels (48-50%) achieved with the T146G and T146N variants (pSZ7123 and pSZ7130) were not as high as with the T146S variant, they still exceeded the C10:0 level achieved with the wild-type enzyme. The sensitivity of the C10:0 level to the choice of amino acid at position 146 of the CpauKASIVa enzyme demonstrates the importance of this amino acid position on the biosynthesis of triglycerides rich in C10:0 fatty acids.

TABLE 4

| Strain/Transformants | CpauKASIVa | n | C8:0 (%) | C10:0 (%) | C12:0 (%) | C14:0 (%) |
|---|---|---|---|---|---|---|
| | | | | Average | | |
| S9316-pSZ7123 | T146G | 8 | 0.3 | 49.5 | 6.2 | 4.7 |
| S9316-pSZ7124 | T146E | 8 | 0.2 | 33.4 | 4.5 | 5.2 |
| S9316-pSZ7125 | T146D | 7 | 0.2 | 31.9 | 4.3 | 5.1 |

TABLE 4-continued

| Strain/ Transformants | CpauKASIVa | n | Average | | | |
|---|---|---|---|---|---|---|
| | | | C8:0 (%) | C10:0 (%) | C12:0 (%) | C14:0 (%) |
| S9316-pSZ7126 | T146V | 8 | 0.2 | 27.6 | 3.7 | 4.8 |
| S9316-pSZ7127 | T146A | 7 | 0.3 | 39.3 | 5.1 | 5.1 |
| S9316-pSZ7128 | T146R | 5 | 0.3 | 42.1 | 5.5 | 5.2 |
| S9316-pSZ7129 | T146K | 7 | 0.3 | 38.2 | 5.0 | 5.2 |
| S9316-pSZ7130 | T146N | 8 | 0.3 | 47.9 | 6.0 | 4.8 |
| S9316-pSZ7131 | T146M | 8 | 0.2 | 32.5 | 4.4 | 5.0 |
| S9316-pSZ7132 | T146I | 8 | 0.2 | 24.9 | 3.4 | 4.6 |
| S9316-pSZ7133 | T146W | 8 | 0.2 | 26.2 | 3.6 | 4.7 |
| S9316-pSZ7134 | T146C | 7 | 0.3 | 40.1 | 5.3 | 5.2 |
| S9316-pSZ7135 | T146Y | 8 | 0.2 | 31.7 | 4.3 | 5.1 |
| S9316-pSZ7136 | T146L | 7 | 0.2 | 32.9 | 4.4 | 5.1 |
| S9316-pSZ7137 | T146F | 8 | 0.2 | 30.6 | 4.1 | 5.0 |
| S9316-pSZ7138 | T146Q | 8 | 0.3 | 44.3 | 5.6 | 5.1 |
| S9316-pSZ7139 | T146H | 8 | 0.3 | 39.0 | 5.1 | 5.0 |
| S9316-pSZ7140 | T146P | 8 | 0.2 | 25.7 | 3.4 | 4.5 |
| S9316-pSZ6756 | WT | 7 | 0.3 | 44.3 | 5.7 | 5.0 |
| S9316-pSZ6921 | T146S | 7 | 0.4 | 51.5 | 6.3 | 4.6 |

TABLE 4-continued

| Strain/ Transformants | CpauKASIVa | n | Average | | | |
|---|---|---|---|---|---|---|
| | | | C8:0 (%) | C10:0 (%) | C12:0 (%) | C14:0 (%) |
| S9316 (parent) | — | 3 | 0.1 | 19.1 | 2.7 | 3.9 |
| S7485 (base strain) | — | 3 | 0.0 | 0.0 | 0.1 | 2.1 |

The parental strain S9316 was transformed with construct pSZ6756, pSZ6921, or pSZ7123-pSZ7140. Each of these constructs expresses either the wild-type CpauKASIVa or one of the enzyme variants containing an amino acid substitution at position 146. Clonally-purified transformants were tested in five-day lipid production cultures at pH 7 under low nitrogen conditions. The caprylic, capric, lauric, and myristic fatty acid levels of the oils produced by single integrants of the heterologous KAS genes are shown. The variants highlighted and in bold represent the amino acid substitutions that conferred higher C10:0 levels.
n = total of replicates or transformants tested.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING
SEQ ID NO: 1 - Nucleic acid sequence of construct pSZ5767 for the expression of the Cuphea paucipetala FATB1Δ28 (CpauFATB1Δ28) thioeseterase gene variant and the wild-type C. paucipetala KASIVa (CpauKASIVa) gene in P. moriformis at the THI4 locus.
Nonspecific or vector sequences are in plain uppercase.
Relevant restriction sites (5' → 3': PmeI, KpnI, XbaI, AvrII, NdeI, EcoRV, HindIII, SpeI, SacI, and PmeI) are in bold, underlined lowercase. PmeI sites delimit the 5' and 3' ends of the transforming DNA. The 5' and 3' homology targeting arms for integration at the THI4 locus are in bold lowercase. Proceeding in the 5' to 3' direction, the CrTUB2 promoter is in boxed, lowercase italics. The ScSUC2 selection marker is bold, lowercase italics. The PmPGH 3'-UTR is in plain, underlined lowercase. The buffer DNA sequence that follows is in plain lowercase. The PmSAD2-2p promoter is in boxed, uppercase italics. The PmSAD1tp transit peptide is in bold, underlined, uppercase italics, the CpauKASIVa gene (with codon bias for improved expression in P. moriformis) is in bold, uppercase italics, and the HA epitope tag is double-underlined and in bold, uppercase italics. The CvNR (from Chlorella vulgaris) 3'-UTR is in plain, underlined uppercase. The PmSAD2-1v3p promoter is in boxed, uppercase italics. The modified (with codon bias for improved expression in P. moriformis) CpSAD1tp is in bold, underlined, uppercase italics, the nucleic acid encoding CpauFATB1Δ28 thioesterase gene (with codon bias for improved expression in P. moriformis) is in bold, uppercase italics, and the 3xFLAG tag is double-underlined and in bold, uppercase italics. The PmSAD2-1 3'-UTR is in plain, underlined uppercase.
AGCGGAAGAGCGCCCAATgtttaaacccctcaactgcgacgctgggaaccttctccgggca ggcgatgtgcgtgggtttgcctccttggcacggctctacaccgtcgagtacgccatgaggc ggtgatggctgtgtcggttgccacttcgtccagagacggcaagtcgtccatcctctgcgtg tgtggcgcgacgctgcagcagtccctctgcagcagatgagcgtgactttggccatttcacg cactcgagtgtacacaatccattttttcttaaagcaaatgactgctgattgaccagatactg taacgctgatttcgctccagatcgcacagatagcgaccatgttgctgcgtctgaaaatctg gattccgaattcgaccctggcgctccatccatgcaacagatggcgacacttgttacaattc ctgtcacccatcggcatggagcaggtccacttagattcccgatcacccacgcacatctcgc taatagtcattcgttcgtgtcttcgatcaatctcaagtgagtgtgcatggatcttggttga cgatgcggtatgggtttgcgccgctggctgcagggtctgcccaaggcaagctaacccagct cctctccccgacaatactctcgcaggcaaagccggtcacttgccttccagattgccaataa -continued actcaattatggcctctgtcatgccatccatgggtctgatgaatggtcacgctcgtgtcct gaccgttccccagcctctggcgtccctgccccgcccaccagcccacgccgcgcggcagtc gctgccaaggctgtctcggag<u>ggtacc</u>⎡*ctttcttgcgctatgacacttccagcaaaaggtag*⎤

⎡*ggcgggctgcgagacggcttcccggcgctgcatgcaacaccgatgatgcttcgacccccg*⎤

⎡*aagctccttcgggggctgcatgggcgctccgatgccgctccagggcgagcgctgtttaaata*⎤

⎡*gccaggcccccgattgcaaagacattatagcgagctaccaaagccatattcaaacacctag*⎤

⎡*atcactaccacttctacacaggccactcgagcttgtgatcgcactccgctaaggggggcgcc*⎤

⎡*tcttcctcttcgtttcagtcacaacccgcaaac*⎤tctagaATATCA*atgctgctgcaggcct*

*tcctgttcctgctggccggcttcgccgccaagatcagcgcctccatgacgaacgagacgtc*

*cgaccgcccctggtgcacttcacccccaacaagggctggatgaacgaccccaacggcctg*

*tggtacgacgagaaggacgccaagtggcacctgtacttccagtacaacccgaacgacaccg*

*tctgggggacgcccttgttctggggccacgccacgtccgacgacctgaccaactgggagga*

*ccagcccatcgccatcgccccgaagcgcaacgactccggcgccttctccggctccatggtg*

*gtggactacaacaacacctccggcttcttcaacgacaccatcgaccccgcgccagcgctgcg*

*tggccatctggacctacaacaccccggagtccgaggacgcagtacatctcctacagcctgga*

*cggcggctacaccttcaccgagtaccagaagaacccccgtgctggccgccaactccacccag*

*ttccgcgacccgaaggtcttctggtacgagccctcccagaagtggatcatgaccgcggcca*

*agtcccaggactacaagatcgagatctactcctccgacgacctgaagtcctggaagctgga*

*gtccgcgttcgccaacgagggcttcctcggctaccagtacgagtgccccggcctgatcgag*

*gtccccaccgagcaggaccccagcaagtcctactgggtgatgttcatctccatcaacccg*

*gcgccccggccggcggctccttcaaccagtacttcgtcggcagcttcaacggcacccactt*

*cgaggccttcgacaaccagtcccgcgtggtggacttcggcaaggactactacgccctgcag*

*accttcttcaacaccgacccgacctacgggagcgccctgggcatcgcgtgggcctccaact*

*gggagtactccgccttcgtgcccaccaaccccctggcgctcctccatgtccctcgtgcgcaa*

*gttctccctcaacaccgagtaccaggccaacccggagacggagctgatcaacctgaaggcc*

*gagccgatcctgaacatcagcaacgccggcccctggagccggttcgccaccaacaccacgt*

*tgacgaaggccaacagctacaacgtcgacctgtccaacagcaccggcaccctggagttcga*

*gctggtgtacgccgtcaacaccacccagacgatctccaagtccgtgttcgcggacctctcc*

*ctctggttcaagggcctggaggaccccgaggagtacctccgcatgggcttcgaggtgtccg*

*cgtcctccttcttcctggaccgcgggaacagcaaggtgaagttcgtgaaggagaaccccta*

*cttcaccaaccgcatgagcgtgaacaaccagcccttcaagagcgagaacgacctgtcctac*

*tacaaggtgtacggcttgctggaccagaacatcctggagctgtacttcaacgacggcgacg*

*tcgtgtccaccaacacctacttcatgaccaccgggaacgccctgggctccgtgaacatgac*

*gacgggggtggacaacctgttctacatcgacaagttccaggtgcgcgaggtcaagtga*CAA

TTGacgcccgcgcggcgcacctgacctgttctctcgagggcgcctgttctgccttgcgaaa caagcccctggagcatgcgtgcatgatcgtctctggcgccccgccgcgcggtttgtcgccc tcgcgggcgccgcggccgcgggggcgcattgaaattgttgcaaaccccacctgacagattg agggcccaggcaggaaggcgttgagatggaggtacaggagtcaagtaactgaaagtttta -continued tgataactaacaacaaagggtcgtttctggccagcgaatgacaagaacaagattccacatt tccgtgtagaggcttgccatcgaatgtgagcgggcgggccgcggacccgacaaaaccctta cgacgtggtaagaaaaacgtggcgggcactgtccctgtagcctgaagaccagcaggagacg atcggaagcatcacagcacaGGATCCcgcgtctcgaacagagcgcgcagaggaacgctgaa ggtctcgcctctgtcgcacctcagcgcggcatacaccacaataaccacctgacgaatgcgc ttggttcttcgtccattagcgaagcgtccggttcacacacgtgccacgttggcgaggtggc aggtgacaatgatcggtggagctgatggtcgaaacgttcacagcctaggGAATTC┌CTGAAG┐

┌AATGGGAGGCAGGTGTTGTTGATTATGAGTGTGTAAAAGAAAGGGGTAGAGAGCCGTCCTC┐

┌AGATCCGACTACTATGCAGGTAGCCGCTCGCCCATGCCCGCCTGGCTGAATATTGATGCAT┐

┌GCCCATCAAGGCAGGCAGGCATTTCTGTGCACGCACCAAGCCCACAATCTTCCACAACACA┐

┌CAGCATGTACCAACGCACGCGTAAAAGTTGGGGTGCTGCCAGTGCGTCATGCCAGGCATGA┐

┌TGTGCTCCTGCACATCCGCCATGATCTCCTCCATCGTCTCGGGTGTTTCCGGCGCCTGGTC┐

┌CGGGAGCCGTTCCGCCAGATACCCAGACGCCACCTCCGACCTCACGGGGTACTTTTCGAGC┐

┌GTCTGCCGGTAGTCGACGATCGCGTCCACCATGGAGTAGCCGAGGCGCCGGAACTGGCGTG┐

┌ACGGAGGGAGGAGAGGGAGGAGAGAGAGGGGGGGGGGGGGGGGGGGATGATTACACGCCAGT┐

┌CTCACAACGCATGCAAGACCCGTTTGATTATGAGTACAATCATGCACTACTAGATGGATGA┐

┌GCGCCAGGCATAAGGCACACCGACGTTGATGGCATGAGCAACTCCCGCATCATATTTCCTA┐

┌TTGTCCTCACGCCAAGCCGGTCACCATCCGCATGCTCATATTACAGCGCACGCACCGCTTC┐

┌GTGATCCACCGGGTGAACGTAGTCCTCGACGGAAACATCTGGCTCGGGCCTCGTGCTGGCA┐

┌CTCCCTCCCATGCCGACAACCTTTCTGCTGTCACCACGACCCACGATGCAACGCGACACGA┐

┌CCCGGTGGGACTGATCGGTTCACTGCACCTGCATGCAATTGTCACAAGCGCATACTCCAAT┐

┌CGTATCCGTTTGATTTCTGTGAAAACTCGCTCGACCGCCCGCGTCCCGCAGGCAGCGATGA┐

┌CGTGTGCGTGACCTGGGTGTTTCGTCGAAAGGCCAGCAACCCCAAATCGCAGGCGATCCGG┐

┌AGATTGGGATCTGATCCGAGCTTGGACCAGATCCCCCACGATGCGGCACGGGAACTGCATC┐

┌GACTCGGCGCGGAACCCAGCTTTCGTAAATGCCAGATTGGTGTCCGATACCTTGATTTGCC┐

┌ATCAGCGAAACAAGACTTCAGCAGCGAGCGTATTTGGCGGGCGTGCTACCAGGGTTGCATA┐

┌CATTGCCCATTTCTGTCTGGACCGCTTTACCGGCGCAGAGGGTGAGTTGATGGGGTTGGCA┐

┌GGCATCGAAACGCGCGTGCATGGTGTGTGTGTCTGTTTTCGGCTGCACAATTTCAATAGTC┐

┌GGATGGGCGACGGTAGAATTGGGTGTTGCGCTCGCGTGCATGCCTCGCCCCGTCGGGTGTC┐

┌ATGACCGGGACTGGAATCCCCCCTCGCGACCCTCCTGCTAACGCTCCCGACTCTCCCGCCC┐

GCGCGCAGGATAGACTCTAGTTCAACCAATCGACA*catAT**GGCTTCCGCGGCATTCACCAT*

*GTCGGCGTGCCCCGCGATGACTGGCAGGGCCCCTGGGGCACGTCGCTCCGGACGGCCAGTC*

*GCCACCCGCCTGAGGGGCTCCACCTTCCAGTGCCTGGTGAACTCCCACATCGACCCCTGCA*

ACCAGAACGTGTCCTCGCCTCCCTGTCCTTCCTGGGCGACAACGGCTTCGGCTCCAACCCC

CTTCCGCTCCAACCGCGGCCACCGCCGCCTGGGCCGCGCCTCCCACTCCGGCGAGGCCATG

GCCGTGGCCCTGCAGCCCGCCCAGGAGGTGGCCACCAAGAAGAAGCCCGCCATCAAGCAGC

GCCGCGTGGTGGTGACCGGCATGGGCGTGGTGACCCCCCTGGGCCACGAGCCCGACGTGTT

CTACAACAACCTGCTGGACGGCGTGTCCGGCATCTCCGAGATCGAGACCTTCGACTGCACC

CAGTTCCCCACCCGCATCGCCGGCGAGATCAAGTCCTTCTCCACCGACGGCTGGGTGGCCC

CCAAGCTGTCCAAGCGCATGGACAAGTTCATGCTGTACCTGCTGACCGCCGGCAAGAAGGC

CCTGGCCGACGCCGGCATCACCGAGGACGTGATGAAGGAGCTGGACAAGCGCAAGTGCGGC

GTGCTGATCGGCTCCGGCATGGGCGGCATGAAGCTGTTCAACGACTCCATCGAGGCCCTGC

GCGTGTCCTACAAGAAGATGAACCCCTTCTGCGTGCCCTTCGCGGACCACCAACATGGGCTC

CGCCATGCTGGCCATGGACCAACTACTCCATCCCTGGGCTGGATGGGCCTCCACCGCCTGC

GCCACCTCCAACTTCTGCATCCTGAACGCCGCCAACCACATCATCCGCGGCGAGGCCGACA

TGATGCTGTGCGGCGGCTCCGACGCCGTGATCATCCCCATCGGCCTGGGCGGCTTCGTGGC

CTGCCGCGCCCTGTCCCAGCGCAACTCCGACCCCACCAAGGCCTCCCGCCCCTGGGACTCC

AACCGCGACGGCTTCGTGATGGGCGAGGGCGCCGGCGTGCTGCTGCTGGAGGAGCTGGAGC

ACGCCAAGAAGCGCGGCGCCACCATCTACGCCGAGTTCCTGGGCGGCTCCTTCACCTGCGA

CGCCTACCACATGACCGAGCCCCACCCCGACGGCGCCGGCGTGATCCTGTGCATCGAGAAG

GCCCTGGCCCAGTCCGGCGTGTCCCGCGAGGACGTGAACTACATCAACGCCCACGCCACCT

CCACCCCCGCCGGCGACATCAAGGAGTACCAGGCCCTGGCCCACTGCTTCGGCCAGAACTC

CGAGCTGCGCGTGAACTCCACCAAGTCCATGATCGGCCACCTGCTGGGCGCCGCCGGCGGC

GTGGAGGCCGTGACCGTGATCCAGGCCATCCGCACCGGCTGGATCCACCCCAACCTGAACC

TGGAGGACCCCGACGAGGCCGTGGACGCCAAGTTCCTGGTGGGCCCCAAGAAGGAGCGCCT

GAACGTGAAGGTGGGCCTGTCCAACTCCTTCGGCTTCGGCGGCCACAACTCCTCCATCCTG

TTCGCCCCCTACAACACCATG*TACCCCTACGACGTGCCCGACTACGCCTGA*atcGAGGCA

GCAGCAGCTCGGATAGTATCGACACACTCTGGACGCTGGTCGTGTGATGGACTGTTGCCGC

CACACTTGCTGCCTTGACCTGTGAATATCCCTGCCGCTTTTATCAAACAGCCTCAGTGTGT

TTGATCTTGTGTGTACGCGCTTTTGCGAGTTGCTAGCTGCTTGTGCTATTTGCGAATACCA

CCCCCAGCATCCCCTTCCCTCGTTTCATATCGCTTGCATCCCAACCGCAACTTATCTACGC

TGTCCTGCTATCCCTCAGCGCTGCTCCTGCTCCTGCTCACTGCCCCTCGCACAGCCTTGGT

TTGGGCTCCGCCTGTATTCTCCTGGTACTGCAACCTGTAAACCAGCACTGCAATGCTGATG

CACGGGAAGTAGTGGGATGGGAACACAAATGGA*aagctt*GGGAGCAGTTGTCGACCGCCCG

CGTCCCGCAGGCAGCGATGACGTGTGCGTGGCCTGGGTGTTTCGTCGAAAGGCCAGCAACC

CTAAATCGCAGGCGATCCGGAGATTGGGATCTGATCCGAGTTTGGACCAGATCCGCCCCGA

TGCGGCACGGGAACTGCATCGACTCGGCGCGGAACCCAGCTTTCGTAAATGCCAGATTGGT

GTCCGATACCTGGATTTGCCATCAGCGAAACAAGACTTCAGCAGCGAGCGTATTTGGCGGG

CGTGCTACCAGGGTTGCATACATTGCCCATTTCTGTCTGGACCGCTTTACTGGCGCAGAGG

GTGAGTTGATGGGGTTGGCAGGCATCGAAACGCGCGTGCATGGTGTGCGTGTCTGTTTTCG

GCTGCACGAATTCAATAGTCGGATGGGCGACGGTAGAATTGGGTGTGGCGCTCGCGTGCAT

GCCTCGCCCCGTCGGGTGTCATGACCGGGACTGGAATCCCCCCTCGCGACCATCTTGCTAA

CGCTCCCGACTCTCCCGACCGCGCGCAGGATAGACTCTTGTTCAACCAATCGACAactagt

AACA*ATGGCCACCGCCTCCACCTTCTCCGCCTTCAACGCCCGCTGCGGCGACCTGCGCCGC*

*TCCGCCGGCTCCGGCCCCGCCGCCCCGCCCGCCCCCTGCCCGTGCGCGCCGCCATCAACG*

*CCTCCGCCCACCCCAAGGCCAACGGCTCCGCCGTGAACCTGAAGTCCGGCTCCCTGAACAC*

*CCAGGAGGACACCTCCTCCTCCCCCCCCCCCCGCGCCTTCCTGAACCAGCTGCCCGACTGG*

*TCCATGCTGGTGGACTCCGTGGGCCTGAAGTCCGTGGTGCTGGACGGCCTGGTGTCCCGCC*

*AGATCTTCTCCATCCGCTCCTACGAGATCGGCGCCGACCGCACCGCCTCCATCGAGACCCT*

*GATGAACCACCTGCAGGAGACCTCCATCAACCACTGCAAGTCCCTGGGCCTGCTGAACGAC*

*GGCTTCGGCCGCACCCCCGGCATGTGCAAGAACGACCTGATCTGGGTGCTGACCAAGATGC*

*AGATCATGGTGAACCGCTACCCCACCTGGGGCGACACCGTGGAGATCAACACCTGGTTCTC*

*CCACTCCGGCAAGATCGGCATGGCCTCCGACTGGCTGATCACCGACTGCAACACCGGCGAG*

*ATCCTGATCCGCGCCACCTCCGTGTGGGCCATGATGAACCAGAAGACCCGCCGCTTCTCCC*

*GCCTGCCCTACGAGGTGCGCCAGGAGCTGACCCCCCACTACGTGGACTCCCCCCACGTGAT*

*CGAGGACAACGACCGCAAGCTGCACAAGTTCGACGTGAAGACCGGCGACTCCATCCGCAAG*

*GGCCTGACCCCCCGCTGGAACGACCTGGACGTGAACCAGCACGTGTCCAACGTGAAGTACA*

*TCGGCTGGATCCTGGAGTCCATGCCCATCGAGGTGCTGGAGACCCAGGAGCTGTGCTCCCT*

*GACCGTGGAGTACCGCCGCGAGTGCGGCATGGACTCCGTGCTGGAGTCCGTGACCGCCATG*

*GACCCCTCCGAGGACGAGGGCCGCTCCCAGTACAAGCACCTGCTGCGCCTGGAGGACGGCA*

*CCGACATCGTGAAGGGCCGCACCGAGTGGCGCCCCAAGAACGCCGGCACCAACGGCGCCAT*

*CTCCACCGCCAAGCCCTCCAACGGCAACTCCGTGTCC*ATGGACTACAAGGACCACGACGGC

GACTACAAGGACCACGACATCGACTACAAGGACGACGACGACAAGTGActcgagGGAGCGA

CGAGTGTGCGTGCGGGGCTGGCGGGAGTGGGACGCCCTCCTCGCTCCTCTCTGTTCTGAAC

GGAACAATCGGCCACCCCGCGCTACGCGCCACGCATCGAGCAACGAAGAAAACCCCCCGAT

GATAGGTTGCGGTGGCTGCCGGGATATAGATCCGGCCGCACATCAAAGGGCCCCTCCGCCA

GAGAAGAAGCTCCTTTCCCAGCAGACTCCTTCTGCTGCCAAAACACTTCTCTGTCCACAGC

AACACCAAAGGATGAACAGATCAACTTGCGTCTCCGCGTAGCTTCCTCGGCTAGCGTGCTT

GCAACAGGTCCCTGCACTATTATCTTCCTGCTTTCCTCTGAATTATGCGGCAGGCGAGCGC

TCGCTCTGGCGAGCGCTCCTTCGCGCCGCCCTCGCTGATCGAGTGTACAGTCAATGAATGG

Tgagctccagcgccatgccacgccctttgatggcttcaagtacgattacggtgttggattg tgtgtttgttgcgtagtgtgcatggtttagaataatacacttgatttcttgctcacggcaa tctcggcttgtccgcaggttcaaccccatttcggagtctcaggtcagccgcgcaatgacca gccgctacttcaaggacttgcacgacaacgccgaggtgagctatgtttaggacttgattgg aaattgtcgtcgacgcatattcgcgctccgcgacagcacccaagcaaaatgtcaagtgcgt tccgatttgcgtccgcaggtcgatgttgtgatcgtcggcgccggatccgccggtctgtcct -continued

```
gcgcttacgagctgaccaagcaccctgacgtccgggtacgcgagctgagattcgattagac ataaattgaagattaaacccgtagaaaaatttgatggtcgcgaaactgtgctcgattgcaa gaaattgatcgtcctccactccgcaggtcgccatcatcgagcagggcgttgctcccggcgg cggcgcctggctggggggacagctgttctcggccatgtgtgtacgtagaaggatgaatttc agctggttttcgttgcacagctgtttgtgcatgatttgtttcagactattgttgaatgttt ttagatttcttaggatgcatgatttgtctgcatgcgactGAAGAGCgtttaaacCGCCTCT

CCCCGCGCGTTGGCCGATTCATTAATGCAGCTGGCACGACAGGTTTCCCGACTGGAAAGCG

GGCAGTGAGCGCAACGCAATTAATGTGAGTTAGCTCACTCATTAGGCACCCCAGGCTTTAC

ACTTTATGCTTCCGGCTCGTATGTTGTGTGGAATTGTGAGCGGATAACAATTTCACACAGG

AAACAGCTATGACCATGATTACGCCAAGCTCGAAATTAACCCTCACTAAAGGGAACAAAAG

CTGGCAATTCGCCCTATAGTGAGTCGTATTACGCGCGCTCACTGGCCGTCGTTTTACAACG

TCGTGACTGGGAAAACCCTGGCGTTACCCAACTTAATCGCCTTGCAGCACATCCCCCTTTC

GCCAGCTGGCGTAATAGCGAAGAGGCCCGCACCGATCGCCCTTCCCAACAGTTGCGCAGCC

TGAATGGCGAATGGGACGCGCCCTGTAGCGGCGCATTAAGCGCGGCGGGTGTGGTGGTTAC

GCGCAGCGTGACCGCTACACTTGCCAGCGCCCTAGCGCCCGCTCCTTTCGCTTTCTTCCCT

TCCTTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATGGTTC

ACGTAGTGGGCCATCGCCCTGATAGACGGTTTTTCGCCCTTTGACGTTGGAGTCCACGTTC

TTTAATAGTGGACTCTTGTTCCAAACTGGAACAACACTCAACCCTATCTCGGTCTATTCTT

TTGATTTATAAGGGATTTTGCCGATTTCGGCCTATTGGTTAAAAAATGAGCTGATTTAACA

AAAATTTAACGCGAATTTTAACAAAATATTAACGCTTACAATTTAGGTGGCACTTTTCGGG

GAAATGTGCGCGGAACCCCTATTTGTTTATTTTTCTAAATACATTCAAATATGTATCCGCT

CATGAGACAATAACCCTGATAAATGCTTCAATAATATTGAAAAAGGAAGAGTATGAGTATT

CAACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTGGGTTA

CATCGAACTGGATCTCAACAGCGGTAAGATCCTTGAGAGTTTTCGCCCCGAAGAACGTTTT

CCAATGATGAGCACTTTTAAAGTTCTGCTATGTGGCGCGGTATTATCCCGTATTGACGCCG

GGCAAGAGCAACTCGGTCGCCGCATACACTATTCTCAGAATGACTTGGTTGAGTACTCACC

AGTCACAGAAAAGCATCTTACGGATGGCATGACAGTAAGAGAATTATGCAGTGCTGCCATA

ACCATGAGTGATAACACTGCGGCCAACTTACTTCTGACAACGATCGGAGGACCGAAGGAGC

TAACCGCTTTTTTGCACAACATGGGGGATCATGTAACTCGCCTTGATCGTTGGGAACCGGA

GCTGAATGAAGCCATACCAAACGACGAGCGTGACACCACGATGCCTGTAGCAATGGCAACA

ACGTTGCGCAAACTATTAACTGGCGAACTACTTACTCTAGCTTCCCGGCAACAATTAATAG

ACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTA

TGGATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAAA

AGGATCTAGGTGAAGATCCTTTTTGATAATCTCATGACCAAAATCCCTTAACGTGAGTTTT

CGTTCCACTGAGCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGGTGGTTTGTTTG
```

-continued

CCGGATCAAGAGCTACCAACTCTTTTTCCGAAGGTAACTGGCTTCAGCAGAGCGCAGATAC

CAAATACTGTCCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACCT

ACAGCGTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGCTC

GTCAGGGGGGCGGAGCCTATGGAAAAACGCCAGCAACGCGGCCTTTTTACGGTTCCTGGCC

TTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGA

GTCAGTGAGCGAGGA

SEQ ID NO: 2 - Nucleic acid sequence of construct pSZ6156 for
the expression of the wild-type CpauKASIVa gene in *P.
moriformis* at the DAO1b locus.
Nonspecific or vector sequences are in plain uppercase.
Relevant restriction sites (5' → 3': PmeI, KpnI, AscI, SnaBI,
AvrII, SpeI, NdeI, SacI, and PmeI) are in bold, underlined
lowercase. PmeI sites delimit the 5' and 3' ends of the
transforming DNA. The 5' and 3' homology targeting arms for
integration at the DAO1b locus are in bold lowercase.
Proceeding in the 5' to 3' direction, the PmLDH1v2p promoter
is in boxed, lowercase italics, while the Kozak sequence (ACC)
is in underlined, lowercase italics. The nucleic acid sequence
encoding the native CpSAD1tp transit peptide and the
*Arabidopsis thaliana* THIC *L337M* gene variant (AtTHIC *L337M*), which
is used as the selection marker, are in bold, lowercase italics.
The PmHSP90 3'-UTR is in plain, underlined lowercase. The
buffer DNA sequence that follows is in plain lowercase. The
PmSAD2-1v3p promoter is in boxed, uppercase italics. The
PmSAD1tp transit peptide is in bold, underlined, uppercase
italics, the CpauKASIVa gene (with codon bias for improved
expression in *P. moriformis*) is in bold, uppercase italics, and
the HA epitope tag is double-underlined and in bold, uppercase
italics. The PmSAD2-1 3'-UTR is in plain, underlined
uppercase.
AGCGGAAGAGCGCCCAATgtttaaacagcccgcaccctcgttgatctgggagccctgcgca gcccttaaatcatctcagtcaggtttctgtgttcaactgagcctaaagggctttcgtcat gcgcacgagcacacgtatatcggccacgcagtttctcaaaagcggtagaacagttcgcgag ccctcgtaggtcgaaaacttgcgccagtactattaaattaaattaattgatcgaacgagac gcgaaacttttgcagaatgccaccgagtttgcccagagaatgggagtggcgccattcacca tccgcctgtgcccggcttgattcgccgagacgatggacggcgagaccagggagcggcttgc gagccccgagccggtagcaggaacaatgatcgacaatcttcctgtccaattactggcaacc attagaaagagccggagcgcgttgaaagtctgcaatcgagtaattttcgatacgtcgggc ctgctgaaccctaaggctccggactttgtttaaggcgatccaagatgcacgcggcgcccagg cacgtatctcaagcacaaaccccagccttagtttcgagactttgggagatagcgaccgata tctagtttggcattttgtatattaattacctcaagcaatggagcgctctgatgcggtgcag cgtcggctgcagcacctggcagtggcgctagggtcgccctatcgctcggaacctggtcagc tggctcccgcctcctgctcagcctcttccggtacc[gtaatcccgaggttggccccgcttcc]

[gctggacacccatcgcatcttccggctcgcccgctgtcgagcaagcgccctcgtgcgcgca]

[acccttgtggtgcctgcccgcagagccgggcataaaggcgagcaccacacccgaaccagtc]

caatttgctttctgcattcactcaccaacttttacatccacacatcgtactaccacacctg cccagtcgggtttgatttctattgcaaaggtgcgggggggttggcgcactgcgtgggttgt gcagccggccgccgcggctgtacccagcgatcaggtagcttgggctgtatcttctcaagca ttaccttgtcctgggcgtaggtttgccGCTAGCaccatggccaccgcatccactttctcgg cgttcaatgcccgctgcggcgacctgcgtcgctcggcgggctccgggcccggcgcccagc gaggcccctccccgtgcgcggacgcgccgtccaggccgcggccacccgcttcaagaaggag acgacgaccacccgcgccacgctgacgttcgaccccccacgaccaactccgagcgcgcca agcagcgcaagcacaccatcgacccctcctccccgacttccagcccatcccctccttcga ggagtgcttccccaagtccacgaaggagcacaaggaggtggtgcacgaggagtccggccac gtcctgaaggtgcccttccgccgcgtgcacctgtccggcggcgagcccgccttcgacaact acgacacgtccggcccccagaacgtcaacgcccacatcggcctggcgaagctgcgcaagga gtggatcgaccgccgcgagaagctgggcacgccccgctacacgcagatgtactacgcgaag cagggcatcatcacggaggagatgctgtactgcgcgacgcggagaagctggaccccgagt tcgtccgctccgaggtcgcgcggggccgcgccatcatccctccaacaagaagcacctgga gctggagcccatgatcgtgggccgcaagttcctggtgaaggtgaacgcgaacatcggcaac tccgccgtggcctcctccatcgaggaggaggtctacaaggtgcagtgggccaccatgtggg gcgccgacaccatcatggacctgtccacgggccgccacatccacgagacgcgcgagtggat cctgagcaactccgcggtccccgtgggcaccgtccccatctacaggcgctggagaaggtg gacggcatcgcggagaacctgaactgggaggtgttccgcgagcgctgatcgagcaggccg agcagggcgtggactacttcacgatccacgcgggcgtgctgctgcgctacatcccccctgac cgccaagcgcatgacgggcatcgtgtcccgcggcggctccatccacgcgaagtggtgcctg gcctaccacaaggagaacttcgcctacgagcactgggacgacatcctggacatctgcaacc agtacgacgtcgccctgtccatcggcgacggcctgcgccccggctccatctacgacgccaa cgacacggcccagttcgccgagctgctgacccagggcgagctgacgcgccgcgcgtgggag aaggacgtgcaggtgatgaacgaagggccccggccacgtgcccatgcacaagatccccgaga acatgcagaagcagctggagtggtgcaacgaggcgcccttctacaccctgggcccccctgac gaccgacatcgcgcccggctacgaccacatcacctccgccatcggcgcggccaacatcggc gccctgggcaccgccctgctgtgctacgtgacgcccaaggagcacctgggcctgcccaacc gcgacgacgtgaaggcgggcgtcatcgcctacaagatcgccgcccacgcggccgacctggc caagcagcaccccacgcccaggcgtgggacgacgcgctgtccaaggcgcgcttcgagttc cgctggatggaccagttcgcgctgtccctggaccccatgacggcgatgtccttccacgacg agacgctgcccgcggacggcgcgaaggtcgcccacttctgctccatgtgcgcggccccaagtt ctgctccatgaagatcacggaggacatccgcaagtacgccgaggagaacggctacggctcc gccgaggaggccatccgcccagggcatggacgccatgtccgaggagttcaacatcgccaaga gagacgatctccggcgagcagcacggcgaggtcggcggcgagatctacctgcccgagtccta cgtcaaggccgcgcagaagtgaTACCTTATtacgtaAcagacgaccttggcaggcgtcggg tagggaggtggtggtgatggcgtctcgatgccatcgcacgcatccaacgaccgtatacgca tcgtccaatgaccgtcggtgtcctctctgcctccgttttgtgagatgtctcaggcttggtg -continued catcctcgggtggccagccacgttgcgcgtcgtgctgcttgcctctcttgcgcctctgtgg tactggaaaatatcatcgaggcccgttttttttgctcccatttccttttccgctacatcttga aagcaaacgacaaacgaagcagcaagcaaagagcacgaggacggtgaacaagtctgtcacc tgtatacatctatttccccgcgggtgcacctactctctctcctgccccggcagagtcagct gccttacgtgacGGATCCcgcgtctcgaacagagcgcgcagaggaacgctgaaggtctcgc ctctgtcgcacctcagcgcggcatacaccacaataaccacctgacgaatgcgcttggttct tcgtccattagcgaagcgtccggttcacacacgtgccacgttggcgaggtggcaggtgaca atgatgcggtggagctgatggtcgaaacgttcacagcctaggGATATC GGGAGCAGTTGTCG

ACCGCCCGCGTCCCGCAGGCAGCGATGACGTGTGCGTGGCCTGGGTGTTTCGTCGAAAGGC

CAGCAACCCTAAATCGCAGGCGATCCGGAGATTGGGATCTGATCCGAGTTTGGACCAGATC

CGCCCCGATGCGGCACGGGAACTGCATCGACTCGGCGCGGAACCCAGCTTTCGTAAATGCC

AGATTGGTGTCCGATACCTGGATTTGCCATCAGCGAAACAAGACTTCAGCAGCGAGCGTAT

TTGGCGGGCGTGCTACCAGGGTTGCATACATTGCCCATTTCTGTCTGGACCGCTTTACTGG

CGCAGAGGGTGAGTTGATGGGGTTGGCAGGCATCGAAACGCGCGTGCATGGTGTGCGTGTC

TGTTTTCGGCTGCACGAATTCAATAGTCGGATGGGCGACGGTAGAATTGGGTGTGGCGCTC

GCGTGCATGCCTCGCCCCGTCGGGTGTCATGACCGGGACTGGAATCCCCCCTCGCGACCAT

CTTGCTAACGCTCCCGACTCTCCCGACCGCGCGCAGGATAGACTCTTGTTCAACCAATCGA

CAactagtAcatATGGCTTCCGCGGCATTCACCATGTCGGCGTGCCCCGCGATGACTGGCA

GGGCCCCTGGGGCACGTCGCTCCGGACGGCCAGTCGCCACCCGCCTGAGGGGCTCCACCTT

CCAGTGCCTGGTGAACTCCCACATCGACCCCTGCAACCAGAACGTGTCCTCCGCCTCCCTG

TCCTTCCTGGGCGACAACGGCTTCGGCTCCAACCCCTTCCGCTCCAACCGCGGCCACCGCC

GCCTGGGCCGCGCCTCCCACTCCGGCGAGGCCATGGCCGTGGCCCTGCAGCCCGCCCAGGA

GGTGGCCACCAAGAAGAAGCCCGCCATCAAGCAGCGCCGCGTGGTGGTGACCGGCATGGGC

GTGGTGACCCCCCTGGGCCACGAGCCCGACGTGTTCTACAACAACCTGCTGGACGGCGTGT

CCGGCATCTCCGAGATCGAGACCTTCGACTGCACCCAGTTCCCCACCCGCATCGCCGGCGA

GATCAAGTCCTTCTCCACCGACGGCTGGGTGGCCCCCAAGCTGTCCAAGCGCATGGACAAG

TTCATGCTGTACCTGCTGACCGCCGGCAAGAAGGCCCTGGCCGACGCCGGCATCACCGAGG

ACGTGATGAAGGAGCTGGACAAGCGCAAGTGCGCGTGCTGATCGGCTCCGGCATGGGCGG

CATGAAGCTGTTCAACGACTCCATCGAGGCCCTGCCGTGTCCTACAAGAAGATGAACCCC

TTCTGCGTGCCCTTCGCCACCACCAACATGGGCTCCGCCATGCTGGCCATGGACCTGGGCT

GGATGGGCCCCAACTACTCCATCTCCACCGCCTGCGCCACCTCCAACTTCTGCATCCTGAA

CGCCGCCAACCACATCATCCGCGGCGAGGCCGACATGATGCTGTGCGGCGGCTCCGACGCC

GTGATCATCCCCATCGGCCTGGGCGGCTTCGTGGCCTGCCGCGCCCTGTCCCAGCGCAACT

CCGACCCCACCAAGGCCTCCCGCCCCTGGGACTCCAACCGCGACGGCTTCGTGATGGGCGA

GGGCGCCGGCGTGCTGCTGCTGGAGGAGCTGGAGCACGCCAAGAAGCGCGGCGCCACCATC

TACGCCGAGTTCCTGGGCGGCTCCTTCACCTGCGACGCCTACCACATGACCGAGCCCCACC

CCGACGGCGCCGGCCGTGATCCTGTGCATCGAGAAGGCCCTGGCCCAGTCCGGCGTGTCCCG

CGAGGACGTGAACTACATCAACGCCCACGCCGCCTCCACCCCCGCCGGCGACATCAAGGAG

TACCAGGCCCTGGCCCACTGCTTCGGCCAGAACTCCGAGCTGCGCGTGAACTCCACCAAGT

CCATGATCGGCCACCTGCTGGGCGCCGCCGGCGGCGGGAGGCCGTGACCGT GATCCAGGC

CATCCGCACCGGCTGGATCCACCCCAACCTGAACCTGGAGGACCCCGACGAGGCCGTGGAC

GCCAAGTTCCTGGTGGGCCCCAAGAAGGAGCGCCTGAACGTGAAGGTGGGCCTGTCCAACT

CCTTCGGCTTCGGCGGCCACAACTCCTCCATCCTGTTCGCCCCCTACAACACCATG<u>TACCC</u>

<u>CTACGACGTGCCCGACTACGCC</u>TGAGATATCGGAGCGACGAGTGTGCGTGCGGGGCTGGCG

GGAGTGGGACGCCCTCCTCGCTCCTCTCTGTTCTGAACGGAACAATCGGCCACCCCGCGCT

ACGCGCCACGCATCGAGCAACGAAGAAAACCCCCCGATGATAGGTTGCGGTGGCTGCCGGG

ATATAGATCCGGCCGCACATCAAAGGGCCCCTCCGCCAGAGAAGAAGCTCCTTTCCCAGCA

GACTCCTTCTGCTGCCAAAACACTTCTCTGTCCACAGCAACACCAAAGGATGAACAGATCA

ACTTGCGTCTCCGCGTAGCTTCCTCGGCTAGCGTGCTTGCAACAGGTCCCTGCACTATTAT

CTTCCTGCTTTCCTCTGAATTATGCGGCAGGCGAGCGCTCGCTCTGGCGAGCGCTCCTTCG

CGCCGCCCTCGCTGATCGAGTGTACAGTCAATGAATGG<u>Tgagctc</u>agcgtctgcgtgttgg gagctggagtcgtgggcttgacgacggcgctgcagctgttgcaggatgtgcctggcgtgcg cgttcacgtcgtggctgagaaatatggcgacgaaacgttgacggctggggccggcgggctg tggatgccatacgcattgggtacgcggccattggatgggattgataggcttatggagggat aatagagttttgccggatccaacgcatgtggatgcggtatcccggtgggctgaaagtgtg gaaggatagtgcattggctattcacatgcactgcccaccccttttggcaggaaatgtgccg gcatcgttggtgcaccgatggggaaaatcgacgttcgaccactacatgaagatttatacgt ctgaagatgcagcgactgcgggtgcgaaacggatgacggtttggtcgtgtatgtcacagca tgtgctggatcttgcgggctaactcccctgccacggcccattgcaggtgtcatgttgact ggagggtacgacctttcgtccgtcaaattcccagaggaggacccgctctgggccgacattg tgcccactGAAGAGC<u>gtttaaac</u>CGCCTCTCCCCGCGCGTTGGCCGATTCATTAATGCAGC

TGGCACGACAGGTTTCCCGACTGGAAAGCGGGCAGTGAGCGCAACGCAATTAATGTGAGTT

AGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCTC

GAAATTAACCCTCACTAAAGGGAACAAAAGCTGGCCAATTCGCCCTATAGTGAGTCGTATT

ACAATTCACTGGCCGTCGTTTTACAACGTCGTGACTGGGAAAACCCTGGCGTTACCCAACT

TAATCGCCTTGCAGCACATCCCCCTTTCGCCAGCTGGCGTAATAGCGAAGAGGCCCGCACC

GATCGCCCTTCCCAACAGTTGCGCAGCCTGAATGGCGAATGGGACGCGCCCTGTAGCGGCG

CATTAAGCGCGGCGGGTGTGGTGGTTACGCGCAGCGTGACCGCTACACTTGCCAGCGCCCT

AGCGCCCGCTCCTTTCGCTTTCTTCCCTTCCTTTCTCGCCACGTTCGCCGGCTTTCCCCGT

CAAGCTCTAAATCGGGGGCTCCCTTTAGGGTTCCGATTTAGTGCTTTACGGCACCTCGACC

CCAAAAAACTTGATTAGGGTGATGGTTCACGTAGTGGGCCATCGCCCTGATAGACGGTTTT

TCGCCCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAATATTAAC

-continued

```
GCTTACAATTTAGGTGGCACTTTTCGGGGAAATGTGCGCGGAACCCCTATTTGTTTATTTT

TCTAAATACATTCAAATATGTATCCGCTCATGAGACAATAACCCTGATAAATGCTTCAATA

ATATTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGATGCTG

AAGATCAGTTGGGTGCACGAGTGGGTTACATCGAACTGGATCTCAACAGCGGTAAGATCCT

TGAGAGTTTTCGCCCCGAAGAACGTTTTCCAATGATGAGCACTTTTAAAGTTCTGCTATGT

GGCGCGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCATGAC

AGTAAGAGAATTATGCAGTGCTGCCATAACCATGAGTGATAACACTGCGGCCAACTTACTT

CTGACAACGATCGGAGGACCGAAGGAGCTAACCGCTTTTTTGCACAACATGGGGGATCATG

TAACTCGCCTTGATCGTTGGGAACCGGAGCTGAATGAAGCCATACCAAACGACGAGCGTGA

CACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCAC

TTCTGCGCTCGGCCCTTCCGGCTGGCTGGTTTATTGCTGATAAATCTGGAGCCGGTGAGCG

TGGGTCTCGCGGTATCATTGCAGCACTGGGGCCAGATGGTAAGCCCTCCCGTATCGTAGTT

ATCTACACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTAGAT

TGATTTAAAACTTCATTTTTAATTTAAAAGGATCTAGGTGAAGATCCTTTTTGATAATCTC

ATGACCAAAATCCCTTAACGTGAGTTTTCGTTCCACTGAGCGTCAGACCCCGTAGAAAAGA

TCAAAGGATCTTCTTGAGATCCTTTTTTTCTGCGCGTAATCTGCTGCTTGCAAACAAAAAA

ACCACCGCTACCAGCGGTGGTTTGTTTGCCGGATCAAGAGCTACCAACTCTTTTTCCGAAG

GTAACTGGCTTCAGCAGAGCGCAGATACCAAATACTGTCCTTCTAGTGTAGCCGTAGTTAG

GCCACCACTTCAAGAACTCTGTAGCACCGCCTACATACCTCGCTCTGCTAATCCTGTTACC

AGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACGCTTCC

CGAAGGGAGAAAGGCGGACAGGTATCCGGTAAGCGGCAGGGTCGGAACAGGAGAGCGCACG

AGGGAGCTTCCAGGGGGAAACGCCTGGTATCTTTATAGTCCTGTCGGGTTTCGCCACCTCT

GACTTGAGCGTCGATTTTTGTGATGCTCGTCAGGGGGGCGGAGCCTATGGAAAAACGCCAG

CAACGCGGCCTTTTTACGGTTCCTGGCCTTTTGCTGGCCTTTTGCTCACATGTTCTTTCCT

GCGTTATCCCCTGATTCTGTGGATAACCGTATTACCGCCTTTGAGTGAGCTGATACCGCTC

GCCGCAGCCGAACGACCGAGCGCAGCGAGTCAGTGAGCGAGGA
```

SEQ ID NO: 3 - Amino acid sequence of the wild-type *C. paucipetala* KASIVa (CpauKASIVa) enzyme. The native PmSAD1tp transit peptide is underlined, the HA epitope tag is double underlined, and the amino acid residue T146 is in bold and underlined.

```
MASAAFTMSACPAMTGRAPGARRSGRPVATRLRGSTFQCLVNSHIDPCNQNVSSASLSFL

GDNGFGSNPFRSNRGHRRLGRASHSGEAMAVALQPAQEVATKKKPAIKQRRVVVTGMGVV

TPLGHEPDVFYNNLLDGVSGISEIETFDCTQFPTRIAGEIKSFSTDGWVAPKLSKRMDKF

MLYLLTAGKKALADAGITEDVMKELDKRKCGVLIGSGMGGMKLFNDSIEALRVSYKKMNP

FCVPFATTNMGSAMLAMDLGWMGPNYSISTACATSNFCILNAANHIIRGEADMMLCGGSD

AVIIPIGLGGFVACRALSQRNSDPTKASRPWDSNRDGFVMGEGAGVLLLEELEHAKKRGA
```

-continued

TIYAEFLGGSFTCDAYHMTEPHPDGAGVILCIEKALAQSGVSREDVNYINAHATSTPAGD

IKEYQALAHCFGQNSELRVNSTKSMIGHLLGAAGGVEAVTVIQAIRTGWIHPNLNLEDPD

EAVDAKFLVGPKKERLNVKVGLSNSFGFGGHNSSILFAPYNTM<u>YPYDVPDYA</u>

SEQ ID NO: 4 - Amino acid sequence of the *C. paucipetala* KASIVa
$^{T146X}$ variant (CpauKASIVa $^{T146X}$) enzyme. The native PmSAD1tp
transit peptide is underlined, the HA epitope tag is double
underlined, and the amino acid mutation T146X is in bold and
underlined; X = A, C, D, E, F, G, H, I, K, L, M, N, P, Q, R, S, V, W, or Y.
<u>MASAAFTMSACPAMTGRAPGARRSGRPVATRLRG</u>STFQCLVNSHIDPCNQNVSSASLSFL

GDNGFGSNPFRSNRGHRRLGRASHSGEAMAVALQPAQEVATKKKPAIKQRRVVVTGMGVV

TPLGHEPDVFYNNLLDGVSGISEIE<u>X</u>FDCTQFPTRIAGEIKSFSTDGWVAPKLSKRMDKF

MLYLLTAGKKALADAGITEDVMKELDKRKCGVLIGSGMGGMKLFNDSIEALRVSYKKMNP

FCVPFATTNMGSAMLAMDLGWMGPNYSISTACATSNFCILNAANHIIRGEADMMLCGGSD

AVIIPIGLGGFVACRALSQRNSDPTKASRPWDSNRDGFVMGEGAGVLLLEELEHAKKRGA

TIYAEFLGGSFTCDAYHMTEPHPDGAGVILCIEKALAQSGVSREDVNYINAHATSTPAGD

IKEYQALAHCFGQNSELRVNSTKSMIGHLLGAAGGVEAVTVIQAIRTGWIHPNLNLEDPD

EAVDAKFLVGPKKERLNVKVGLSNSFGFGGHNSSILFAPYNTM<u>YPYDVPDYA</u>

SEQ ID NO: 5 - Amino acid sequence of the CpauFATB1Δ28
thioesterase variant. The modified CpSAD1tp transit peptide is
underlined, and the 3xFLAG tag is double underlined.
<u>MATASTFSAFNARCGDLRRSAGSGPRRPARPLPVRAA</u>INASAHPKANGSAVNLKSGSLNT

QEDTSSSPPPRAFLNQLPDWSMLVDSVGLKSVVLDGLVSRQIFSIRSYEIGADRTASIET

LMNHLQETSINHCKSLGLLNDGFGRTPGMCKNDLIWVLTKMQIMVNRYPTWGDTVEINTW

FSHSGKIGMASDWLITDCNTGEILIRATSVWAMMNQKTRRFSRLPYEVRQELTPHYVDSP

HVIEDNDRKLHKFDVKTGDSIRKGLTPRWNDLDVNQHVSNVKYIGWILESMPIEVLETQE

LCSLTVEYRRECGMDSVLESVTAMDPSEDEGRSQYKHLLRLEDGTDIVKGRTEWRPKNAG

TNGAISTAKPSNGNSVS<u>MDYKDHDGDYKDHDIDYKDDDDK</u>

SEQ ID NO: 6 - Nucleic acid sequence of construct pSZ6871 for
the expression of the CpauKASIVa $^{T146S}$ gene variant in *P.
moriformis* at the THI4 locus.
Nonspecific or vector sequences are in plain uppercase.
Relevant restriction sites (5' → 3': PmeI, KpnI, XbaI, MfeI,
SpeI, EcoRV, SacI, and PmeI) are in bold, underlined lowercase.
PmeI sites delimit the 5' and 3' ends of the transforming DNA.
The 5' and 3' homology targeting arms for integration at the
THI4 locus are in bold lowercase. Proceeding in the 5' to 3'
direction, the CrTUB2 promoter is in boxed, lowercase italics.
The *ScSUC2* selection marker is bold, lowercase italics. The
PmPGH 3'-UTR is in plain, underlined lowercase. The buffer DNA
sequence that follows is in plain lowercase. The PmAMT3v3p
promoter is in boxed, uppercase italics. The PmSAD1tp transit
peptide is in bold, underlined, uppercase italics, the
CpauKASIVa $^{T146S}$ gene variant is in bold, uppercase italics, and
the HA epitope tag is double-underlined and in bold, uppercase
italics. (CCC codons that encode for prolines in specific runs
of 5 or more contiguous cytosines in CpauKASIVa are replaced
with CCG codons to minimize PCR amplification errors.) The
PmSAD2-1 3'-UTR is in plain, underlined uppercase.
AGCGGAAGAGCGCCCAA<u>gtttaaac</u>ccctcaactgcgacgctgggaaccttctccgggca ggcgatgtgcgtgggtttgcctccttggcacggctctacaccgtcgagtacgccatgaggc ggtgatggctgtgtcggttgccacttcgtccagagacggcaagtcgtccatcctctgcgtg tgtggcgcgacgctgcagcagtccctctgcagcagatgagcgtgactttggccatttcacg cactcgagtgtacacaatccattttttcttaaagcaaatgactgctgattgaccagatactg taacgctgatttcgctccagatcgcacagatagcgaccatgttgctgcgtctgaaaatctg gattccgaattcgaccctggcgctccatccatgcaacagatggcgacacttgttacaattc

```
ctgtcacccatcggcatggagcaggtccacttagattcccgatcacccacgcacatctcgc taatagtcattcgttcgtgtcttcgatcaatctcaagtgagtgtgcatggatcttggttga cgatgcggtatgggtttgcgccgctggctgcagggtctgcccaaggcaagctaacccagct cctctccccgacaatactctcgcaggcaaagccggtcacttgccttccagattgccaataa actcaattatggcctctgtcatgccatccatgggtctgatgaatggtcacgctcgtgtcct gaccgttccccagcctctggcgtccctgccccgcccaccagcccacgccgcgcggcagtc gctgccaaggctgtctcggaggtacc cttcttgcgctatgacacttccagcaaaaggtag ggcgggctgcgagacggcttcccggcgctgcatgcaacaccgatgatgcttcgacccccg aagctccttcggggctgcatgggcgctccgatgccgctccagggcgagcgctgtttaaata gccaggccccgattgcaaagacattatagcgagctaccaaagccatattcaaacacctag atcactaccacttctacacaggccactcgagcttgtgatcgcactccgctaaggggggcgcc tcttcctcttcgtttcagtcacaacccgcaaac tctaga ATATCA atgctgctgcaggcct tcctgttcctgctggcaggcttcgccgccaagatcagcgcctccatgacgaacgagacgtc cgaccgcccctggtgcacttcacccccaacaagggctggatgaacgaccccaacggcctg tggtacgacgagaaggacgccaagtggcacctgtacttccagtacaaccgaacgacaccg tctgggggacgcccttgttctggggccacgccacgtccgacgacctgaccaactgggagga ccagcccatcgccatcgccccgaagcgcaacgactccggcgccttctccggctccatggtg gtggactacaacaacacctccggcttcttcaacgacaccatcgacccgcgccagcgctgcg tggccatctggacctacaacacccccggagtccgaggagcagtacatctctacagcctgga cggcggctacaccttcaccgagtaccagaagaacccccgtgctggccgccaactccacccag ttccgcgacccgaaggtcttctggtacgagccctcccagaagtggatcatgaccgcggcca agtcccaggactacaagatcgagatctactcctccgacgacctgaagtcctggaagctgga gtccgcgttcgccaacgagggcttcctcggctaccagtacgagtgccccggcctgatcgag gtccccaccggcaggacccccagcaagtcctactggtgatgttcatctccatcaacccccg gcgccccggccggcggctccttcaaccagtacttcgtcggcagcttcaacggcacccactt cgaggccttcgacaaccagtcccgcgtggtggacttcggcaaggactactacgccctgcag accttcttcaacaccgacccgacctacgggagcgccctgggcatcgcgtgggcctccaact gggagtactccgccttcgtgcccaccaaccctggcgctcctccatgtccctcgtgcgcaa gttctccctcaacaccgagtaccaggccaacccggagacggagctgatcaacctgaaggcc gagccgatcctgaacatcagcaacgccggcccctggagccggttcgccaccaacaccacgt tgacgaaggccaacagctacaacgtcgacctgtccaacagcaccggcacctggagttcga gctggtgtacgccgtcaacaccacccagacgatctccaagtccgtgttcggacctctcc ctctggttcaagggcctggaggaccccgaggagtacctccgcatgggcttcgaggtgtccg cgtcctccttgttcctggaccgcgggaacagcaaggtgaagttcgtgaaggagaaccccta cttcaccaaccgcatgagcgtgaacaaccagcccttcaagagcgagaacgacctgtcctac tacaaggtgtacggcttgctggaccagaacatcctggagctgtacttcaacgacggcgacg tcgtgtccaccaacaccctacttcatgaccaccgggaacgccctgggctccgtgaacatgac gacggggtggacaacctgttctacatcgacaagttccaggtgcgcgaggtcaagtgacaa
```

-continued ttgacgcccgcgcggcgcacctgacctgttctctcgagggcgcctgttctgccttgcgaaa caagcccctggagcatgcgtgcatgatcgtctctggcgccccgccgcgcggtttgtcgccc tcgcgggcgccgcggccgcgggggcgcattgaaattgttgcaaaccccacctgacagattg agggcccaggcaggaaggcgttgagatggaggtacaggagtcaagtaactgaaagttttta tgataactaacaacaaagggtcgtttctggccagcgaatgacaagaacaagattccacatt tccgtgtagaggcttgccatcgaatgtgagcgggcgggccgcggacccgacaaaaccctta cgacgtggtaagaaaaacgtggcgggcactgtccctgtagcctgaagaccagcaggagacg atcggaagcatcacagcacaGGATCCcgcgtctcgaacagagcgcgcagaggaacgctgaa ggtctcgcctctgtcgcacctcagcgcggcatacaccacaataaccacctgacgaatgcgc ttggttcttcgtccattagcgaagcgtccggttcacacacgtgccacgttggcgaggtggc aggtgacaatgatcggtggagctgatggtcgaaacgttcacagcctaggGATT│*ATCAAAAA*

│*CGCCTGAGACACTTGCCCAGGATTGAAACTCCCTGAAGGGACCACCAGGGGCCCTGAGTTG*│

│*TTCCTTCCCCCCGTGGCGAGCTGCCAGCCAGGCTGTACCTGTGATCGGGGCTGGCGGGAAA*│

│*ACAGGCTTCGTGTGCTCAGGTTATGGGAGGTGCAGGACAGCTCATTAAACGCCAACAATCG*│

│*CACAATTCATGGCAAGCTAATCAGTTATTTCCCATTAACGAGCTATAATTGTCCCAAAATT*│

│*CTGGTCTACCGGGGGTGATCCTTCGTGTACGGGCCCTTCCCTCAACCCTAGGTATGCGCAC*│

│*ATGCGGTCGCCGCGCAACGCGCGCGAGGGCCGAGGGTTTGGGACGGGCCGTCCCGAAATGC*│

│*AGTTGCACCCGGATGCGTGGCACCTTTTTTGCGATAATTTATGCAATGGACTGCTCTGCAA*│

│*AATTCTGGCTCTGTCGCCAACCCTAGGATCAGCGGTGTAGGATTTCGTAATCATTCGTCCT*│

│*GATGGGGAGCTACCGACTGCCCTAGTATCAGCCCGACTGCCTGACGCCAGCGTCCACTTTT*│

│*GTGCACACATTCCATTCGTGCCCAAGACATTTCATTGTGGTGCGAAGCGTCCCCAGTTACG*│

│*CTCACCTGATCCCCAACCTCCTTATTGTTCTGTCGACAGAGTGGGCCCAGAGGCCGGTCGC*│

│*AGCC*│actagtACAT*ATGGCTTCCGCGGCATTCACCATGTCGGCGTGCGCCGCGATGACTGG*

*CAGGGCCCCTGGGGCACGTCGCTCCGGACGGCCAGTCGCCACCCACCTGAGG* *GGCTCCACC*

*TTCCAGTGCCTGGTGAACTCCCACATCGACCCCTGCAACCAGAACGTGTCCTCCGCCTCCC*

*TGTCCTTCCTGGGCGACAACGGCTTCGGCTCCAACCCCTTCCGCTCCAACCGCGGCCACCG*

*CCGCCTGGGCCGCGCCTCCCACTCCGGCGAGGCCATGGCCGTGGCCCTGCAGCCCGCCCAG*

*GAGGTGGCCACCAAGAAGAAGCCCGCCATCAAGCAGCGCCGCGTGGTGGTGACCGGCATGG*

*GCGTGGTGACCCCGCTGGGCCACGAGCCCGACGTGTTCTACAACAACCTGCTGGACGGCGT*

*GTCCGGCATCTCCGAGATCGAGAGCTTCGACTGCACCCAGTTCCCCACCCGCATCGCCGGC*

*GAGATCAAGTCCTTCTCCACCGACGGCTGGGTGGCCCCGAAGCTGTCCAAGCGCATGGACA*

*AGTTCATGCTGTACCTGCTGACCGCCGGCAAGAAGGCCCTGGCCGACGCCGGCATCACCGA*

*GGACGTGATGAAGGAGCTGGACAAGCGCAAGTGCGGCGTGCTGATCGGCTCCGGCATGGGC*

*GGCATGAAGCTGTTCAACGACTCCATCGAGGCCCTGCGCGTGTCCTACAAGAAGATGAACC*

*CCTTCTGCGTGCCCTTCGCCACCACCAACATGGGCTCCGCCATGCTGGCCATGGACCTGGG*

-continued

*CTGGATGGGCCCCAACTACTC CATCTCCACCGCCTGCGCCACCTCCAACTTCTGCATCCTG*

*AACGCCGCCAACCACATCATCCGCGGCGAGGCCGACATGATGCTGTGCGGCGGCTCCGACG*

*CCGTGATCATCCCCATCGGCCTGGGCGGCTTCGTGGCCTGCCGCGCCCTGTCCCAGCGCAA*

*CTCCGACCCCACCAAGGCCTCCGCCCCTGGGACTCCAACCGCGACGGCTTCGTGATGGGC*

*GAGGGCGCCGGCGTGCTGCTGCTGGAGGAGCTGGAGCACGCCAAGAAGCGCGGCGCCACCA*

*TCTACGCCGAGTTCCTGGGCGGCTCCTTCACCTGCGACGCCTACCACATGACCGAGCCGCA*

*CCCCGGACGGCGCCGGCGTGATCCTGTGCATCGAGAAGGCCCTGGCCCAGTCCGGCGTGTCC*

*CGCGAGGACGTGAACTACATCAACGCCCACGCCACCTCCACCCCGGCCGGCGACATCAAGG*

*AGTACCAGGCCCTGGCCCACTGCTTCGGCCAGAACTCCGAGCTGCGCGTGAACTCCACCAA*

*GTCCATGATCGGCCACCTGCTGGGCGCCGCCGGCGGCGTGGAGGCCGTGACCGTGATCCAG*

*GCCATCCGCACCGGCTGGATCCACCCCAACCTGAACCTGGAGGACCCCGACGAGGCCGTGG*

*ACGCCAAGTTCCTGGTGGGCCCCAAGAAGGAGCGCCTGAACGTGAAGGTGGGCCTGTCCA*

*CTCCTTCGGCTTCGGCGGCCACAACTCCTCCATCCTGTTCGCCCCGTACAACACCATGTAC*
<u>*CCCTACGACGTGCCCGACTACGCC*</u>*TGA</u>gatatc<u>GGAGCGACGAGTGTGCGTGCGGGGCTGG*</u>

<u>CGGGAGTGGGACGCCCTCCTCGCTCCTCTCTGTTCTGAACGGAACAATCGGCCACCCCGCG</u>

<u>CTACGCGCCACGCATCGAGCAACGAAGAAAACCCCCCGATGATAGGTTGCGGTGGCTGCCG</u>

<u>GGATATAGATCCGGCCGCACATCAAAGGGCCCCTCCGCCAGAGAAGAAGCTCCTTTCCCAG</u>

<u>CAGACTCCTTCTGCTGCCAAAACACTTCTCTGTCCACAGCAACACCAAAGGATGAACAGAT</u>

<u>CAACTTGCGTCTCCGCGTAGCTTCCTCGGCTAGCGTGCTTGCAACAGGTCCCTGCACTATT</u>

<u>ATCTTCCTGCTTTCCTCTGAATTATGCGGCAGGCGAGCGCTCGCTCTGGCGAGCGCTCCTT</u>

<u>CGCGCCGCCCTCGCTGATCGAGTGTACAGTCAATGAATGGT<b>gagctc</b></u>cagcgccatgccac gcccttgatggcttcaagtacgattacggtgttggattgtgtgtttgttgcgtagtgtgc atggtttagaataatacacttgatttcttgctcacggcaatctcggcttgtccgcaggttc aaccccatttcggagtctcaggtcagccgcgcaatgaccagccgctacttcaaggacttgc acgacaacgccgaggtgagctatgtttaggacttgattggaaattgtcgtcgacgcatatt cgcgctccgcgacagcacccaagcaaaatgtcaagtgcgttccgatttgcgtccgcaggtc gatgttgtgatcgtcggcgccggatccgccggtctgtcctgcgcttacgagctgaccaagc accctgacgtccgggtacgcgagctgagattcgattagacataaattgaagattaaacccg tagaaaatttgatggtcgcgaaactgtgctcgattgcaagaaattgatcgtcctccactc cgcaggtcgccatcatcgagcagggcgttgctcccggcggcggcgcctggctggggggaca gctgttctcggccatgtgtgtacgtagaaggatgaatttcagctggttttcgttgcacagc tgtttgtgcatgatttgtttcagactattgttgaatgttttagatttcttaggatgcatg atttgtctcatgcgact<u>GAAGAG<b>gtttaaac</b>CGCCTCTCCCCGCGCGTTGGCCGATTCA</u>

TTAATGCAGCTGGCACGACAGGTTTCCCGACTGGAAAGCGGGCAGTGAGCGCAACGCAATT

AATGTGAGTTAGCTCACTCATTAGGCACCCCAGGCTTTACACTTTATGCTTCCGGCTCGTA

TGTTGTGTGGAATTGTGAGCGGATAACAATTTCACACAGGAAACAGCTATGACCATGATTA

CGCCAAGCTCGAAATTAACCCTCACTAAAGGGAACAAAAGCTGGCAATTCGCCCTATAGTG

AGTCGTATTACGCGCGCTCACTGGCCGTCGTTTTACAACGTCGTGACTGGGAAAACCCTGG

CGTTACCCAACTTAATCGCCTTGCAGCACATCCCCCTTTCGCCAGCTGGCGTAATAGCGAA

GAGGCCCGCACCGATCGCCCTTCCCAACAGTTGCGCAGCCTGAATGGCGAATGGGACGCGC

CCTGTAGCGGCGCATTAAGCGCGGCGGGTGTGGTGGTTACGCGCAGCGTGACCGCTACACT

-continued

```
TGCCAGCGCCCTAGCGCCCGCTCCTTTCGCTTTCTTCCCTTCCTTTCTCGCCACGTTCGCC

GGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTG

ATAGACGGTTTTTCGCCCTTTGACGTTGGAGTCCACGTTCTTTAATAGTGGACTCTTGTTC

CAAACTGGAACAACACTCAACCCTATCTCGGTCTATTCTTTTGATTTATAAGGGATTTTGC

CGATTTCGGCCTATTGGTTAAAAAATGAGCTGATTTAACAAAAATTTAACGCGAATTTTAA

CAAAATATTAACGCTTACAATTTAGGTGGCACTTTTCGGGGAAATGTGCGCGGAACCCCTA

TTTGTTTATTTTTCTAAATACATTCAAATATGTATCCGCTCATGAGACAATAACCCTGATA

AATGCTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGAAAG

TAAAAGATGCTGAAGATCAGTTGGGTGCACGAGTGGGTTACATCGAACTGGATCTCAACAG

CGGTAAGATCCTTGAGAGTTTTCGCCCCGAAGAACGTTTTCCAATGATGAGCACTTTTAAA

GTTCTGCTATGTGGCGCGGTATTATCCCGTATTGACGCCGGGCAAGAGCAACTCGGTCGCC

GCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCG

GCCAACTTACTTCTGACAACGATCGGAGGACCGAAGGAGCTAACCGCTTTTTTGCACAACA

TGGGGGATCATGTAACTCGCCTTGATCGTTGGGAACCGGAGCTGAATGAAGCCATACCAAA

CGACGAGCGTGACACCACGATGCCTGTAGCAATGGCAACAACGTTGCGCAAACTATTAACT

GGCGAACTACTTACTCTAGCTTCCCGGCAACAATTAATAGACTGGATGGAGGCGGATAAAG

TTGCAGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGCCCTCC

CGTATCGTAGTTATCTACACGACGGGGAGTCAGGCAACTATGGATGAACGAAATAGACAGA

TCGCTGAGATAGGTGCCTCACTGATTAAGCATTGGTAACTGTCAGACCAAGTTTACTCATA

TATACTTTAGATTGATTTAAAACTTCATTTTTAATTTAAAAGGATCTAGGTGAAGATCCTT

TTTGATAATCTCATGACCAAAATCCCTTAACGTGAGTTTTCGTTCCACTGAGCGTCAGACC

CCGTAGAAAAGATCAAAGGATCTTCTTGAGATCCTTTTTTTCTGCGCGTAATCTGCTGCTT

GCAAACAAAAAAACCACCGCTACCAGCGGTGGTTTGTTTGCCGGATCAAGAGCTACCAACT

CTTTTTCCGAAGGTAACTGGCTTCAGCAGAGCGCAGATACCAAATACTGTCCTTCTAGTGT

AGCCGTAGTTAGGCCACCACTTCAAGAACTCTGTAGCACCGCCTACATACCTCGCTCTGCT

AATCCTGTTACCAGTGGCTGCTGCCAGTGGCGATAAGTCGTGTCTTACCGGGTTGGACTCA

AGACGATAGTTACCGGATAAGGCGCAGCGGTCGGGCTGAACGGGGGGTTCGTGCACACAGC

CCAGCTTGGAGCGAACGACCTACACCGAACTGAGATACCTACAGCGTGAGCTATGAGAAAG

CGCCACGCTTCCCGAAGGGAGAAAGGCGGACAGGTATCCGGTAAGCGGCAGGGTCGGAACA

GGAGAGCGCACGAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGGCGGAGCCTATG

GAAAAACGCCAGCAACGCGGCCTTTTTACGGTTCCTGGCCTTTTGCTGGCCTTTTGCTCAC

ATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGA
```

SEQ ID NO: 7 - Nucleic acid sequence of the wild-type CpauKASIVa
gene in construct pSZ6757 with codon bias for improved
expression in *P. moriformis*. (CCC codons that encode for
prolines in specific runs of 4 or more contiguous cytosines in CpauKASIVa are replaced with CCG codons to minimize PCR
amplification errors.) The PmSAD1tp transit peptide is
underlined, and the HA epitope tag is double-underlined. The
rest of construct pSZ6757 is identical to SEQ ID NO: 6.
<u>ATGGCTTCCGCGGCATTCACCATGTCGGCGTGCCCCGCGATGACTGGCAGGGCCCCTGGGG</u>

<u>CACGTCGCTCCGGACGGCCAGTCGCCACCCGCCTGAGGGG</u>CTCCACCTTCCAGTGCCTGGT

GAACTCCCACATCGACCCCTGCAACCAGAACGTGTCCTCCGCCTCCCTGTCCTTCCTGGGC

GACAACGGCTTCGGCTCCAACCCCTTCCGCTCCAACCGCGGCCACCGCCGCCTGGGCCGCG

CCTCCCACTCCGGCGAGGCCATGGCCGTGGCCCTGCAGCCCGCCCAGGAGGTGGCCACCAA

GAAGAAGCCCGCCATCAAGCAGCGCCGCGTGGTGGTGACCGGCATGGGCGTGGTGACCCCG

CTGGGCCACGAGCCCGACGTGTTCTACAACAACCTGCTGGACGGCGTGTCCGGCATCTCCG

AGATCGAGACCTTCGACTGCACCCAGTTCCCCACCCGCATCGCCGGCGAGATCAAGTCCTT

CTCCACCGACGGCTGGGTGGCCCCGAAGCTGTCCAAGCGCATGGACAAGTTCATGCTGTAC

CTGCTGACCGCCGGCAAGAAGGCCCTGGCCGACGCCGGCATCACCGAGGACGTGATGAAGG

AGCTGGACAAGCGCAAGTGCGGCGTGCTGATCGGCTCCGGCATGGGCGGCATGAAGCTGTT

CAACGACTCCATCGAGGCCCTGCGCGTGTCCTACAAGAAGATGAACCCCTTCTGCGTGCCC

TTCGCCACCACCAACATGGGCTCCGCCATGCTGGCCATGGACCTGGGCTGGATGGGCCCCA

ACTACTCCATCTCCACCGCCTGCGCCACCTCCAACTTCTGCATCCTGAACGCCGCCAACCA

CATCATCCGCGGCGAGGCCGACATGATGCTGTGCGGCGGCTCCGACGCCGTGATCATCCCC

ATCGGCCTGGGCGGCTTCGTGGCCTGCCGCGCCCTGTCCCAGCGCAACTCCGACCCCACCA

AGGCCTCCCGCCCCTGGGACTCCAACCGCGACGGCTTCGTGATGGGCGAGGGCGCCGGCGT

GCTGCTGCTGGAGGAGCTGGAGCACGCCAAGAAGCGCGGCGCCACCATCTACGCCGAGTTC

CTGGGCGGCTCCTTCACCTGCGACGCCTACCACATGACCGAGCCGCCACCCGGACGGCGCCG

GCGTGATCCTGTGCATCGAGAAGGCCCTGGCCCAGTCCGGCGTGTCCCGCGAGGACGTGAA

CTACATCAACGCCCACGCCACCTCCACCCCGGCCGGCGACATCAAGGAGTACCAGGCCCTG

GCCCACTGCTTCGGCCAGAACTCCGAGCTGCGCGTGAACTCCACCAAGTCCATGATCGGCC

ACCTGCTGGGCGCCGCCGGCGGCGTGGAGGCCGTGACCGTGATCCAGGCCATCCGCACCGG

CTGGATCCACCCCAACCTGAACCTGGAGGACCCCGACGAGGCCGTGGACGCCAAGTTCCTG

GTGGGCCCCAAGAAGGAGCGCCTGAACGTGAAGGTGGGCCTGTCCAACTCCTTCGGCTTCG

GCGGCCACAACTCCTCCATCCTGTTCGCCCCGTACAACACCATG<u>TACCCCTACGACGTGCC</u>

<u>CGACTACGCCTGA</u>

SEQUENCE ID NO: 8 - Nucleic acid sequence of construct pSZ6712
for the expression of the CpauFATB1Δ28 thioesterase gene
variant in *P. moriformis* at the DAO1b locus.
Nonspecific or vector sequences are in plain uppercase.
Relevant restriction sites (5' → 3': PmeI, KpnI, AscI, SnaBI,
SpeI, XhoI, SacI, and PmeI) are in bold, underlined lowercase.
PmeI sites delimit the 5' and 3' ends of the transforming DNA.
The 5' and 3' homology targeting arms for integration at the
DAO1b locus are in bold lowercase. Proceeding in the 5' to 3'
direction, the PmHXT1-2v2p promoter is in boxed, lowercase
italics, while the Kozak sequence (ACC) is in underlined
lowercase italics. The nucleic acid sequence encoding the
native CpSAD1tp transit peptide and the *Arabidopsis thaliana*
THIC *L337M* gene variant (AtTHIC *L337M*), which is used as the
selection marker, are in bold, lowercase italics. The PmHSP90
3'-UTR is in plain, underlined lowercase. The buffer DNA
sequence that follows is in plain lowercase. The PmAMT3v3p
promoter is in boxed, uppercase italics. The modified (with
codon bias for improved expression in *P. moriformis*) CpSAD1tp
is in bold, underlined, uppercase italics, the nucleic acid
encoding CpauFATB1Δ28 thioesterase gene (with codon bias for
improved expression in *P. moriformis*) is in bold, uppercase
italics, and the 3xFLAG tag is double-underlined and in bold, uppercase italics. (CCC codons that encode for prolines in
specific runs of 6 or more contiguous cytosines in CpauFATB1Δ28
are replaced with CCG codons to minimize PCR amplification
errors.) The PmSAD2-1 3'-UTR is in plain, underlined
uppercase.

GATCTTCTTGAGATCCTTTTTTTCTGCGCGTAATCTGCTGCTTGCAAACAAAAAAACCACC

GCTACCAGCGGTGGTTTGTTTGCCGGATCAAGAGCTACCAACTCTTTTTCCGAAGGTAACT

GGCTTCAGCAGAGCGCAGATACCAAATACTGTCCTTCTAGTGTAGCCGTAGTTAGGCCACC

ACTTCAAGAACTCTGTAGCACCGCCTACATACCTCGCTCTGCTAATCCTGTTACCAGTGGC

TGCTGCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCACGAGGGAG

CTTCCAGGGGGAAACGCCTGGTATCTTTATAGTCCTGTCGGGTTTCGCCACCTCTGACTTG

AGCGTCGATTTTTGTGATGCTCGTCAGGGGGGCGGAGCCTATGGAAAAACGCCAGCAACGC

GGCCTTTTTACGGTTCCTGGCCTTTTGCTGGCCTTTTGCTCACATGTTCTTTCCTGCGTTA

TCCCCTGATTCTGTGGATAACCGTATTACCGCCTTTGAGTGAGCTGATACCGCTCGCCGCA

GCCGAACGACCGAGCGCAGCGAGTCAGTGAGCGAGGAAGCGGAAGAGCGCCCAAT<u>gtttaa</u>

<u>ac</u>agcccgcaccctcgttgatctgggagccctgcgcagcccctt aaatcatctcagtcagg tttctgtgttcaactgagcctaaagggctttcgtcatgcgcacgagcacacgtatatcggc cacgcagtttctcaaaagcggtagaacagttcgcgagccctcgtaggtcgaaaacttgcgc cagtactattaaattaaattaattgatcgaacgagacgcgaaacttttgcagaatgccacc gagtttgcccagagaatgggagtggcgccattcaccatccgcctgtgcccggcttgattcg ccgagacgatggacggcgagaccagggagcggcttgcgagccccgagccggtagcaggaac aatgatcgacaatcttcctgtccaattactggcaaccattagaaagagccggagcgcgttg aaagtctgcaatcgagtaatttttcgatacgtcgggcctgctgaaccctaaggctccggac tttgtttaaggcgatccaagatgcacgcggccccaggcacgtatctcaagcacaaacccca gccttagtttcgagactttgggagatagcgaccgatatctagtttggcattttgtatatta attacctcaagcaatggagcgctctgatgcggtgcagcgtcggctgcagcacctggcagtg gcgctagggtcgccctatcgctcggaacctggtcagctggctcccgcctcctgctcagcct cttcc<u>ggtacc</u>|ccgctccgtctggtcctcacgttcgtgtacggcctggatcccggaaagg|

|gcggatgcacgtggtgttgccccgccattggcgcccacgtttcaaagtccccggccagaaa|

|tgcacaggaccggcccggctcgcacaggccatgacgaatgcccagatttcgacagcaaaac|

|aatctggaataatcgcaaccattcgcgttttgaacgaaacgaaaagacgctgtttagcacg|

|tttccgatatcgtgggggccgaagcatgattggggggaggaaagcgtggccccaaggtagc|

|ccattctgtgccacacgccgacgaggaccaatccccggcatcagccttcatcgacggctgc|

|gccgcacatataaagccggacgccttcccgacacgttcaaacagttttatttcctccactt|

|cctgaatcaaacaaatcttcaaggaagatcctgctcttgagca|GCTAGC<u>ACC</u>atggccacc gcatccactttctcggcgttcaatgcccgctgcggcgacctgcgtcgctcggcgggctccg ggccccggcgcccagcgaggcccctcccgtgcgcg<u>ggcgcgcc</u> cgcgccacgctgacgtt -continued

```
cgacccccccacgaccaactccgagcgcgccaagcagcgcaagcacaccatcgacccctcc tccccgacttccagcccatccctccttcgaggagtgcttccccaagtccacgaaggagc acaaggaggtggtgcacgaggagtccggccacgtcctgaaggtgcccttccgccgcgtgca cctgtccggcggcgagcccgccttcgacaactacgacacgtccggccccccagaacgtcaac gcccacatcggcctggcgaagctgcgcaaggagtggatcgaccgccgcgagaagctgggca cgccccgctacacgcagatgtactacgcgaagcagggcatcatcacggaggagatgctgta ctgcgcgacgcgcgagaagctggaccccgagttcgtccgctccgaggtcgcgcgggccgc gccatcatcccctccaacaagaagcacctggagctggagcccatgatcgtgggccgcaagt tcctggtgaaggtgaacgcgaacatcggcaactccgccgtggcctcctccatcgaggagga ggtctacaaggtgcagtgggccaccatgtggggcgccgacaccatcatggacctgtccacg ggccgccacatccacgagacgcgcgagtggatcctgcgcaactccgcggtccccgtgggca ccgtccccatctaccaggcgctggagaaggtggacggcatcgcggagaacctgaactggga ggtgttccgcgagacgctgatcgagcaggccgagcagggcgtggactacttcacgatccac gcgggcgtgctgctgcgctacatccccctgaccgccaagcgcatgacgggcatcgtgtccc gcggcggctccatccacgcgaagtggtgcctggcctaccacaaggagaacttcgcctacga gcactgggacgacatcctggacatctgcaaccagtacgacgtcgccctgtccatcggcgac ggcctgcgcccggctccatctacgacgccaacgacacggcccagttcgccgagctgctga cccagggcgagctgacgcgccgcgcgtgggagaaggacgtgcaggtgatgaacgagggccc cggccacgtgcccatgcacaagatccccgagaacatgcagaagcagctggagtggtgcaac gaggcgcccttctacaccctgggcccccctgacgaccgacatcgcgcccggctacgaccaca tcacctccgccatcggcgcggccaacatcggcgcgccctgggcaccgccctgctgtgctacgt gacgcccaaggagcacctgggcctgcccaaccgcgacgacgtgaaggcgggcgtcatcgcc tacaagatcgccgcccacgcggccgacctggccaagcagcaccccacgcccaggcgtggg acgacgcgctgtccaaggcgcgcttcgagttccgctggatggaaccagttcgcgctgtccct ggaccccatgacggcgcgatgtccttccacgacgagacgctgcccgcgggacggcgcgaaggtc gcccacttctgctccatgtgcggccccaagttctgctccatgaagatcacggaggacatcc gcaagtacgccgaggagaacggctacggctccgcgaggaggccatccgccagggcatgga cgccatgtccgaggagttcaacatcgccaagaagacgatctccggcgagcagcacggcgag gtcggcggcgagatctacctgcccgagtcctacgtcaaggccgcgcagaagtgaTACCTTA TtacgtaAcagacgaccttggcaggcgtcgggtagggaggtggtggtgatggcgtctcgat gccatcgcacgcatccaacgaccgtatacgcatcgtccaatgaccgtcggtgtcctctctg cctccgtttttgtgagatgtctcaggcttggtgcatcctcgggtggccagccacgttgcgcg tcgtgctgcttgcctctcttgcgcctctgtggtactggaaaatatcatcgaggcccgtttt tttgctcccatttcctttccgctacatcttgaaagcaaacgacaaacgaagcagcaagcaa agagcacgaggacggtgaacaagtctgtcacctgtatacatctatttccccgcgggtgcac ctactctctctcctgccccggcagagtcagctgccttacgtgacGGATCCcgcgtctcgaa cagagcgcgcagaggaacgctgaaggtctcgcctctgtcgcacctcagcgcggcatacacc acaataaccacctgacgaatgcgcttggttcttcgtccattagcgaagcgtccggttcaca cacgtgccacgttggcgaggtggcaggtgacaatgatcggtggagctgatggtcgaaacgt tcacagcctaggGATATCATCAAAAACGCCTGAGACACTTGCCCAGGATTGAAACTCCCTG
```

-continued

AAGGGACCACCAGGGGCCCTGAGTTGTTCCTTCCCCCCGTGGCGAGCTGCCAGCCAGGCTG

TACCTGTGATCGGGGCTGGCGGGAAAACAGGCTTCGTGTGCTCAGGTTATGGGAGGTGCAG

GACAGCTCATTAAACGCCAACAATCGCACAATTCATGGCAAGCTAATCAGTTATTTCCCAT

TAACGAGCTATAATTGTCCCAAAATTCTGGTCTACCGGGGGTGATCCTTCGTGTACGGGCC

CTTCCCTCAACCCTAGGTATGCGCACATGCGGTCGCCGCGCAACGCGCGCGAGGGCCGAGG

GTTTGGGACGGGCCGTCCCGAAATGCAGTTGCACCCGGATGCGTGGCACCTTTTTTGCGAT

AATTTATGCAATGGACTGCTCTGCAAAATTCTGGCTCTGTCGCCAACCCTAGGATCAGCGG

TGTAGGATTTCGTAATCATTCGTCCTGATGGGGAGCTACCGACTGCCCTAGTATCAGCCCG

ACTGCCTGACGCCAGCGTCCACTTTTGTGCACACATTCCATTCGTGCCCAAGACATTTCAT

TGTGGTGCGAAGCGTCCCCAGTTACGCTCACCTGATCCCCAACCTCCTTATTGTTCTGTCG

ACAGAGTGGGCCCAGAGGCCGGTCGCAGCCactagtAACAATGGCCACCGCCTCCACCTTC

TCCGCCTTCAACGCCCGCTGCGGCGACCTGCGCCGCTCCGCCGGCTCCGGCCCCCGCCGCC

CCGCCCGCCCCCTGCCCGTGCGCGCCGCCATCAACGCCTCCGCCCACCCCAAGGCCAACGG

CTCCGCCGTGAACCTGAAGTCCGGCTCCCTGAACACCCAGGAGGACACCTCCTCCTCTCCG

CCTCCCCGCGCCTTCCTGAACCAGCTGCCCGACTGGTCCATGCTGGTGGACTCCGTGGGCC

TGAAGTCCGTGGTGCTGGACGGCCTGGTGTCCCGCCAGATCTTCTCCATCCGCTCCTACGA

GATCGGCGCCGACCGCACCGCCTCCATCGAGACCCTGATGAACCACCTGCAGGAGACCTCC

ATCAACCACTGCAAGTCCCTGGGCCTGCTGAACGACGGCTTCGGCCGCACCCCCGGCATGT

GCACCCCCGGCATGATCTGGGTGCTGACCAAGATGCAGATCATGGTGAACCGCTACCCCAC

CTGGGGCGACACCGTGGAGATCAACACCTGGTTCTCCCACTCCGGCAAGATCGGCATGGCC

TCCGACTGGCTGATCACCGACTGCAACACCGGCGAGATCCTGATCCGCGCCACCTCCGTGT

GGGCCATGATGAACCAGAAGACC CGCCGCTTCTCCCGCCTGCCCTACGAGGTGCGCCAGGA

GCTGACCCCTCACTACGTGGACTCCCCGCACGTGATCGAGGACAACGACCGCAAGCTGCAC

AAGTTCGACGTGAAGACCGGCGACTCCATCCGCAAGGGCCTGACCCCTCGCTGGAACGACC

TGGACGTGAACCAGCACGTGTCCAACGTGAAGTACATCGGCTGGATCCTGGAGTCCATGCC

CATCGAGGTGCTGGAGACCCAGGAGCTGTGCTCCCTGACCGTGGAGTACCGCCGCGAGTGC

GGCATGGACTCCGTGCTGGAGTCCGTGACCGCCATGGACCCCTCCGAGGACGAGGGCCGCT

CCCAGTACAAGCACCTGCTGCGCCTGGAGGACGGCACCGACATCGTGAAGGGCCGCACCGA

GTGGCGCCCCAAGAACGCCGGCACCAACGGCGCCATCTCCACCGCCAAGCCCTCCAACGGC

AACTCCGTGTCCATGGACTACAAGGACCACGACGGCGACTACAAGGACCACGACATCGACT

ACAAGGACGACGACGACAAGTGActcgagGGAGCGACGAGTGTGCGTGCGGGGCTGGCGGG

AGTGGGACGCCCTCCTCGCTCCTCTCTGTTCTGAACGGAACAATCGGCCACCCCGCGCTAC

GCGCCACGCATCGAGCAACGAAGAAAACCCCCCGATGATAGGTTGCGGTGGCTGCCGGGAT

ATAGATCCGGCCGCACATCAAAGGGCCCCTCCGCCAGAGAAGAAGCTCCTTTCCCAGCAGA

CTCCTTCTGCTGCCAAAACACTTCTCTGTCCACAGCAACACCAAAGGATGAACAGATCAAC

```
TTGCGTCTCCGCGTAGCTTCCTCGGCTAGCGTGCTTGCAACAGGTCCCTGCACTATTATCT

TCCTGCTTTCCTCTGAATTATGCGGCAGGCGAGCGCTCGCTCTGGCGAGCGCTCCTTCGCG

CCGCCCTCGCTGATCGAGTGTACAGTCAATGAATGGTgagctcagcgtctgcgtgttggga gctggagtcgtgggcttgacgacggcgctgcagctgttgcaggatgtgcctggcgtgcgcg ttcacgtcgtggctgagaaatatggcgacgaaacgttgacggctggggccggcgggctgtg gatgccatacgcattgggtacgcggccattggatgggattgataggcttatggagggataa tagagtttttgccggatccaacgcatgtggatgcggtatcccggtgggctgaaagtgtgga aggatagtgcattggctattcacatgcactgcccaccccttttggcaggaaatgtgccggc atcgttggtgcaccgatggggaaaatcgacgttcgaccactacatgaagatttatacgtct gaagatgcagcgactgcgggtgcgaaacggatgacggtttggtcgtgtatgtcacagcatg tgctggatcttgcgggctaactcccctgccacggcccattgcaggtgtcatgttgactgg agggtacgacctttcgtccgtcaaattcccagaggaggacccgctctgggccgacattgtg cccactGAAGAGgtttaaacCGCCTCTCCCCGCGCGTTGGCCGATTCATTAATGCAGCTG

GCACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGGAA

TTGTGAGCGGATAACAATTTCACACAGGAAACAGCTATGACCATGATTACGCCAAGCTCGA

AATTAACCCTCACTAAAGGGAACAAAAGCTGGCCAATTCGCCCTATAGTGAGTCGTATTAC

AATTCACTGGCCGTCGTTTTACAACGTCGTGACTGGGAAAACCCTGGCGTTACCCAACTTA

ATCGCCTTGCAGCACATCCCCCTTTCGCCAGCTGGCGTAATAGCGAAGAGGCCCGCACCGA

TCGCCCTTCCCAACAGTTGCGCAGCCTGAATGGCGAATGGGACGCGCCCTGTAGCGGCGCA

TTAAGCGCGGCGGGTGTGGTGGTTACGCGCAGCGTGACCGCTACACTTGCCAGCGCCCTAG

CGCCCGCTCCTTTCGCTTTCTTCCCTTCCTTTCTCGCCACGTTCGCCGGCTTTCCCCGTCA

AGCTCTAAATCGGGGGCTCCCTTTAGGGTTCCGATTTAGTGCTTTACGGCACCTCGACCCC

AAAAAACTTGATTAGGGTGATGGTTCACGTAGTGGGCCATCGCCCTGATAGACGGTTTTTC

GCCCTTTGACGTTGGAGTCCACGTTCTTTAATAGTGGACTCTTGTTCCAAACTGGAACAAC

ACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGC

TTACAATTTAGGTGGCACTTTTCGGGGAAATGTGCGCGGAACCCCTATTTGTTTATTTTTC

TAAATACATTCAAATATGTATCCGCTCATGAGACAATAACCCTGATAAATGCTTCAATAAT

ATTGAAAAAGGAAGAGTATGAGTATTCAACATTTCCGTGTCGCCCTTATTCCCTTTTTTGC

GGCATTTTGCCTTCCTGTTTTTGCTCACCCAGAAACGCTGGTGAAAGTAAAAGATGCTGAA

GATCAGTTGGGTGCACGAGTGGGTTACATCGAACTGGATCTCAACAGCGGTAAGATCCTTG

AGAGTTTTCGCCCCGAAGAACGTTTTCCAATGATGAGCACTTTTAAAGTTCTGCTATGTGG

CGCGGTATTATCCCGTATTGACGCCGGGCAAGAGCAACTCGGTCGCCGCATACACTATTCT

CAGAATGACTTGGTTGAGTACTCACCAGTCACAGAAAAGCATCTTACGGATGGCATGACAG

TAAGAGAATTATGCAGTGCTGCCATAACCATGAGTGATAACACTGCGGCCAACTTACTTCT

GACAACGATCGGAGGACCGAAGGAGCTAACCGCTTTTTTGCACAACATGGGGGATCATGTA

ACTCGCCTTGATCGTTGGGAACCGGAGCTGAATGAAGCCATACCAAACGACGAGCGTGACA

CCACGATGCCTGTAGCAATGGCAACAACGTTGCGCAAACTATTAACTGGCGAACTACTTAC

TCTAGCTTCCCGGCAACAATTAATAGACTGGATGGAGGCGGATAAAGTTGCAGGACCACTT

CTGCGCTCGGCCCTTCCGGCTGGCTGGTTTATTGCTGATAAATCTGGAGCCGGTGAGCGTG
```

-continued

```
GGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGT

GCCTCACTGATTAAGCATTGGTAACTGTCAGACCAAGTTTACTCATATATACTTTAGATTG

ATTTAAAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAAAAGATC

AAAG
```

SEQ ID NO: 9 - Nucleic acid sequence encoding the CpauKASIVa$^{T146S}$
enzyme variant with the PmSAD1tp transit peptide in construct
pSZ6871 (SEQ ID NO: 6). The PmSAD1tp transit peptide is
underlined, and the HA epitope tag is double-underlined.

```
ATGGCTTCCGCGGCATTCACCATGTCGGCGTGCCCCGCGATGACTGGCAGGGCCCCTGGGG

CACGTCGCTCCGGACGGCCAGTCGCCACCCGCCTGAGGGGCTCCACCTTCCAGTGCCTGGT

GAACTCCCACATCGACCCCTGCAACCAGAACGTGTCCTCCGCCTCCCTGTCCTTCCTGGGC

GACAACGGCTTCGGCTCCAACCCCTTCCGCTCCAACCGCGGCCACCGCCGCCTGGGCCGCG

CCTCCCACTCCGGCGAGGCCATGGCCGTGGCCCTGCAGCCCGCCCAGGAGGTGGCCACCAA

GAAGAAGCCCGCCATCAAGCAGCGCCGCGTGGTGGTGACCGGCATGGGCGTGGTGACCCCG

CTGGGCCACGAGCCCGACGTGTTCTACAACAACCTGCTGGACGGCGTGTCCGGCATCTCCG

AGATCGAGAGCTTCGACTGCACCCAGTTCCCCACCCGCATCGCCGGCGAGATCAAGTCCTT

CTCCACCGACGGCTGGGTGGCCCCGAAGCTGTCCAAGCGCATGGACAAGTTCATGCTGTAC

CTGCTGACCGCCGGCAAGAAGGCCCTGGCCGACGCCGGCATCACCGAGGACGTGATGAAGG

AGCTGGACAAGCGCAAGTGCGGCGTGCTGATCGGCTCCGGCATGGGCGGCATGAAGCTGTT

CAACGACTCCATCGAGGCCCTGCGCGTGTCCTACAAGAAGATGAACCCCTTCTGCGTGCCC

TTCGCCACCACCAACATGGGCTCCGCCATGCTGGCCATGGACCTGGGCTGGATGGGCCCCA

ACTACTCCATCTCCACCGCCTGCGCCACCTCCAACTTCTGCATCCTGAACGCCGCCAACCA

CATCATCCGCGGCGAGGCCGACATGATGCTGTGCGGCGGCTCCGACGCCGTGATCATCCCC

ATCGGCCTGGGCGGCTTCGTGGCCTGCCGCGCCCTGTCCCAGCGCAACTCCGACCCCACCA

AGGCCTCCCGCCCCTGGGACTCCAACCGCGACGGCTTCGTGATGGGCGAGGGCGCCGGCGT

GCTGCTGCTGGAGGAGCTGGAGCACGCCAAGAAGCGCGGCGCCACCATCTACGCCGAGTTC

CTGGGCGGCTCCTTCACCTGCGACGCCTACCACATGACCGAGCCGCACCCGGACGGCGCCG

GCGTGATCCTGTGCATCGAGAAGGCCCTGGCCCAGTCCGGCGTGTCCCGCGAGGACGTGAA

CTACATCAACGCCCACGCCACCTCCACCCCGGCCGGCGACATCAAGGAGTACCAGGCCCTG

GCCCACTGCTTCGGCCAGAACTCCGAGCTGCGCGTGAACTCCACCAAGTCCATGATCGGCC

ACCTGCTGGGCGCCGCCGGCGGCGTGGAGGCCGTGACCGTGATCCAGGCCATCCGCACCGG

CTGGATCCACCCCAACCTGAACCTGGAGGACCCCGACGAGGCCGTGGACGCCAAGTTCCTG

GTGGGCCCCAAGAAGGAGCGCCTGAACGTGAAGGTGGGCCTGTCCAACTCCTTCGGCTTCG

GCGGCCACAACTCCTCCATCCTGTTCGCCCCGTACAACACCATGTACCCCTACGACGTGCC

CGACTACGCCTGA
```

SEQ ID NO: 10 - Amino acid sequence of the native CpSAD1tp
transit peptide.
MATASTFSAFNARCGDLRRSAGSGPRRPARPLPVRGRA SEQ ID NO: 11 - Amino acid sequence of the modified CpSAD1tp
transit peptide (with codon bias for improved expression in *P.
moriformis*).
MATASTFSAFNARCGDLRRSAGSGPRRPARPLPVRAAI -continued SEQ ID NO: 12 - Nucleic acid sequence of the modified CpSAD1tp
transit peptide with codon bias for improved expression in *P.
moriformis*. The native sequence is capitalized, and silent
codon changes to the native sequence are underlined. Coding
replacement of the restriction enzyme linker is highlighted
with bold lowercase lettering.
ATGGCCACCGCCTCCACCTTCTCCGCCTTCAACGCCCGCTGCGGCGACCTGCGCCGCTCCG CCGGCTCCGGCCCCCGCCGCCCCGCCCGCCCCCTGCCCGTGCGCgccgccatc

SEQUENCE ID NO: 13 - Nucleic acid sequence of construct pSZ6756
for the expression of the wild-type CpauKASIVa gene in *P.
moriformis* at the THI4 locus.
Nonspecific or vector sequences are in plain uppercase.
Relevant restriction sites (5' → 3': PmeI, KpnI, XbaI, MfeI,
SpeI, EcoRV, SacI, and PmeI) are in bold, underlined lowercase.
PmeI sites delimit the 5' and 3' ends of the transforming DNA.
The 5' and 3' homology targeting arms for integration at the
THI4 locus are in bold lowercase. Proceeding in the 5' to 3'
direction, the CrTUB2 promoter is in boxed, lowercase italics.
The *ScSUC2* selection marker is bold, lowercase italics. The
PmPGH 3'-UTR is in plain, underlined lowercase. The buffer DNA
sequence that follows is in plain lowercase. The PmSAD2-1v3p
promoter is in boxed, uppercase italics. The PmSAD1tp transit
peptide is in bold, underlined, uppercase italics, the
CpauKASIVa gene is in bold, uppercase italics (with the codon
for amino acid 146 boxed), and the HA epitope tag is double-
underlined and in bold, uppercase italics. (CCC codons that
encode for prolines in specific runs of 5 or more contiguous
cytosines in CpauKASIVa are replaced with CCG codons to
minimize PCR amplification errors.) The PmSAD2-1 3'-UTR is in
plain, underlined uppercase.
AGCGGAAGAGCGCCCAAT gtttaaacccctcaactgcgacgctgggaaccttctccgggca ggcgatgtgcgtgggtttgcctccttggcacggctctacaccgtcgagtacgccatgaggc ggtgatggctgtgtcggttgccacttcgtccagagacggcaagtcgtccatcctctgcgtg tgtggcgcgacgctgcagcagtccctctgcagcagatgagcgtgactttggccatttcacg cactcgagtgtacacaatccatttttcttaaagcaaatgactgctgattgaccagatactg taacgctgatttcgctccagatcgcacagatagcgaccatgttgctgcgtctgaaaatctg gattccgaattcgaccctggcgctccatccatgcaacagatggcgacacttgttacaattc ctgtcacccatcggcatggagcaggtccacttagattcccgatcacccacgcacatctcgc taatagtcattcgttcgtgtcttcgatcaatctcaagtgagtgtgcatggatcttggttga cgatgcggtatgggtttgcgccgctggctgcagggtctgcccaaggcaagctaacccagct cctctccccgacaatactctcgcaggcaaagccggtcacttgccttccagattgccaataa actcaattatggcctctgtcatgccatccatgggtctgatgaatggtcacgctcgtgtcct gaccgttccccagcctctggcgtccctgccccgcccaccagcccacgccgcgcggcagtc gctgccaaggctgtctcggaggtacc│ctttcttgcgctatgacacttccagcaaaaggtag│

│ggcgggctgcgagacggcttcccggcgctgcatgcaacaccgatgatgcttcgacccccg│

│aagctccttcggggctgcatgggcgctccgatgccgctccagggcgagcgctgtttaaat│

│gccaggcccccgattgcaaagacattatagcgagctaccaaagccatattcaaacacctag│

│atcactaccacttctacacaggccactcgagcttgtgatcgcactccgctaagggggcgcc│

│tcttcctcttcgtttcagtcacaacccgcaaa│tctagaATATCA*atgctgctgcaggcct*

*tcctgttcctgctggccggcttcgccgccaagatcagcgcctccatgacgaacgagacgtc*

*cgaccgcccctggtgcacttcacccccaacaagggctggat*gaacgaccccaacggcctg

*tggtacgacgagaaggacgccaagtggcacctgtacttccagtacaacccgaacgacaccg*

-continued tctgggggacgcccttgttctggggccacgccacgtccgacgacctgaccaactgggagga ccagcccatcgccatcgccccgaagcgcaacgactccggcgccttctccggctccatggtg gtggactacaacaacacctccggcttcttcaacgacaccatcgacccgcgccagcgctgcg tggccatctggacctacaacacccccggagtccgaggagcagtacatctcctacagcctgga cggcggctacaccttcaccgagtaccagaagaacccccgtgctggccgccaactccacccag ttccgcgacccgaaggtcttctggtacgagccctcccagaagtggatcatgaccgcggcca agtcccaggactacaagatcgagatctactcctccgacgacctgaagtcctggaagctgga gtccgcgttcgccaacgagggcttcctcggctaccagtacgagtgcccccggcctgatcgag gtccccaccgagcaggaccccagcaagtcctactgggtgatgttcatctccatcaaccccg gcgccccggccggcggctccttcaaccagtacttcgtcggcagcttcaacggcacccactt cgaggccttcgacaaccagtccggcgtggtggacttcggcaaggactactacgccctgcag accttcttcaacaccgacccgaccttacgggagcgccctgggcatcgcgtgggcctccaact gggagtactccgccttcgtgcccaccaacccctggcgctcctccatgtccctcgtgcgcaa gttctccctcaacaccgagtaccaggccaacccggagacggagctgatcaacctgaaggcc gagccgatcctgaacatcagcaacgccggcccctggagccggttcgccaccaacaccacgt tgacgaaggccaacagctacaacgtcgacctgtccaacagcaccggcaccctggagttcga gctggtgtacgccgtcaacaccacccagacgatctccaagtccgtgttcgcgacctctcc ctctggttcaagggcctggaggacccgaggagtacctccgcatgggcttcgaggtgtccg cgtcctccttcttcctggaccgcgggaacagcaaggtgaagttcgtgaaggagaaccccta cttcaccaaccgcatgagcgtgaacaaccagcccttcaagagcgagaacgacctgtcctac tacaaggtgtacggcttgctggaccagaacatcctggagctgtacttcaacgacggcgacg tcgtgtccaccaacacctacttcatgaccaccgggaacgccctgggctccgtgaacatgac gacgggggtggacaacctgttctacatcgacaagttccaggtgcgcgaggtcaagtga<u>caa</u>

<u>ttg</u>acgcccgcgcggcgcacctgacctgttctctcgagggcgcctgttctgccttgcgaaa caagcccctggagcatgcgtgcatgatcgtctctggcgccccgccgcgcggtttgtcgccc tcgcgggcgccgcggccgcggggggcgcattgaaattgttgcaaacccccacctgacagattg agggcccaggcaggaaggcgttgagatggaggtacaggagtcaagtaactgaaagttttta tgataactaacaacaaagggtcgtttctggccagcgaatgacaagaacaagattccacatt tccgtgtagaggcttgccatcgaatgtgagcgggcgggccgcggacccgacaaaacccctta cgacgtggtaagaaaaacgtggcgggcactgtccctgtagcctgaagaccagcaggagacg atcggaagcatcacagcacaGGATCCcgcgtctcgaacagagcgcgcagaggaacgctgaa ggtctcgcctctgtcgcacctcagcgcggcatacaccacaataaccacctgacgaatgcgc ttggttcttcgtccattagcgaagcgtccggttcacacacgtgccacgttggcgaggtggc aggtgacaatgatcggtggagctgatggtcgaaacgttcacagcctaggGAT⌐GGGAGCAGT¬

┌TGTCGACCGCCCGCGTCCCGCAGGCAGCGATGACGTGTGCGTGGCCTGGGTGTTTCGTCGA┐

┌AAGGCCAGCAACCCTAAATCGCAGGCGATCCGGAGATTGGGATCTGATCCGAGTTTGGACC┐

┌AGATCCGCCCCGATGCGGCACGGGAACTGCATCGACTCGGCGCGGAACCCAGCTTTCGTAA┐

┌ATGCCAGATTGGTGTCCGATACCTGGATTTGCCATCAGCGAAACAAGACTTCAGCAGCGAG┐

CGTATTTGGCGGGCGTGCTACCAGGGGTTGCATACATTGCCCATTTCTGTCTGGACCGCTTT

ACTGGCGCAGAGGGTGAGTTGATGGGGTTGGCAGGCATCGAAACGCGCGTGCATGGTGTGC

GTGTCTGTTTTCGGCTGCACGAATTCAATAGTCGGATGGGCGACGGTAGAATTGGGTGTGG

CGCTCGCGTGCATGCCTCGCCCCGTCGGGTGTCATGACCGGGACTGGAATCCCCCCTCGCG

ACCATCTTGCTAACGCTCCCGACTCTCCCGACCGCGCGCAGGATAGACTCTTGTTCAACCA

ATCGACActagtACATATGGCTTCCGCGGCATTCACCATGTCGGCGTGCCCCGCGATGAC

TGGCAGGGCCCCTGGGGCACGTCGCTCCGGACGGCCAGTCCCCACCCGCCTGAGGGGCTCC

ACCTTCCAGTGCCTGGTGAACTCCCACATCGACCCCTGCAACCAGAACGTGTCCTCCGCCT

CCCTGTCCTTCCTGGGCGACAACGGCTTCGGCTCCAACCCCTTCCGCTCCAACCGCGGCCA

CCGCCGCCTGGGCCGCGCCTCCCACTCCGGCGAGGCCATGGCCGTGGCCCTGCAGCCCGCC

CAGGAGGTGGCCACCAAGAAGAAGCCCGCCATCAAGCAGCGCCGCGTGGTGGTGACCGGCA

TGGCGTGGTGACCCCGCTGGGCCACGAGCCCGACGTGTTCT ACAACAACCTGCTGGACGG

CGTGTCCGGCATCTCCGAGATCGAGACCTTCGACTGCACCCAGTTCCCCACCCGCATCGCC

GGCGAGATCAAGTCCTTCTCCACCGACGGCTGGGTGGCCCCGAAGCTGTCCAAGCGCATGG

ACAAGTTCATGCTGTACCTGCTGACCGCCGGCAAGAAGGCCCTGGCCGACGCCGGCATCAC

CGAGGACGTGATGAAGGAGCTGGACAAGCGCAAGTGCGGCGTGCTGATCGGCTCCGGCATG

GGCGGCATGAAGCTGTTCAACGACTCCATCGAGGCCCTGCGCGTGTCCTACAAGAAGATGA

ACCCCTTCTGCGTGCCCTTCGCCACCACCAACATGGGCTCCGCATGCTGGCCATGGACCT

GGGCTGGATGGGCCCCAACTACTCCATCTCCACCGCCTGCGCCACCTCCAACTTCTGCATC

CTGAACGCCGCCAACCACATCATCCGCGGCGAGGCCGACATGATGCTGTGCGGCGGCTCCG

ACGCCGTGATCATCCCCATCGGCCTGGGCGGCTTCGTGGCCTGCCGCGCCCTGTCCCAGCG

CAACTCCGACCCCACCAAGGCCTCCCGCCCCTGGGACTCCAACCGCGACGGCTTCGTGATG

GGCGAGGGCGCCGGCGTGCTGCTGCTGGAGGAGCTGGAGCACGCCAAGAAGCGCGGCGCCA

CCATCTACGCCGAGTTCCTGGGCGGCTCCTTCACCTGCGACGCCTACCACATGACCGAGCC

GCACCCGGACGGCGCCGGCGTGATCCTGTGCATCGAGAAGGCCCTGGCCCAGTCCGGCGTG

TCCCGCGAGGACGTGAACTACATCAACGCCCACGCCACCTCCACCCCGGCCGGCGACATCA

AGGAGTACCAGGCCCTGGCCCACTGCTTCGGCCAGAACTCCGAGCTGCGCGTGAACTCCAC

CAAGTCCATGATCGGCCACCTGCTGGGCGCCGCCGGCGGCGTGGAGGCCGTGACCGTGATC

CAGGCCATCCGCACCGGCTGGATCCACCCCAACCTGAACCTGGAGGACCCCGACGAGGCCG

TGGACGCCAAGTTCCTGGTGGGCCCCAAGAAGGAGCGCCTGAACGTGAAGGTGGGCCTGTC

CAACTCCTTCGGCTTCGGCGGCCACAACTCCTCCATCCTGTTCGCCCCCGTACAACACCATG

TACCCCTACGACGTGCCCGACTACGCCTGAgatatcGGAGCGACGAGTGTGCGTGCGGGGC

TGGCGGGAGTGGGACGCCCTCCTCGCTCCTCTCTGTTCTGAACGGAACAATCGGCCACCCC

GCGCTACGCGCCACGCATCGAGCAACGAAGAAAACCCCCCGATGATAGGTTGCGGTGGCTG

CCGGGATATAGATCCGGCCGCACATCAAAGGGCCCCTCCGCCAGAGAAGAAGCTCCTTTCC

CAGCAGACTCCTTCTGCTGCCAAAACACTTCTCTGTCCACAGCAACACCAAAGGATGAACA

GATCAACTTGCGTCTCCGCGTAGCTTCCTCGGCTAGCGTGCTTGCAACAGGTCCCTGCACT

ATTATCTTCCTGCTTTCCTCTGAATTATGCGGCAGGCGAGCGCTCGCTCTGGCGAGCGCTC

-continued

CTTCGCGCCGCCCTCGCTGATCGAGTGTACAGTCAATGAATGGTgagctccagcgccatgc cacgccctttgatggcttcaagtacgattacggtgttggattgtgtgtttgttgcgtagtg tgcatggtttagaataatacacttgatttcttgctcacggcaatctcggcttgtccgcagg ttcaaccccatttcggagtctcaggtcagccgcgcaatgaccagccgctacttcaaggact tgcacgacaacgccgaggtgagctatgtttaggacttgattggaaattgtcgtcgacgcat attcgcgctccgcgacagcacccaagcaaaatgtcaagtgcgttccgatttgcgtccgcag gtcgatgttgtgatcgtcggcgccggatccgccggtctgtcctgcgcttacgagctgacca agcaccctgacgtccgggtacgcgagctgagattcgattagacataaattgaagattaaac ccgtagaaaaatttgatggtcgcgaaactgtgctcgattgcaagaaattgatcgtcctcca ctccgcaggtcgccatcatcgagcagggcgttgctcccggcggcggcgcctggctggggggg acagctgttctcggccatgtgtgtacgtagaaggatgaatttcagctggttttcgttgcac agctgtttgtgcatgatttgtttcagactattgttgaatgttttttagatttcttaggatgc atgatttgtctgcatgcgactGAAGAGgtttaaacCGCCTCTCCCCGCGCGTTGGCCGAT

TCATTAATGCAGCTGGCACGACAGGTTTCCCGACTGGAAAGCGGGCAGTGAGCGCAACGCA

ATTAATGTGAGTTAGCTCACTCATTAGGCACCCCAGGCTTTACACTTTATGCTTCCGGCTC

GTATGTTGTGTGGAATTGTGAGCGGATAACAATTTCACACAGGAAACAGCTATGACCATGA

TTACGCCAAGCTCGAAATTAACCCTCACTAAAGGGAACAAAAGCTGGCAATTCGCCCTATA

GTGAGTCGTATTACGCGCGCTCACTGGCCGTCGTTTTACAACGTCGTGACTGGGAAAACCC

TGGCGTTACCCAACTTAATCGCCTTGCAGCACATCCCCCTTTCGCCAGCTGGCGTAATAGC

GAAGAGGCCCGCACCGATCGCCCTTCCCAACAGTTGCGCAGCCTGAATGGCGAATGGGACG

CGCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTTC

GCCGGCTTTCCCCGTCAAGCTCTAAATCGGGGGCTCCCTTTAGGGTTCCGATTTAGTGCTT

TACGGCACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGACTCTTG

TTCCAAACTGGAACAACACTCAACCCTATCTCGGTCTATTCTTTTGATTTATAAGGGATTT

TGCCGATTTCGGCCTATTGGTTAAAAAATGAGCTGATTTAACAAAAATTTAACGCGAATTT

TAACAAAATATTAACGCTTACAATTTAGGTGGCACTTTTCGGGGAAATGTGCGCGGAACCC

CTATTTGTTTATTTTTCTAAATACATTCAAATATGTATCCGCTCATGAGACAATAACCCTG

ATAAATGCTTCAATAATATTGAAAAAGGAAGAGTATGAGTATTCAACATTTCCGTGTCGCC

CTTATTCCCTTTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAACTGGATCTCAA

CAGCGGTAAGATCCTTGAGAGTTTTCGCCCCGAAGAACGTTTTCCAATGATGAGCACTTTT

AAAGTTCTGCTATGTGGCGCGGTATTATCCCGTATTGACGCCGGGCAAGAGCAACTCGGTC

GCCGCATACACTATTCTCAGAATGACTTGGTTGAGTACTCACCAGTCACAGAAAAGCATCT

TACGGATGGCATGACAGTAAGAGAATTATGCAGTGCTGCCATAACCATGAGTGATAACACT

GCGGCCAACTTACTTCTGACAACGATCGGAGGACCGAAGGAGCTAACCGCTTTTTTGCACA

ACATGGGGGATCATGTAACTCGCCTTGATCGTTGGGAACCGGAGCTGAATGAAGCCATACC

AAACGACGAGCGTGACACCACGATGCCTGTAGCAATGGCAACAACGTTGCGCAAACTATTA

ACTGGCGAACTACTTACTCTAGCTTCCCGGCAACAATTAATAGACTGGATGGAGGCGGATA

-continued

AAGTTGCAGGACCACTTCTGCGCTCGGCCCTTCCGGCTGGCTGGTTTATTGCTGATAAATC

TGGAGCCGGTGAGCGTGGGTCTCGCGGTATCATTGCAGCACTGGGGCCAGATGGTAAGCCC

TCCCGTATCGTAGTTATCTACACGACGGGGAGTCAGGCAACTATGGATGAACGAAATAGAC

AGATCGCTGAGATAGGTGCCTCACTGATTAAGCATTGGTAACTGTCAGACCAAGTTTACTC

ATATATACTTTAGATTGATTTAAAACTTCATTTTTAATTTAAAAGGATCTAGGTGAAGATC

CTTTTTGATAATCTCATGACCAAAATCCCTTAACGTGAGTTTTCGTTCCACTGAGCGTCAG

ACCCCGTAGAAAAGATCAAAGGATCTTCTTGAGATCCTTTTTTTCTGCGCGTAATCTGCTG

CTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTCCTTCTAG

TGTAGCCGTAGTTAGGCCACCACTTCAAGAACTCTGTAGCACCGCCTACATACCTCGCTCT

GCTAATCCTGTTACCAGTGGCTGCTGCCAGTGGCGATAAGTCGTGTCTTACCGGGTTGGAC

TCAAGACGATAGTTACCGGATAAGGCGCAGCGGTCGGGCTGAACGGGGGGTTCGTGCACAC

AGCCCAGCTTGGAGCGAACGACCTACACCGAACTGAGATACCTACAGCGTGAGCTATGAGA

AAGCGCCACGCTTCCCGAAGGGAGAAAGGCGGACAGGTATCCGGTAAGCGGCAGGGTCGGA

ACAGGAGAGCGCACGAGGGAGCTTCCAGGGGGAAACGCCTGGTATCTTTATAGTCCTGTCG

GGTTTCGCCACCTCTGACTTGAGCGTCGATTTTTGTGATGCTCGTCAGGGGGGCGGAGCCT

ATGGAAAAACGCCAGCAACGCGGCCTTTTTACGGTTCCTGGCCTTTTGCTGGCCTTTTGCT

CACATGTTCTTTCCTGCGTTATCCCCTGATTCTGTGGATAACCGTATTACCGCCTTTGAGT

GAGCTGATACCGCTCGCCGCAGCCGAACGACCGAGCGCAGCGAGTCAGTGAGCGAGGA

SEQ ID NO: 14 - Nucleic acid sequence of the CpauKASIVa gene
variants in constructs pSZ6921 and pSZ7123-pSZ7140 with codon
bias for improved expression in *P. moriformis.* (CCC codons that
encode for prolines in specific runs of 5 or more contiguous
cytosines in CpauKASIVa are replaced with CCG codons to
minimize PCR amplification errors.) The PmSAD1tp transit
peptide is underlined, and the HA epitope tag is double-
underlined. The nucleotides encoding for amino acid 146 are
boxed. The rest of these constructs are identical to SEQ ID
NO: 13.

<u>ATGGCTTCCGCGGCATTCACCATGTCGGCGTGCCCCGCGATGACTGGCAGGGCCCCTGGGG</u>

<u>CACGTCGCTCCGGACGGCCAGTCGCCACCCGCCTGAGGGGCTCCACCTTCCAGTGCCTGGT</u>

GAACTCCCACATCGACCCCTGCAACCAGAACGTGTCCTCCGCCTCCCTGTCCTTCCTGGGC

GACAACGGCTTCGGCTCCAACCCCTTCCGCTCCAACCGCGGCCACCGCCGCCTGGGCCGCG

CCTCCCACTCCGGCGAGGCCATGGCCGTGGCCCTGCAGCCCGCCCAGGAGGTGGCCACCAA

GAAGAAGCCCGCCATCAAGCAGCGCCGCGTGGTGGTGACCGGCATGGGCGTGGTGACCCCG

CTGGGCCACGAGCCCGACGTGTTCTACAACAACCTGCTGGACGGCGTGTCCGGCATCTCCG

AGATCGAG[NNN]TTCGACTGCACCCAGTTCCCCACCCGCATCGCCGGCGAGATCAAGTCCTT

CTCCACCGACGGCTGGGTGGCCCCCGAAGCTGTCCAAGCGCATGGACAAGTTCATGCTGTAC

CTGCTGACCGCCGGCAAGAAGGCCCTGGCCGACGCCGGCATCACCGAGGACGTGATGAAGG

AGCTGGACAAGCGCAAGTGCGGCGTGCTGATCGGCTCCGGCATGGGCGGCATGAAGCTGTT

CAACGACTCCATCGAGGCCCTGCGCGTGTCCTACAAGAAGATGAACCCCTTCTGCGTGCCC

TTCGCCACCACCAACATGGGCTCCGCCATGCTGGCCATGGACCTGGGCTGGATGGGCCCCA

ACTACTCCATCTCCACCGCCTGCGCCACCTCCAACTTCTGCATCCTGAACGCCGCCAACCA

CATCATCCGCGGCGAGGCCGACATGATGCTGTGCGGCGGCTCCGACGCCGTGATCATCCCC

ATCGGCCTGGGCGGCTTCGTGGCCTGCCGCGCCCTGTCCCAGCGCAACTCCGACCCCACCA

AGGCCTCCCGCCCCTGGGACTCCAACCGCGACGGCTTCGTGATGGGCGAGGGCGCCGGCGT

-continued

GCTGCTGCTGGAGGAGCTGGAGCACGCCAAGAAGCGCGGCGCCACCATCTACGCCGAGTTC

CTGGGCGGCTCCTTCACCTGCGACGCCTACCACATGACCGAGCCGCACCCGGACGGCGCCG

GCGTGATCCTGTGCATCGAGAAGGCCCTGGCCCAGTCCGGCGTGTCCCGCGAGGACGTGAA

CTACATCAACGCCCACGCCACCTCCACCCCGGCCGGCGACATCAAGGAGTACCAGGCCCTG

GCCCACTGCTTCGGCCAGAACTCCGAGCTGCGCGTGAACTCCACCAAGTCCATGATCGGCC

ACCTGCTGGGCGCCGCCGGCGGCGTGGAGGCCGTGACCGTGATCCAGGCCATCCGCACCGG

CTGGATCCACCCCAACCTGAACCTGGAGGACCCCGACGAGGCCGTGGACGCCAAGTTCCTG

GTGGGCCCCAAGAAGGAGCGCCTGAACGTGAAGGTGGGCCTGTCCAACTCCTTCGGCTTCG

GCGGCCACAACTCCTCCATCCTGTTCGCCCCGTACAACACCATG<u>TACCCCTACGACGTGCC</u>

<u>CGACTACGCCT</u>GA
Codons used to encode each amino acid:

| Construct | Amino Acid | Codon |
|-----------|-----------|-------|
| pSZ6921 | Ser | AGC |
| pSZ7123 | Gly | GGC |
| pSZ7124 | Glu | GAG |
| pSZ7125 | Asp | GAC |
| pSZ7126 | Val | GTC |
| pSZ7127 | Ala | GCC |
| pSZ7128 | Arg | CGC |
| pSZ7129 | Lys | AAG |
| pSZ7130 | Asn | AAC |
| pSZ7131 | Met | ATG |
| pSZ7132 | Ile | ATC |
| pSZ7133 | Trp | TGG |
| pSZ7134 | Cys | TGC |
| pSZ7135 | Tyr | TAC |
| pSZ7136 | Leu | CTG |
| pSZ7137 | Phe | TTC |
| pSZ7138 | Gln | CAG |
| pSZ7139 | His | CAC |
| pSZ7140 | Pro | CCC |

SEQUENCE ID NO: 15 - Nucleic acid sequence of construct pSZ6769
for the expression of the CpauFATB1Δ28 thioesterase gene
variant in *P. moriformis*.
Nonspecific or vector sequences are in plain uppercase.
Relevant restriction sites (5' → 3': PmeI, KpnI, AscI, SnaBI,
SpeI, XhoI, SacI, and PmeI) are in bold, underlined lowercase.
PmeI sites delimit the 5' and 3' ends of the transforming DNA.
The 5' and 3' homology targeting arms for integration at the
DAO1b locus are in bold lowercase. Proceeding in the 5' to 3'
direction, the PmHXT1-2v2p promoter is in boxed, lowercase
italics, while the Kozak sequence (ACC) is in underlined,
lowercase italics. The nucleic acid sequence encoding the
native CpSAD1tp transit peptide and the *Arabidopsis thaliana*
THIC $^{L337M}$ gene variant (AtTHIC $^{L337M}$), which is used as the
selection marker, are in bold, lowercase italics. The PmHSP90
3'-UTR is in plain, underlined lowercase. The buffer DNA
sequence that follows is in plain lowercase. The PmSAD2-1v3p
promoter is in boxed, uppercase italics. The modified (with
codon bias for improved expression in *P. moriformis*) CpSAD1tp
is in bold, underlined, uppercase italics, the nucleic acid
encoding CpauFATB1Δ28 thioesterase gene (with codon bias for
improved expression in *P. moriformis*) is in bold, uppercase
italics, and the 3xFLAG tag is double-underlined and in bold,
uppercase italics.(CCC codons that encode for prolines in
specific runs of 6 or more contiguous cytosines in CpauFATB1Δ28
are replaced with CCG codons to minimize PCR amplification
errors.) The PmSAD2-1 3'-UTR is in plain, underlined
uppercase.
GATCTTCTTGAGATCCTTTTTTTCTGCGCGTAATCTGCTGCTTGCAAACAAAAAAACCACC

GCTACCAGCGGTGGTTTGTTTGCCGGATCAAGAGCTACCAACTCTTTTTCCGAAGGTAACT

GGCTTCAGCAGAGCGCAGATACCAAATACTGTCCTTCTAGTGTAGCCGTAGTTAGGCCACC

ACTTCAAGAACTCTGTAGCACCGCCTACATACCTCGCTCTGCTAATCCTGTTACCAGTGGC

TGCTGCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCGAACGA

-continued

CCTACACCGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCACGAGGGAG

CTTCCAGGGGGAAACGCCTGGTATCTTTATAGTCCTGTCGGGTTTCGCCACCTCTGACTTG

AGCGTCGATTTTTGTGATGCTCGTCAGGGGGGCGGAGCCTATGGAAAAACGCCAGCAACGC

GGCCTTTTTACGGTTCCTGGCCTTTTGCTGGCCTTTTGCTCACATGTTCTTTCCTGCGTTA

TCCCCTGATTCTGTGGATAACCGTATTACCGCCTTTGAGTGAGCTGATACCGCTCGCCGCA

GCCGAACGACCGAGCGCAGCGAGTCAGTGAGCGAGGAAGCGGAAGAGCGCCCAATgtttaa accagcccgcaccctcgttgatctgggagccctgcgcagccccttaaatcatctcagtcagg tttctgtgttcaactgagcctaaagggctttcgtcatgcgcacgagcacacgtatatcggc cacgcagtttctcaaaagcggtagaacagttcgcgagccctcgtaggtcgaaaacttgcgc cagtactattaaattaaattaattgatcgaacgagacgcgaaacttttgcagaatgccacc gagtttgcccagagaatgggagtggcgccattcaccatccgcctgtgcccggcttgattcg ccgagacgatggacggcgagaccagggagcggcttgcgagccccgagccggtagcaggaac aatgatcgacaatcttcctgtccaattactggcaaccattagaaagagccggagcgcgttg aaagtctgcaatcgagtaattttcgatacgtcgggcctgctgaaccctaaggctccggac tttgtttaaggcgatccaagatgcacgcggccccaggcacgtatctcaagcacaaacccca gccttagtttcgagactttgggagatagcgaccgatatctagtttggcattttgtatatta attacctcaagcaatggagcgctctgatgcggtgcagcgtcggctgcagcacctggcagtg gcgctagggtcgccctatcgctcggaacctggtcagctggctcccgcctcctgctcagcct cttccggtacc⌐ccgctcccgtctggtcctcacgttcgtgtacggcctggatcccggaaagg⌐

⌐gcggatgcacgtggtgttgccccgccattggcgcccacgtttcaaagtccccggccagaaa⌐

⌐tgcacaggaccggcccggctcgcacaggccatgacgaatgcccagatttcgacagcaaaac⌐

⌐aatctggaataatcgcaaccattcgcgttttgaacgaaacgaaaagacgctgtttagcacg⌐

⌐tttccgatatcgtggggccgaagcatgattggggggaggaaagcgtggccccaaggtagc⌐

⌐ccattctgtgccacacgccgacgaggaccaatccccggcatcagccttcatcgacggctgc⌐

⌐gccgcacatataaagccggacgccttcccgacacgttcaaacagttttatttcctccactt⌐

⌐cctgaatcaaacaaatcttcaaggaagatcctgctcttgagca⌐GCTAGCaccatggccacc gcatccactttctcggcgttcaatgcccgctgcggcgacctgcgtcgctcggcgggctccg ggccccggcgcccagcgaggccctccccgtgcgcgggcgcgcccgcgccacgctgacgtt cgacccccccacgaccaactccgagcgcgccaagcagcgcaagcacaccatcgaccctcc tccccgacttccagcccatcccctccttcgaggagtgcttccccaagtccacgaaggagc acaaggaggtggtgcacgaggagtccggccacgtcctgaaggtgcccttccgccgcgtgca cctgtccggcggcgagcccgccttcgacaactacgacacgtcggcccccagaacgtcaac gcccacatcggcctggcgaagctgcgcaaggagtggatcgaccgccgcgagaagctgggca cgccccgctacacgcagatgtactacgcgaagcagggcatcatcacggaggagatgctgta ctgcgcgacgcgcgagaagctggaccccgagttcgtccgctccgaggtcgcgcgggccgc gccatcatcccctccaacaagaagcacctggagctggagcccatgatcgtgggccgcaagt -continued tcctggtgaaggtgaacgcgaacatcggcaactccgccgtggcctcctccatcgaggagga ggtctacaaggtgcagtgggccaccatgtggggcgccgacaccatcatggacctgtccacg ggccgccacatccacgagacgcgcgagtggatcctgcgcaactccgcggtccccgtgggca ccgtccccatctaccaggcgctggagaaggtggacggcatcgcggagaacctgaactgggaa ggtgttccgcgagacgctgatcgagcaggccgagcagggcgtggactacttcacgatccac gcgggcgtgctgctgcgctacatccccctgaccgccaagcgcatgacgggcatcgtgtccc gcggcggctccatccacgcgaagtggtgcctggcctaccacaaggagaacttcgcctacga gcactgggacgacatcctggacatctgcaaccagtacgacgtcgccctgtccatcggcgac ggcctgcgccccggctccatctacgacgccaacgacacggcccagttcgccgagctgctga cccagggcgagctgacgcgccgcgcgtgggagaaggacgtgcaggtgatgaacgagggccc cggccacgtgcccatgcacaagatccccgagaacatgcagaagcagctggagtggtgcaac gaggcgcccttctacaccctgggccccctgacgaccgacatcgcgcccggctacgaccaca tcacctccgccatcggcgcggccaacatcggcgcgccctgggcacgccctgctgtgctacgt gacgcccaaggagcacctgggcctgcccaaccgcgacgacgtgaaggcgggcgtcatcgcc tacaagatcgccgcccacgcggccgacctggccaagcagcaccccacgcccaggcgtgggg acgacgcgctgtccaaggcgcgcttcgagttccgctggatggacagttcgcgctgtccct ggaccccatgacggcgatgtccttccacgacgagacgctgcccgcggacggcgcgaaggtc gcccacttctgctccatgtgcgggccccaagttctgctccatgaagatcacggaggacatcc gcaagtacgccgaggagaacggctacggctccgccgaggaggccatccgccagggcatgga cgccatgtccgaggagttcaacatcgccaagaagacgatctccggcgagcagcacggcgag gtcggcggcgagatctacctgcccgagtcctacgtcaaggccgcgcagaagtgaTACCTTA TtacgtaAcagacgaccttggcaggcgtcgggtagggaggtggtggtgatggcgtctcgat gccatcgcacgcatccaacgaccgtatacgcatcgtccaatgaccgtcggtgtcctctctg cctccgtttttgtgagatgtctcaggcttggtgcatcctcgggtggccagccacgttgcgcg tcgtgctgcttgcctctcttgcgcctctgtggtactggaaaatatcatcgaggcccgtttt tttgctcccatttcctttccgctacatcttgaaagcaaacgacaaacgaagcagcaagcaa agagcacgaggacggtgaacaagtctgtcacctgtatacatctatttccccgcgggtgcac ctactctctctcctgccccggcagagtcagctgccttacgtgacGGATCCcgcgtctcgaa cagagcgcgcagaggaacgctgaaggtctcgcctctgtcgcacctcagcgcggcatacacc acaataaccacctgacgaatgcgcttggttcttcgtccattagcgaagcgtccggttcaca cacgtgccacgttggcgaggtggcaggtgacaatgatcggtggagctgatggtcgaaacgt tcacagcctaggGATATC GGGAGCAGTTGTCGACCGCCCGCGTCCCGCAGGCAGCGATGAC

GTGTGCGTGGCCTGGGTGTTTCGTCGAAAGGCCAGCAACCCTAAATCGCAGGCGATCCGGA

GATTGGGATCTGATCCGAGTTTGGACCAGATCCGCCCCGATGCGGCACGGGAACTGCATCG

ACTCGGCGCGGAACCCAGCTTTCGTAAATGCCAGATTGGTGTCCGATACCTGGATTTGCCA

TCAGCGAAACAAGACTTCAGCAGCGAGCGTATTTGGCGGGCGTGCTACCAGGGTTGCATAC

ATTGCCCATTTCTGTCTGGACCGCTTTACTGGCGCAGAGGGTGAGTTGATGGGGTTGGCAG

-continued

GCATCGAAACGCGCGTGCATGGTGTGCGTGTCTGTTTTCGGCTGCACGAATTCAATAGTCG

GATGGGCGACGGTAGAATTGGGTGTGGCGCTCGCGTGCATGCCTCGCCCCGTCGGGTGTCA

TGACCGGGACTGGAATCCCCCCTCGCGACCATCTTGCTAACGCTCCCGACTCTCCCGACCG

CGCGCAGGATAGACTCTTGTTCAACCAATCGACAactagtAACAATGGCCACCGCCTCCAC

CTTCTCCGCCTTCAACGCCCGCTGCGGCGACCTGCGCCGCTCCGCCGGCTCCGGCCCCCGC

CGCCCCGCCCGCCCCCTGCCCGTGCGCGCCGCCATCAACGCCTCCGCCCACCCCAAGGCCA

ACGGCTCCGCCGTGAACCTGAAGTCCGGCTCCCTGAACACCCAGGAGGACACCTCCTCCTC

TCCGCCTCCCCGCGCCTTCCTGAACCAGCTGCCCGACTGGTCCATGCTGGTGGACTCCGTG

GGCCTGAAGTCCGTGGTGCTGGACGGCCTGGTGTCCCGCCAGATCTTCTCCATCCGCTCCT

ACGAGATCGGCGCCGACCGCACCGCCTCCATCGAGACCCTGATGAACCACCTGCAGGAGAC

CTCCATCAACCACTGCAAGTCCCTGGGCCTGCTGAACGACGGCTTCGGCCGCACCCCCGGC

ATGTGCAAGAACGACCTGATCTGGGTGCTGACCAAGATGCAGATCATGGTGAACCGCTACC

CCACCTGGGGCGACACCGTGGAGATCAACACCTGGTTGTCCCACTCCGGCAAGATCGGCAT

GGCCTCCGACTGGCTGATCACCGACTGCAACACCGGCGAGATCCTGATCCGCGCCACCTCC

GTGTGGGCCATGATGAACCAGAAGACCCGCCGCTTCTCCCGCCTGCCCTACGAGGTGCGCC

AGGAGCTGACCCCTCACTACGTGGACTCCCCGCACGTGATCGAGGACAACGACCGCAAGCT

GCACAAGTTCGACGTGAAGACGGCGACTCCATCCGCAAGGGCCTGACCCCTCGCTGGAAC

GACCTGGACGTGAACCAGCACGTGTCCAACGTGAAGTACATCGGCTGGATCCTGGAGTCCA

TGCCCATCGAGGTGCTGGAGACCCAGGAGCTGTGCTCCCTGACCGTGGAGTACCGCCGCGA

GTGCGGCATGGACTCCGTGCTGGAGTCCGTGACCGCCATGGACCCCTCCGAGGACGAGGGC

CGCTCCCAGTACAAGCACCTGCTGCGCCTGGAGGACGGCACCGACATCGTGAAGGGCCGCA

CCGAGTGGCGCCCCAAGAACGCCGGCACCAACGGCGCCATCTCCACCGCCAAGCCCTCCAA

CGGCAACTCCGTGTCCATGGACTACAAGGACCACGACGGCGACTACAAGGACCACGACATC

GACTACAAGGACGACGACGACAAGTGActcgagGGAGCGACGAGTGTGCGTGCGGGGCTGG

CGGGAGTGGGACGCCCTCCTCGCTCCTCTCTGTTCTGAACGGAACAATCGGCCACCCCGCG

CTACGCGCCACGCATCGAGCAACGAAGAAAACCCCCCGATGATAGGTTGCGGTGGCTGCCG

GGATATAGATCCGGCCGCACATCAAAGGGCCCCTCCGCCAGAGAAGAAGCTCCTTTCCCAG

CAGACTCCTTCTGCTGCCAAAACACTTCTCTGTCCACAGCAACACCAAAGGATGAACAGAT

CAACTTGCGTCTCCGCGTAGCTTCCTCGGCTAGCGTGCTTGCAACAGGTCCCTGCACTATT

ATCTTCCTGCTTTCCTCTGAATTATGCGGCAGGCGAGCGCTCGCTCTGGCGAGCGCTCCTT

CGCGCCGCCCTCGCTGATCGAGTGTACAGTCAATGAATGGTgagctcagcgtctgcgtgtt gggagctggagtcgtgggcttgacgacggcgctgcagctgttgcaggatgtgcctggcgtg cgcgttcacgtcgtggctgagaaatatggcgacgaaacgttgacggctggggccggcgggc tgtggatgccatacgcattgggtacgcggccattggatgggattgataggcttatggaggg ataatagagttttgccggatccaacgcatgtggatgcggtatcccggtgggctgaaagtg tggaaggatagtgcattggctattcacatgcactgcccaccccttttggcaggaaatgtgc cggcatcgttggtgcaccgatggggaaaatcgacgttcgaccactacatgaagatttatac gtctgaagatgcagcgactgcgggtgcgaaacggatgacggtttggtcgtgtatgtcacag catgtgctggatcttgcgggctaactcccctgccacggcccattgcaggtgtcatgttga -continued ctggagggtacgacctttcgtccgtcaaattcccagaggaggacccgctctgggccgacat tgtgcccactGAAGAGCgtttaaacCGCCTCTCCCCGCGCGTTGGCCGATTCATTAATGCA

GCTGGCACGACAGGTTTCCCGACTGGAAAGCGGGCAGTGAGCGCAACGCAATTAATGTGAG

TTAGCTCACTCATTAGGCACCCCAGGCTTTACACTTTATGCTTCCGGCTCGTATGTTGTGT

GGAATTGTGAGCGGATAACAATTTCACACAGGAAACAGCTATGACCATGATTACGCCAAGC

TCGAAATTAACCCTCACTAAAGGGAACAAAAGCTGGCCAATTCGCCCTATAGTGAGTCGTA

TTACAATTCACTGGCCGTCGTTTTACAACGTCGTGACTGGGAAAACCCTGGCGTTACCCAA

CTTAATCGCCTTGCAGCACATCCCCCTTTCGCCAGCTGGCGTAATAGCGAAGAGGCCCGCA

CCGATCGCCCTTCCCAACAGTTGCGCAGCCTGAATGGCGAATGGGACGCGCCCTGTAGCGG

CGCATTAAGCGCGGCGGGTGTGGTGGTTACGCGCAGCGTGACCGCTACACTTGCCAGCGCC

CTAGCGCCCGCTCCTTTCGCTTTCTTCCCTTCCTTTCTCGCCACGTTCGCCGGCTTTCCCC

GTCAAGCTCTAAATCGGGGGCTCCCTTTAGGGTTCCGATTTAGTGCTTTACGGCACCTCGA

CCCCAAAAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAACTGGAA

CAACACTCAACCCTATCTCGGTCTATTCTTTTGATTTATAAGGGATTTTGCCGATTTCGGC

CTATTGGTTAAAAAATGAGCTGATTTAACAAAAATTTAACGCGAATTTTAACAAAATATTA

ACGCTTACAATTTAGGTGGCACTTTTCGGGGAAATGTGCGCGGAACCCCTATTTGTTTATT

TTTCTAAATACATTCAAATATGTATCCGCTCATGAGACAATAACCCTGATAAATGCTTCAA

TAATATTGAAAAAGGAAGAGTATGAGTATTCAACATTTCCGTGTCGCCCTTATTCCCTTTT

TTGCGGCATTTTGCCTTCCTGTTTTTGCTCACCCAGAAACGCTGGTGAAAGTAAAAGATGC

TGAAGATCAGTTGGGTGCACGAGTGGGTTACATCGAACTGGATCTCAACAGCGGTAAGATC

CTTGAGAGTTTTCGCCCCGAAGAACGTTTTCCAATGATGAGCACTTTTAAAGTTCTGCTAT

GTGGCGCGGTATTATCCCGTATTGACGCCGGGCAAGAGCAACTCGGTCGCCGCATACACTA

TTCTCAGAATGACTTGGTTGAGTACTCACCAGTCACAGAAAAGCATCTTACGGATGGCATG

ACAGTAAGAGAATTATGCAGTGCTGCCATAACCATGAGTGATAACACTGCGGCCAACTTAC

TTCTGACAACGATCGGAGGACCGAAGGAGCTAACCGCTTTTTTGCACAACATGGGGGATCA

TGTAACTCGCCTTGATCGTTGGGAACCGGAGCTGAATGAAGCCATACCAAACGACGAGCGT

GACACCACGATGCCTGTAGCAATGGCAACAACGTTGCGCAAACTATTAACTGGCGAACTAC

TTACTCTAGCTTCCCGGCAACAATTAATAGACTGGATGGAGGCGGATAAAGTTGCAGGACC

ACTTCTGCGCTCGGCCCTTCCGGCTGGCTGGTTTATTGCTGATAAATCTGGAGCCGGTGAG

CGTGGGTCTCGCGGTATCATTGCAGCACTGGGGCCAGATGGTAAGCCCTCCCGTATCGTAG

TTATCTACACGACGGGGAGTCAGGCAACTATGGATGAACGAAATAGACAGATCGCTGAGAT

AGGTGCCTCACTGATTAAGCATTGGTAACTGTCAGACCAAGTTTACTCATATATACTTTAG

ATTGATTTAAAACTTCATTTTTAATTTAAAAGGATCTAGGTGAAGATCCTTTTTGATAATC

TCATGACCAAAATCCCTTAACGTGAGTTTTCGTTCCACTGAGCGTCAGACCCCGTAGAAAA

GATCAAAG

What is claimed is:

1. A polynucleotide encoding a β-ketoacyl-acyl carrier protein (ACP) synthase (KAS) IVa enzyme (KASIVa) variant, wherein the KASIVa variant comprises at least about 80%, 85%, 90%, 91%, 92%, 93%, 94%, 95%, 96%, 97%, 98% or 99% identity to amino acid residues 34-523 of SEQ ID NO: 4 and comprises an X at the position corresponding to position 146; wherein X is an amino acid residue selected from the group consisting of glycine (G) and serine(S), wherein the position is with reference to SEQ ID NO: 4, and wherein the KASIVa variant catalyzes the elongation of a medium-chain fatty acyl-ACP.

2. The polynucleotide of claim 1, wherein the KASIVa variant comprises a plastid transit peptide.

3. The polynucleotide of claim 2, wherein the plastid transit peptide comprises at least about 80%, 85%, 90%, 91%, 92%, 93%, 94%, 95%, 96%, 97%, 98% or 99% identity to amino acid residues 1-33 of SEQ ID NO: 3, amino acid residues 1-33 SEQ ID NO: 4, SEQ ID NO: 10 or SEQ ID NO: 11.

4. The polynucleotide of claim 2, wherein the plastid transit peptide is encoded by a polynucleotide comprising at least about 80%, 85%, 90%, 91%, 92%, 93%, 94%, 95%, 96%, 97%, 98% or 99% identity to SEQ ID NO: 12.

5. The polynucleotide of claim 1, comprising codon bias for improved expression in a microalgal host cell.

6. An expression cassette comprising the polynucleotide of claim 1.

7. A vector comprising the polynucleotide of claim 1.

8. The vector of claim 7, further comprising a polynucleotide encoding a fatty acyl-ACP thioesterase.

9. The vector of claim 8, wherein the thioesterase preferentially hydrolyzes C10-ACP substrates.

10. The vector of claim 8, wherein the thioesterase is a Cuphea FATB thioesterase.

11. The vector of claim 8, wherein the thioesterase is a Cuphea FATB thioesterase selected from the group consisting of Cuphea hookeriana FATB2 (ChFATB2), Cuphea paucipetala FATB1 (Cpau FATB1), Cuphea palustris FATB1 (Cpal FATB1), Cuphea ignea FATB1 (Cignea FATB1), Cuphea avigera FATB1 (Ca FATB1, Cuphea painteri FATB1 (Cpai FATB1), Cuphea procumbens FATB1 (CprocFATB1), Cuphea procumbens FATB3 (CprocFATB3), Cuphea crassiflora FATB1 (CcrasFATB1), Cuphea koehneana FATB3 (CkoeFATB3), Cuphea leptopoda FATB1 (CleptFATB1), Cuphea angustifolia FATB1 (CangFATB1), Cuphea llavea FATB1 (CllaFATB1), Cuphea lophostoma FATB1 (ClopFATB1), Cuphea PSR23 FatB3 (CuPSR23FATB3), Cuphea viscosissima FatB1 (CvisFATB1), and Cuphea glossostoma FatB1 (CgFATB1).

12. The vector of claim 8, wherein the thioesterase comprises at least about 80%, 85%, 90%, 91%, 92%, 93%, 94%, 95%, 96%, 97%, 98% or 99% identity to amino acid residues 39-392 of SEQ ID NO: 5, wherein the thioesterase catalyzes the production of increased levels of C10 fatty acids and/or has increased specificity for C10 fatty acids in comparison to a wild-type thioesterase.

13. A non-natural KASIVa variant encoded by the polynucleotide of claim 1.

14. A fusion protein comprising the non-natural or variant KASIVa of claim 13 and a heterologous peptide or polypeptide.

15. A host cell comprising the polynucleotide of claim 1.

16. The host cell of claim 15, wherein one or more endogenous lipid biosynthesis enzymes selected from the group consisting of a fatty acyl thioesterase A (FATA), a fatty acyl thioesterase B (FATB), a 1-acylglycerol-3-phosphate O-acyltransferase (LPAAT), a glycerol-3-phosphate acyltransferase (GPAT), an acyl CoA:diacylglycerol acyltransferase (DGAT), a fatty acid elongase (FAE) and a long-chain acyl-CoA synthetase (LACS) are deleted, knocked-out or knocked down.

17. The host cell of claim 16, further comprising one or more exogenous or heterologous lipid biosynthesis enzymes selected from the group consisting of a fatty acyl thioesterase A (FATA), a fatty acyl thioesterase B (FATB), a 1-acylglycerol-3-phosphate O-acyltransferase (LPAAT), a glycerol-3-phosphate acyltransferase (GPAT), an acyl CoA: diacylglycerol acyltransferase (DGAT), a fatty acid elongase (FAE), and a long-chain acyl-CoA synthetase (LACS).

18. The host cell of claim 17, further comprising one or more exogenous or heterologous enzymes selected from the group consisting of a sucrose invertase and a 4-amino-5-hydroxymethyl-2-methylpyrimidine phosphate synthase (THIC).

19. The host cell of claim 15, wherein the host cell is an oleaginous microalgal cell.

20. The host cell of claim 19, wherein the host cell is a microalgal cell of the genus *Prototheca* or *Chlorella*.

21. The host cell of claim 20, wherein the host cell is selected from the group consisting of *Prototheca moriformis, Prototheca krugani, Prototheca stagnora, Prototheca zopfii* and *Chlorella prototothecoides.*

* * * * *